(12) United States Patent
Ameres et al.

(10) Patent No.: US 11,859,248 B2
(45) Date of Patent: *Jan. 2, 2024

(54) NUCLEIC ACID MODIFICATION AND IDENTIFICATION METHOD

(71) Applicant: IMBA—INSTITUT FÜR MOLEKULARE BIOTECHNOLOGIE GMBH, Vienna (AT)

(72) Inventors: Stefan L. Ameres, Klosterneuburg (AT); Brian Reichholf, Vienna (AT); Veronika A. Herzog, Vienna (AT); Johannes Zuber, Vienna (AT); Matthias Muhar, Vienna (AT)

(73) Assignee: IMBA—INSTITUT FÜR MOLEKULARE BIOTECHNOLOGIE GMBH, Vienna (AT)

( * ) Notice: Subject to any disclaimer, the term of this patent is extended or adjusted under 35 U.S.C. 154(b) by 143 days.

This patent is subject to a terminal disclaimer.

(21) Appl. No.: 17/651,657

(22) Filed: Feb. 18, 2022

(65) Prior Publication Data

US 2023/0054714 A1    Feb. 23, 2023

Related U.S. Application Data

(63) Continuation of application No. 16/301,680, filed as application No. PCT/EP2018/059518 on Apr. 13, 2018, now Pat. No. 11,299,779.

(30) Foreign Application Priority Data

Apr. 13, 2017 (EP) ................................. 17166629
Apr. 4, 2018 (EP) ................................. 18165712

(51) Int. Cl.
C12Q 1/68       (2018.01)
C12Q 1/6869     (2018.01)
(Continued)

(52) U.S. Cl.
CPC .......... *C12Q 1/6869* (2013.01); *C07H 21/00* (2013.01); *C12N 15/11* (2013.01); *C12Q 1/6806* (2013.01); *C12N 2310/00* (2013.01)

(58) Field of Classification Search
None
See application file for complete search history.

(56) References Cited

U.S. PATENT DOCUMENTS

2003/0180769 A1   9/2003  Metzker
2004/0259135 A1  12/2004  Cleary et al.
(Continued)

FOREIGN PATENT DOCUMENTS

CN   105980575 A     9/2016
WO   2006/125808 A1 11/2006

OTHER PUBLICATIONS

International Search Report from International Patent Application No. PCT/EP2018/059518, dated Jun. 7, 2018.
(Continued)

*Primary Examiner* — Aaron A Priest
(74) *Attorney, Agent, or Firm* — Greer, Burns & Crain, Ltd

(57) ABSTRACT

A method of identifying a polynucleic acid (PNA) is presented, including the steps of providing a PNA; modifying one or more nucleobases of the PNA by addition or removal of a hydrogen bonding partner, thereby altering the base pairing capacity of the one or more nucleobases; base pairing a complementary nucleic acid to the PNA, including base pairing to at least one modified nucleobase; identifying the sequence of the complementary nucleic acid at least at
(Continued)

the position that is complementary to at least one modified nucleobase.

13 Claims, 63 Drawing Sheets

Specification includes a Sequence Listing.

(51) Int. Cl.
  *C07H 21/00* (2006.01)
  *C12N 15/11* (2006.01)
  *C12Q 1/6806* (2018.01)

(56) References Cited

U.S. PATENT DOCUMENTS

| | | |
|---|---|---|
| 2011/0183320 A1 | 7/2011 | Flusberg et al. |
| 2013/0316916 A1 | 11/2013 | Flusberg et al. |
| 2018/0080061 A1 | 3/2018 | Cleary et al. |

OTHER PUBLICATIONS

Written Opinion of the International Searching Authority from International Patent Application No. PCT/EP2018/059518, dated Jun. 7, 2018.
Burton, K., "Oxidation of Pyrimidine Nucleosides and Nucleotides by Osmium Tetroxide", Biochemical Journal (1967), 104(2), pp. 686-694.
Cleary et al., "Biosynthetic Labeling of RNA with Uracil Phosphoribosyltransferase Allows Cell-Specific Microarray Analysis of mRNA Synthesis and Decay", Nature Biotechnology (2005), 23(2), pp. 232-237.
Darzynkiewicz et al., "Cytometry of DNA Replication and RNA Synthesis: Historical Perspective and Recent Advances Based on 'Click Chemistry'", Cytometry Part A (2011), 79(5), pp. 328-337.
Dölken et al., "High-Resolution Gene Expression Profiling for Simultaneous Kinetic Parameter Analysis of RNA synthesis and Decay", RNA (2008), 14(9), pp. 1959-1972.
Duffy et al., "Tracking Distinct RNA Populations Using Efficient and Reversible Covalent Chemistry", Molecular Cell (2015), 59(5), pp. 858-866.
Eberwine et al., "The Promise of Single-Cell Sequencing", Nature Methods (2014), 11(1), pp. 25-27.
Eidinoff et al., "Incorporation of Unnatural Pyrimidine Bases into Deoxyribonucleic Acid of Mammalian Cells", Science (1959), 129(3362), pp. 1550-1551.
Emilsson et al., "Thiolation of transfer RNA in *Escherichia coli* Varies with Growth Rate", Nucleic Acids Research (1992), 20(17), pp. 4499-4505.
Fuchs et al., "4sUDRB-seq: Measuring Genomewide Transcriptional Elongation Rates and Initiation Frequencies within Cells", Genome Biology (2014), 15(5), pp. 1-10.
Hara et al., "4Thiouridine-Specific Spin-Labeling", Biochemical and Biophysical Research Communications (1970), 38(2), pp. 305-311.
Harcourt et al., "Chemical and Structural Effects of Base Modifications in Messenger RNA", Nature (2017), vol. 541, pp. 339-346.
Hartmann et al., "Chapter 8.3.3: Postsynthetic Labeling of a 4-Thiouridine-Modified RNA", Handbook of RNA Biolchemistry (2014), vol. 2, pp. 164-166.
Herzog et al., "Thiol-Linked Alkylation of RNA to Assess Expression Dynamics", Nature Methods (2017), 14(12), pp. 1198-1204.
Hong et al., "Analysis and Optimization of Copper-Catalyzed Azide-Alkyne Cycloaddition for Bioconjugation", Angewandte Chemie (2009), 48(52), pp. 9879-9883.
Jao et al., "Exploring RNA Transcription and Turnover in vivo by Using Click Chemistry", PNAS (2008), 105(41), pp. 15779-15784.
Klijn et al., "A Comprehensive Transcriptional Portrait of Human Cancer Cell Lines", Nature Biotechnology (2015), 33(3), pp. 306-312.
Kramer et al., "Near-UV Stress in *Salmonella typhimurium*: 4-Thiouridine in tRNA, ppGpp, and ApppGpp as Components of an Adaptive Response", Journal of Bacteriology (1988), 170(5), pp. 2344-2351.
Larsen et al., "Flow Cytometric Analysis of RNA Synthesis by Detection of Bromouridine Incorporation", Current Protocols in Cytometry (2000), Chapt. 7, unit 7.2, pp. 1-11.
Melvin et al., "Incorporation of 6-Thioguanosine and 4-Thiouridine into RNA: Application to Isolation of Newly Synthesized RNA by Affinity Chromatography", European Journal of Biochemistry (1978), 92(2), pp. 373-379.
Miller et al., "TU-Tagging: Cell Type Specific RNA Isolation from Intact Complex Tissues", Nature Methods (2009), 6(6), pp. 439-441.
Nilsen, T.W., "RNA Sequencing by Primer Extension", Cold Spring Harbor Protocols (2013), pp. 1182-1185.
Pearson, R.G., "Physical and Inorganic Chemistry: Hard and Soft Acids and Bases", Journal of the American Chemical Society (1963), 85(22), pp. 3533-3539.
Presolski et al., "Copper-Catalyzed Azide-Alkyne Click Chemistry for Bioconjugation", Current Protocols in Chemical Biology (2011), 3(4), pp. 153-162.
Rabani et al., "Metabolic Labeling of RNA Uncovers Principles of RNA Production and Degradation Dynamics in Mammalian Cells", Nature Biotechnology (2011), 29(5), pp. 436-442.
Rieder et al., "Alkene-Tetrazine Ligation for Imaging Cellular DNA", Angewandte Communications (2014), 53(35), pp. 9168-9172.
Riml et al., "Osmium-Mediated Transformation of 4-Thiouridine to Cytidine as Key to Study RNA Dynamics by Sequencing", Angewandte Chemie (2017), 56(43), pp. 1-6.
Schofield et al., "TimeLapse-seq: Adding a Temporal Dimension to RNA Sequencing Through Nucleoside Recoding", Nature Methods (2018), 15(3), pp. 1-10.
Schwalb et al., "TT-seq Maps the Human Transient Transcriptome", Science (2016), 352(6290), pp. 1225-1228.
Shu et al., "N6-Allyladenosine: A New Small Molecule for RNA Labeling Identified by Mutation Assay", Journal of the American Chemical Society (2017), 139(48), pp. 1-5.
Sochacka et al., "2-Thiouracil Deprived of Thiocarbonyl Function Preferentially Base Pairs with Guanine Rather Than Adenine in RNA and DNA Duplexes", Nucleic Acids Research (2015), 43(5), pp. 2499-2512.
Spitzer et al., "PAR-CLIP (Photoactivatable Ribonucleoside-Enhanced Crosslinking and Immunoprecipitation): A Step-by-Step Protocol to the Transcriptome-Wide Identification of Binding Sites of RNA-Binding Proteins", Methods in Enzymology (2014), vol. 539, pp. 113-161.
Tani et al., "Genome-wide Determination of RNA Stability Reveals Hundreds of Short-Lived Noncoding Transcripts in Mammals", Genome Research (2012), 22(5), pp. 947-956.
Testa et al., "Thermodynamics of RNA-RNA Duplexes with 2- or 4-Thiouridines: Implications for Antisense Design and Targeting a Group I Intron", Biochemistry (1999), 38(50), pp. 16655-16662.
Thomas et al., "4-Thiouridine Triggers Both Growth Delay Induced by Near-Ultraviolet Light and Photoreception" European Journal of Biochemistry (1980), vol. 113, 67-74.
Woodford et al. "Selective Isolation of Newly Synthesized Mammalian mRNA After in vivo Labeling with 4-Thiouridine or 6-Thioguanosine", Analytical Biochemistry (1988), 171(1), pp. 166-172.
Yu et al., "Ionization of Bromouracil and Fluorouracil Stimulates Base Mispairing Frequencies with Guanine", The Journal of Biological Chemistry (1993), 268(21), pp. 15935-15943.
Written Opinion of the International Preliminary Examining Authority from International Patent Application No. PCT/EP2018/059518, dated Mar. 13, 2019.
Chen et al., "High-Resolution N6-Methyladenosine (m6A) Map Using Photo-Crosslinking-Assisted m6A Sequencing", Angewandte Chemie (2015), 54(5), pp. 1587-1590.

(56) References Cited

OTHER PUBLICATIONS

Khoddami et al., "Identification of Direct Targets and Modified Bases of RNA Cytosine Methyltransferases", Nature Biotechnology (2013), 31(5), pp. 458-464.
Li et al., "DNA Methylation Detection: Bisulfite Genomic Sequencing Analysis", Methods in Molecular Biology (2011), vol. 791, pp. 11-21.
Notice of Reasons for Rejection received for Japanese Application No. 2019-556245, dated Apr. 12, 2022.
Ryvkin, P., et al., "HAMR: high-throughput annotation of modified ribonucleotides," RNA 19, No. 12, 2013, pp. 1684-1692.
First Office Action received in Chinese Application No. 201880024846.5, dated Mar. 1, 2023.
Zheng, F., et al., "Progress of Synthesis of Modified Peptide Nucleic Acid," Chin Pharm J, vol. 50, No. 22, Nov. 2015, pp. 1936-1945. (English Abstract).

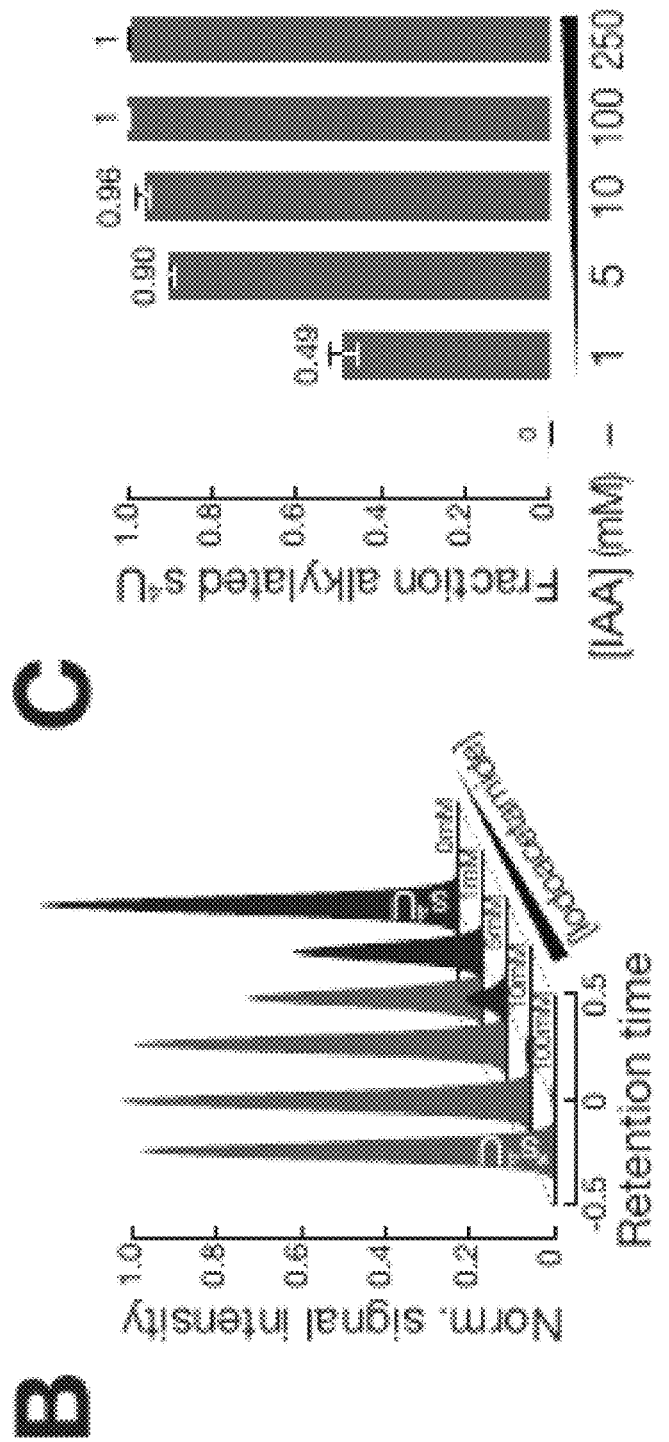
Fig. 3 (Continuation)

Fig. 5B (Continuation)
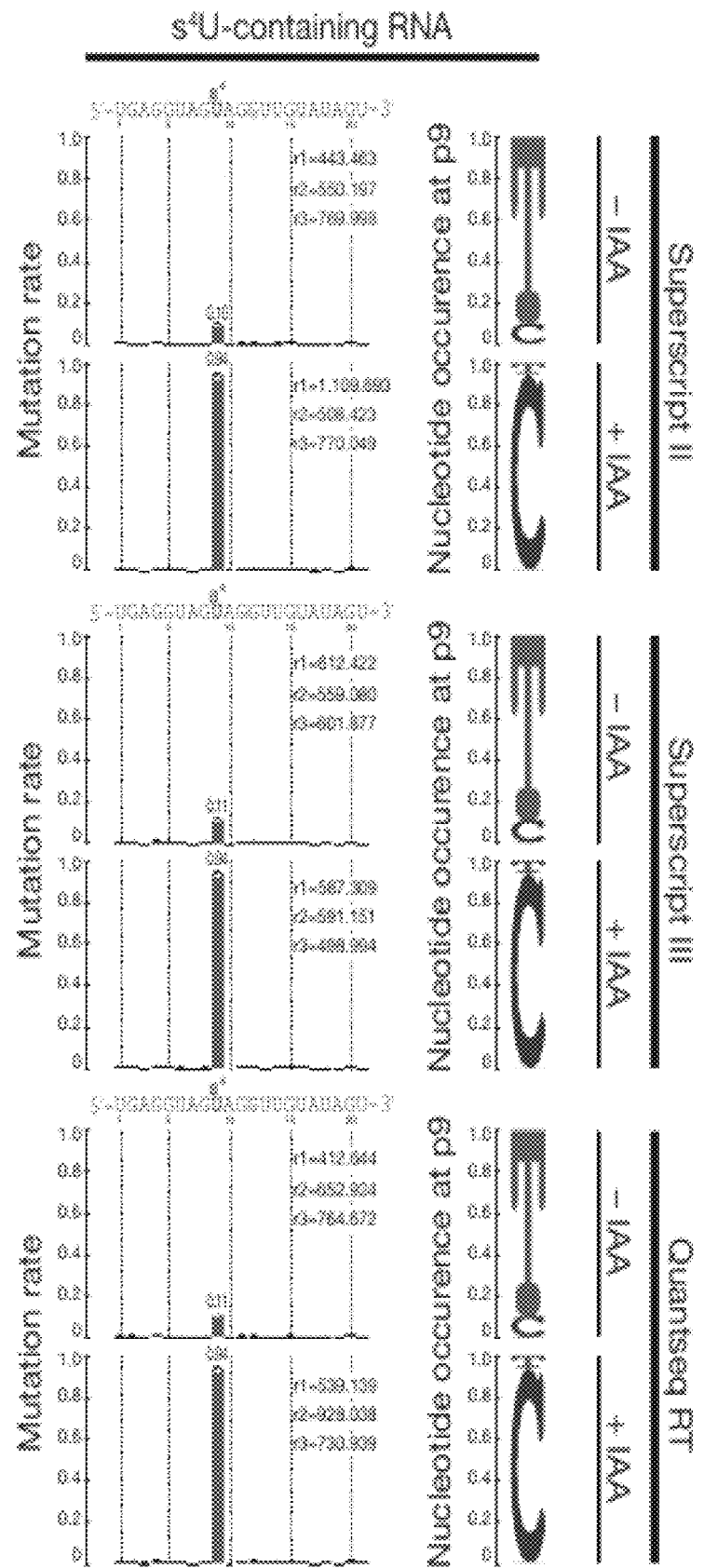

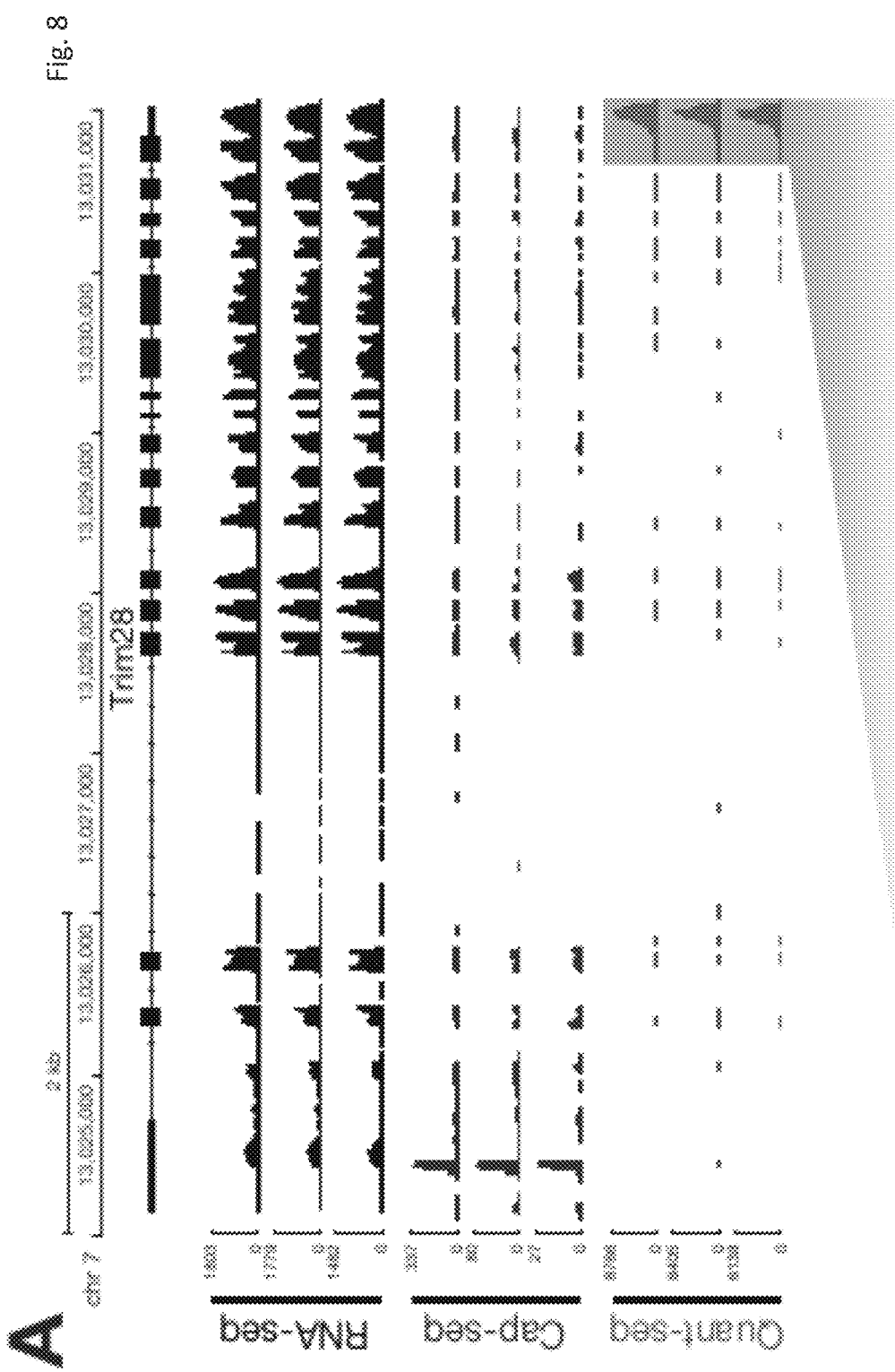

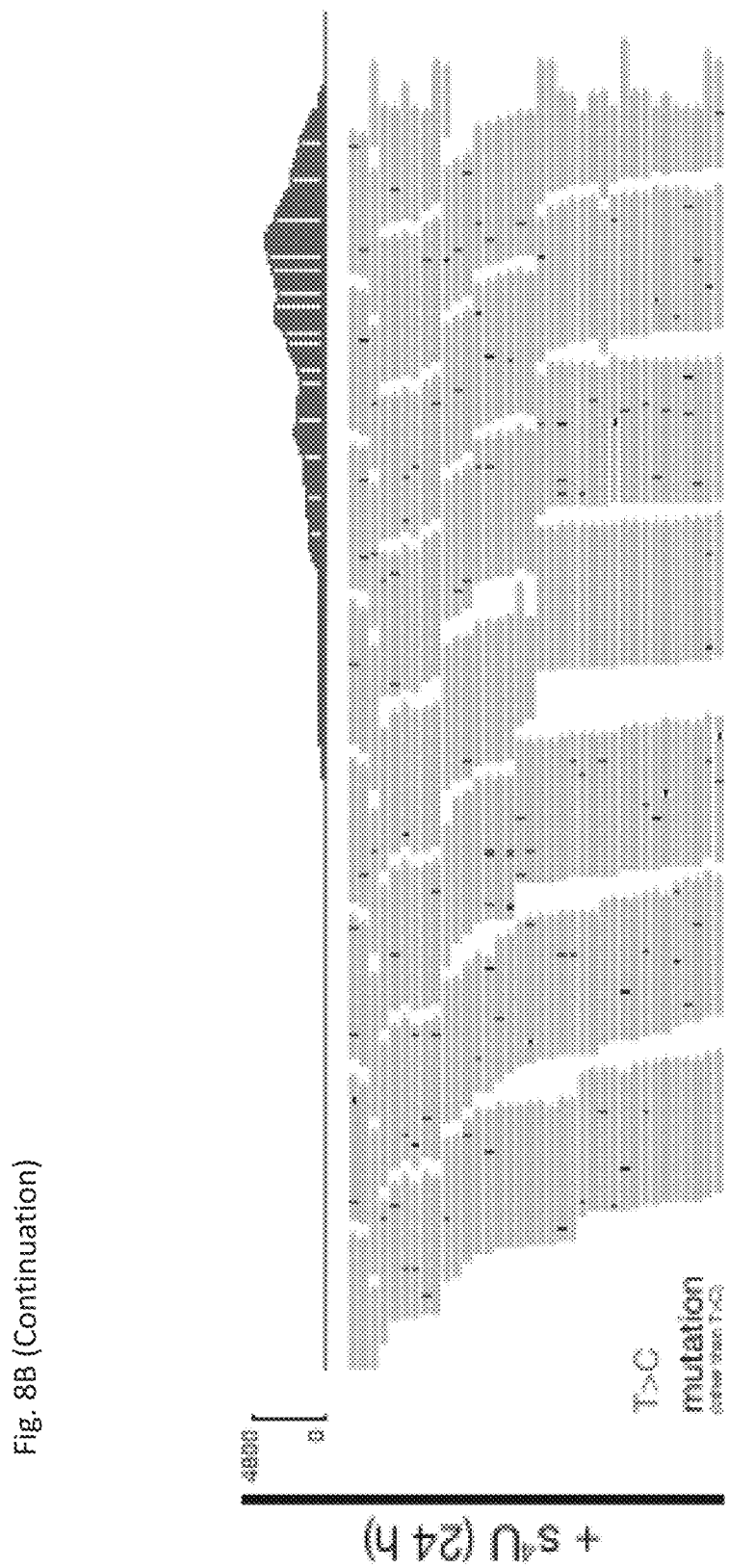
Fig. 8B (Continuation)

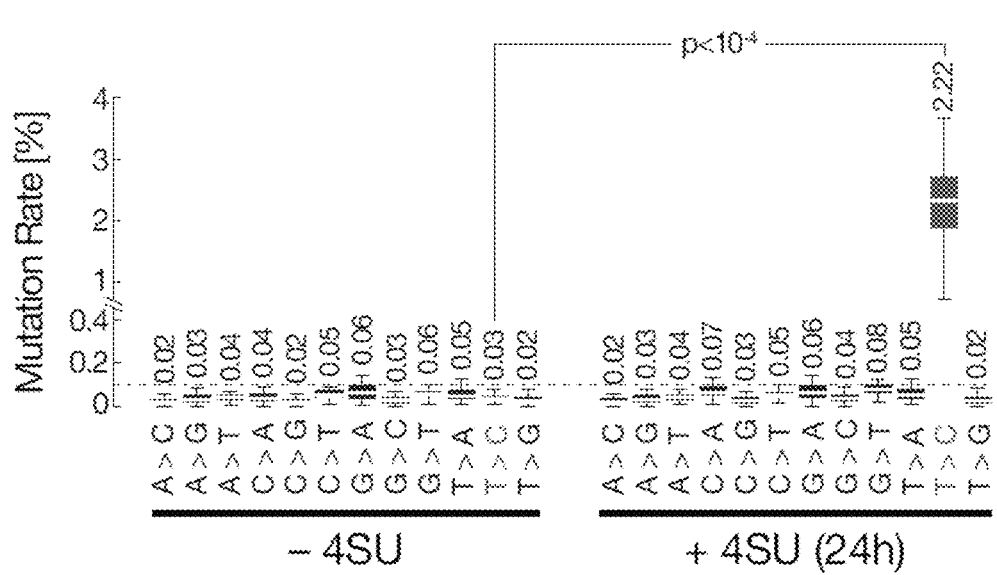
Cont. Fig. 12 B

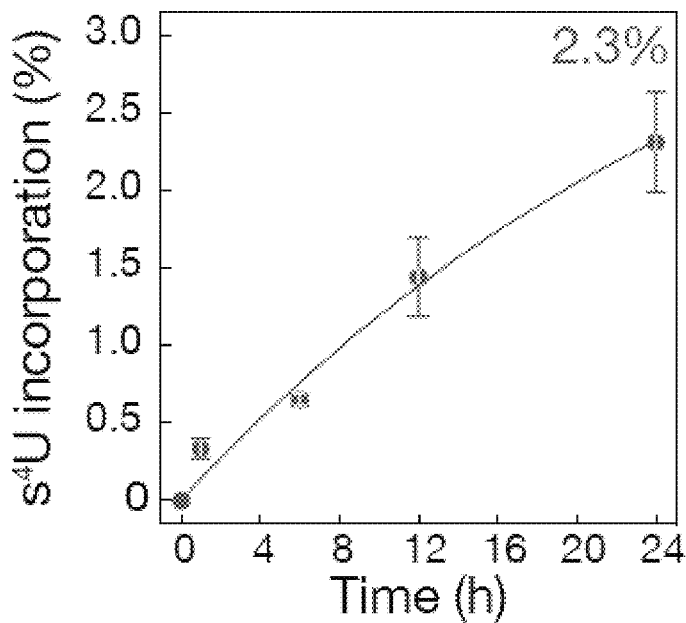
Fig. 18
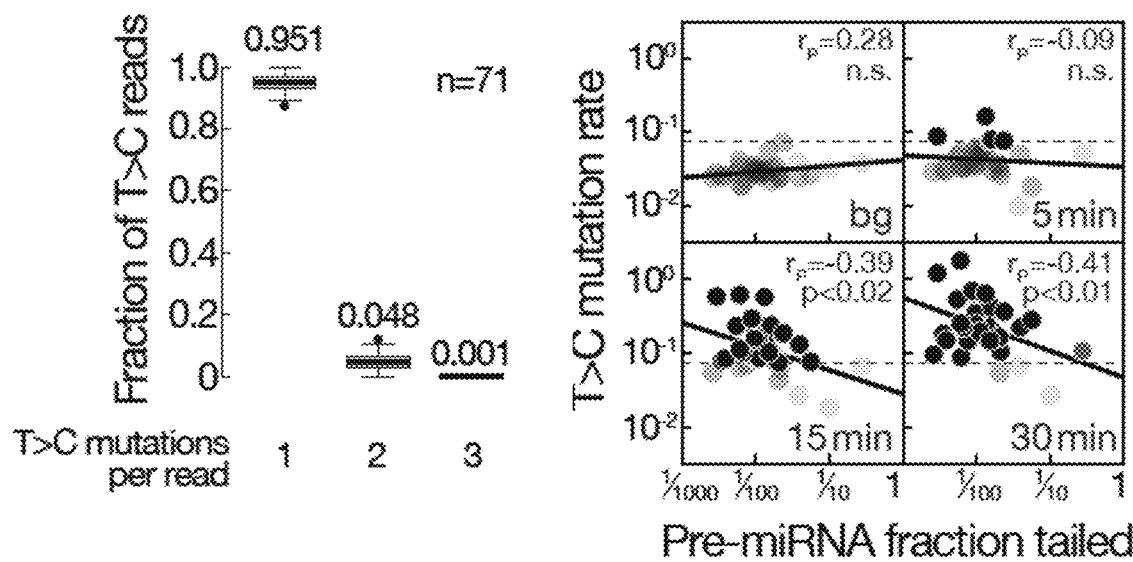
Fig. 20
Fig. 22

A

6-Thioguanine (s⁶G)    *s⁶G

B

A

SEQUENCE LISTING

```
<160> NUMBER OF SEQ ID NOS: 11

<210> SEQ ID NO 1
<211> LENGTH: 76
<212> TYPE: RNA
<213> ORGANISM: Artificial Sequence
<220> FEATURE:
<223> OTHER INFORMATION: 5L-let-7-3L

<400> SEQUENCE: 1
acacucuuuc ccuacacgac gcucuuccga ucuugaggua guagguugua uaguagaucg      60
gaagagcaca cgucuc                                                     76

<210> SEQ ID NO 2
<211> LENGTH: 76
<212> TYPE: RNA
<213> ORGANISM: Artificial Sequence
<220> FEATURE:
<223> OTHER INFORMATION: 5L-let-7-s4U-p9-3L
<220> FEATURE:
<221> NAME/KEY: modified_base
<222> LOCATION: (42)..(42)
<223> OTHER INFORMATION: s4u
```

```
<400> SEQUENCE: 2
acacucuuuc ccuacacgac gcucuuccga ucuugaggua guagguugua uaguagaucg      60
gaagagcaca cgucuc                                                    76

<210> SEQ ID NO 3
<211> LENGTH: 21
<212> TYPE: RNA
<213> ORGANISM: Artificial Sequence
<220> FEATURE:
<223> OTHER INFORMATION: let-7-s6G sequence
<220> FEATURE:
<221> NAME/KEY: modified_base
<222> LOCATION: (8)..(8)
<223> OTHER INFORMATION: s6g

<400> SEQUENCE: 3
ugagguagua gguuguauag u                                              21

<210> SEQ ID NO 4
<211> LENGTH: 34
<212> TYPE: DNA
<213> ORGANISM: Artificial Sequence
<220> FEATURE:
<223> OTHER INFORMATION: RT primer

<400> SEQUENCE: 4
gtgactggag ttcagacgtg tgctcttccg atct                                34

<210> SEQ ID NO 5
<211> LENGTH: 58
<212> TYPE: DNA
<213> ORGANISM: Artificial Sequence
<220> FEATURE:
<223> OTHER INFORMATION: Solexa_PCR_fwd

<400> SEQUENCE: 5
aatgatacgg cgaccaccga gatctacact ctttccctac acgacgctct tccgatct      58

<210> SEQ ID NO 6
<211> LENGTH: 64
<212> TYPE: DNA
<213> ORGANISM: Artificial Sequence
<220> FEATURE:
<223> OTHER INFORMATION: Solexa_IDX_rev
<220> FEATURE:
<221> NAME/KEY: misc_feature
<222> LOCATION: (25)..(30)
<223> OTHER INFORMATION: n is a, c, g, or t

<400> SEQUENCE: 6
caagcagaag acggcatacg agatnnnnnn gtgactggag ttcagacgtg tgctcttccg     60
atct                                                                 64

<210> SEQ ID NO 7
<211> LENGTH: 21
<212> TYPE: DNA
<213> ORGANISM: Artificial Sequence
<220> FEATURE:
<223> OTHER INFORMATION: mature dme-let-7 sequence

<400> SEQUENCE: 7
tgaggtagta ggttgtatag t                                              21

<210> SEQ ID NO 8
<211> LENGTH: 77
```

```
<212> TYPE: RNA
<213> ORGANISM: Artificial Sequence
<220> FEATURE:
<223> OTHER INFORMATION: synthetic RNA oligonucleotide
<220> FEATURE:
<221> NAME/KEY: misc_structure
<222> LOCATION: (44)..(44)
<223> OTHER INFORMATION: 5-Br-U

<400> SEQUENCE: 8
acacucuuuc cuacacgac gcucuuccga ucuugaggua guuagguugu auaguagauc      60
ggaagagcac acgucuc                                                   77

<210> SEQ ID NO 9
<211> LENGTH: 34
<212> TYPE: DNA
<213> ORGANISM: Artificial Sequence
<220> FEATURE:
<223> OTHER INFORMATION: primer

<400> SEQUENCE: 9
gtgactggag ttcagacgtg tgctcttccg atct                                34

<210> SEQ ID NO 10
<211> LENGTH: 58
<212> TYPE: DNA
<213> ORGANISM: Artificial Sequence
<220> FEATURE:
<223> OTHER INFORMATION: primer

<400> SEQUENCE: 10
aatgatacgg cgaccaccga gatctacact ctttccctac acgacgctct tccgatct      58

<210> SEQ ID NO 11
<211> LENGTH: 64
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(30)
<223> OTHER INFORMATION: n is a, c, g, or t

<400> SEQUENCE: 11
caagcagaag acggcatacg agatnnnnnn gtgactggag ttcagacgtg tgctcttccg    60
atct                                                                64
```

NUCLEIC ACID MODIFICATION AND IDENTIFICATION METHOD

RELATED APPLICATIONS

This application is a continuation of, and claims priority under 35 U.S.C. 120 from Ser. No. 16/301,680, filed Nov. 14, 2018, which claims priority from PCT/EP2018/059518 filed Apr. 13, 2018, which claims the benefit of priority to European Application Nos. 17166629.0; filed Apr. 13, 2017 and 18165712.3; filed Apr. 4, 2018, all incorporated by reference.

The present invention relates to the field of nucleic acid processing and sequencing.

REFERENCE TO AN ELECTRONIC SEQUENCE LISTING

The contents of the electronic sequence listing (1376314.txt; Size: 3.02 KB; and Date of Creation: Nov. 13, 2018) is herein incorporated by reference in its entirety.

BACKGROUND

Nucleotide analogs, such as 4-Thiouridine ($s^4U$) and 6-thioguanosine ($s^6G$) are readily incorporated into nascent RNAs, e.g. by natural enzymes (Tani et al., Genome Res. 22, 947-956 (2012)). Among popular analogs are 5-bromouridine (5BrU), 5-ethynyluridine (5-EU), 6-thioguanosine ($s^6G$) and 4-thiouridine ($s^4U$), which are readily incorporated by cells and further provide unique physicochemical properties for antibody detection, cycloaddition reactions, and thiol-specific reactivity and affinity, respectively (Eidinoff et al., Science. 129, 1550-1551 (1959); Jao et al. PNAS 105, 15779-15784 (2008); Melvin et al. Eur. J. Biochem. 92, 373-379 (1978); Woodford et al. Anal. Biochem. 171, 166-172 (1988); Dölken et al. RNA 14, 1959-1972 (2008); Rabani et al. Nat Biotechnol. 29, 436-442 (2011)). 4-thiouridine ($s^4U$) is the most widely used nucleotide analog to study the dynamics of RNA expression. Similar to other nucleotides, $s^4U$ is rapidly taken up by cells without the requirement for electroporation or lipofection. In cells, phosphorylation by cellular uridine-kinases generates an accumulating pool of phosphorylated $s^4U$ that is efficiently incorporated into newly synthesized RNA in a broad range of cell types including fly, murine and human cells (Dölken 2008, supra). Furthermore, cell-type-specific labeling of transcripts in vivo in flies and mice can be achieved by employing 4-thiouracil in combination with cell-type-specific expression of *Toxoplasma gondii* uracil phosphoribosyltransferase (UPRT), which couples ribose-5-phosphate to the N1 nitrogen of uracil (or 4-thiouracil) to yield (4-thio-)uridine monophosphate that is incorporated into RNA (Cleary et al. Nat Biotechnol. 23, 232-237 (2005)). Current protocols employing 4-thiouridine ($s^4U$) metabolic RNA-labeling to characterize intracellular RNA biogenesis, processing, and turnover kinetics employ biochemical separation through reversible biotinylation of the thiolgroup in $s^4U$ [e.g. through N-[6-(Biotinamido)hexyl]-3'-(2'-pyridyldithio)propionamide (HPDPBiotin) or biotin-coupled methanethiosulfonates (MTS-Biotin)](Cleary et al., 2005, supra). However, like any biochemical separation method, the underlying protocols are time-consuming and typically encounter the problem of low signal-to-noise ratios because of limitations in biotinylation efficiency (particularly when applied to short RNA species) and off-target reactivity (Duffy et al., Mol Cell. 59, 858-866 (2015); Neymotin et al., RNA 20:1645-1652 (2014)).

WO 2006/125808 A1 describes a microarray-based method of analyzing de-novo transcribed RNA that contains thiolated RNA.

WO 2004/101825 A1 and WO 2016/154040 A2 relate to methods of biosynthetic labeling and separation of RNA.

Miller et al., Nature Methods 6(6), 2009: 439-441, describes labelling of RNA through a 4-thiouracil food source in *Drosophila melanogaster*.

Schwalb et al., Science 352(6290), 2016: 1225-1228, relates to a method of transient transcriptome sequencing capable of estimating total mRNA synthesis and degradation.

Hartmann et al., Handbook of RNA Biochemistry vol. 2, 2014, chapter 8.3.3, pp. 164-166, relates to postsynthetic labelling of 4-thiouridine-modified RNA by modifying 4-thiouridine residues with iodoacetamides or sulfur-based compounds.

Testa et al., Biochemistry, 38(50), 1999: 16655-16662, discloses altered base pairing strength of thiouracil ($s^2U$ and $s^4U$) as compared to uracil.

Hara et al., Biochemical and Biophysical Research Communications 38(2), 1970: 305-311, discloses 4-thiouridine-specific spin-labeling of tRNA.

Fuchs et al., Genome Biology 15(5), 2014: 1465-6906 relates to a determination of genome-wide transcriptional elongation rates by determining 4-thiouridine tags on RNA. The method requires biotinylation and purification of such labeled RNA.

Furthermore, in reversible biotinylation strategies labeled RNA can only be analyzed in isolation, i.e. not in the context of total RNA. Precise measurements of intracellular RNA kinetics by high-throughput sequencing therefore require analysis of three RNA subsets per timepoint (labeled RNA, total RNA and unlabeled RNA), rendering these approaches expensive and downstream analyses impractical.

Therefore, it is a goal of the present invention to simplify methods of detecting modified nucleic acids, preferably to the extent to allow automated detection.

SUMMARY

The present invention is based on nucleotide-analog derivatization chemistry that enables to detect modifications in polynucleotide (PNA) species at single-nucleotide resolution. The inventive method provides a scalable, highly quantitative, cost- and time-effective method for the rapid and transcriptome-wide analysis of PNA modification.

In a first aspect, the invention provides a method of identifying a polynucleic acid (PNA) comprising the steps of providing a PNA; modifying one or more nucleobases of the PNA by addition or removal of a hydrogen bonding partner, thereby altering the base pairing capacity of the one or more nucleobases; base pairing a complementary nucleic acid to the PNA, including base pairing to at least one modified nucleobase; identifying the sequence of the complementary nucleic acid at least at the position that is complementary to at least one modified nucleobase.

In preferred embodiments, the PNA is synthesized in a cell, in particular already with a modification that by itself altering the base pairing capacity or can be further modified to altering the base pairing capacity. Accordingly, the invention can also be defined as a method of identifying a polynucleic acid (PNA) comprising the steps of expressing a PNA in cell; isolating the PNA from the cell; modifying one or more nucleobases of the PNA in the cell and/or after isolation; wherein the modification(s) in the cell or after the isolation or both together add or remove a hydrogen bonding partner of one or more nucleobase, thereby altering the base pairing capacity of the one or more nucleobases; base pairing a complementary nucleic acid to the PNA, including base pairing to at least one modified nucleobase; identifying the sequence of the complementary nucleic acid at least at the position that is complementary to at least one modified nucleobase.

The invention further provides a kit for performing the inventive method, in particular a kit comprising a thiol modified nucleobase and an alkylating agent suitable for alkylating the thiol modified nucleobase at the thiol group, wherein the alkylating agent comprises a hydrogen boding donor or acceptor.

All embodiments of the invention are described together in the following detailed description and all preferred embodiments relate to all embodiments, aspects, methods and kits alike. E.g. Kits or their components can be used in or be suitable for inventive methods. Any component used in the described methods can be provided in the kit. Preferred and detailed descriptions of the inventive methods read alike on kit components or their suitability or combination of kit components for a given method step. All embodiments can be combined with each other, except where otherwise stated.

DETAILED DESCRIPTION

The present invention relates to a method, wherein a polynucleic acid (abbreviated PNA) is modified to create synthetic PNA (also referred to as modified PNA). The presence of the synthetic PNA in a sample of PNAs can be found in the PNA sequencing readout of said sample, thereby identifying the modified PNA. An advantage of the invention is that this identification can be done without purification/separation from non-modified PNA.

In detail, the inventive method comprises the steps of modifying one or more nucleobases of a PNA by addition or removal of a hydrogen bonding partner, thereby altering the base pairing capacity (or behaviour) of the one or more nucleobases; base pairing a complementary nucleic acid to the PNA, including base pairing to at least one modified nucleobase.

Natural nucleobases are A (adenine), G (guanine), C (cytosine) and T (thymine)/U (uracil). The inventive modification leads to a nucleobase that is non-natural as compared to A, G, C, U nucleotides in case of RNA or A, G, C, T nucleotides in case of DNA. The modification leads to an altered base pairing behaviour, thereby altering the preferential base pairing (binding by hydrogen bonds) between A and T/U and between C and G. This means that the base pairing to a natural nucleobase as complementary nucleic acid changes from one natural nucleic acid to another natural nucleic acid. Preferably the complementary nucleic acid is DNA and T is used instead of U. Altered A may bind to C or G; altered T or U may bind to C or G; altered C may bind to A or T/U; altered G may bind to A or T/U. Such modifications are known in the art. Modifications are usually minor and keep changes to a minimum just so that the base pairing behaviour is changed. E.g. A and G each maintain their purine ring system and C and T/U maintain their pyrimidine ring. For example, Harcourt et al. (Nature 2017, 541: 339-346) provides a review and summary of such modifications. Example modifications are modifications of A to $m^6A$, to $m^1A$, to inosine, to 2-aminoadenine; modifications of C to $m^5C$ (5-methyl cytosine), to $hm^5C$ (5-hydroxymethyl cytosine), to pseudouridine, to 2-thiocytosine, to 5-halocytosine, to 5-propynyl (—C≡C—CH$_3$) cytosine, 5-alkynyl cytosine; modifications of T or of U to 2-thiouracil, to $s^4U$ (4-thiouracil), to 2-thiothymine, to 4-pyrimidinone, to pseudouracil, to 5-halouracil, e.g. 5-bromouracil (also as 5-Bromouridine (5BrU)), 5-propynyl (—C≡C—CH$_3$) uracil, 5-alkynyl uracil, e.g. 5-ethynyluracil; modifications of G to hypoxanthine, to xanthine, to isoguanine; modifications of A or of G to 6-methyl and other 6-alkyl derivatives of adenine and guanine; to 2-propyl and other 2-alkyl derivatives of adenine and guanine. Further modifications are to 6-azo-uracil, -cytosine and -thymine, 8-halo-, 8-amino-, 8 thiol-, 8-thioalkyl-, 8-hydroxyl- and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Although the natural nucleobase is preferably modified to its closest modified nucleobase as indicated above, in principle and nucleobase can be modified to any modified nucleobase as mentioned above. The relevant factor is the change in hydrogen bonding pattern so that another base pairing partner will bind to the modified nucleobase as compared to the unmodified nucleobase. Change in bonding partners does not require absolute certainty, it is sufficient that a certainty of binding to a natural binding partner is changed, such as by at least 10%, at least 20%, at least 30%, at least 40%, at least 50%, at least 60%, at least 70%, at least 80%, at least 90%, or 100%. A particular nucleobase may bind more than one complementary nucleobase (especially wobble bases). Reference conditions to determine changes are at standard conditions for reverse transcriptase, preferably atmospheric pressure and 37° C., in a physiological isotonic aqueous solution. Example conditions are 50 mM Tris-HCl, 75 mM KCl, 3 mM MgCl$_2$, 10 mM DTT at pH 7.5-8.5. Any such change can be monitored by current detection means, such as sequencing and sequence comparison. Also, more than one modification can be included into a PNA molecule and only one per molecule or per plurality of molecules needs detection. Of course, the higher the change ratio in hydrogen bonding from one natural nucleobase to another natural nucleobase (in the complementary nucleic acid), the higher the certainty of the detection. Therefore, higher base pairing ratio changes, such as by at least 50% or at least 80%, are preferred.

"Halo" means halogen, in particular F, Cl, Br or I; Br is particularly preferred, such as in 5BrU. "Alkyl" means an alkyl residue, preferably an alkyl residue of $C_1$-$C_{12}$ in length, branched or unbranched, substituted or not substituted. Preferred are alkyl residues of C1-C4 in length with an optional 0 substituent and/or an optional N substituent, such as in acetamide or any other alkyl carbonyl, carbonic acid or amide.

Particularly preferred modified nucleobases of the PNA are of 5-bromouridine (5BrU), 5-ethynyluridine (5-EU), 6-thioguanosine ($s^6G$), 4-thiouridine ($s^4U$), 5-Vinyl-uridine, 5 Azidomethyl-uridine and $N^6$-allyladenosine ($a^6$).

The base pairing behaviours are known in the art or can be deduced from the changes in hydrogen bond donors or acceptors, including their obstruction to prevent their pairing. E.g. 4-pyrimidinone (modified U or T) preferably base pairs with G, instead of A (Sochacka et al., Nucleic Acids Res. 2015 Mar. 11; 43(5): 2499-2512).

The modification of the nucleobases of the PNA can be a substitution of a hydrogen (H) on an oxygen (O) or on a nitrogen (N) atom by a substituent, such as a carbon (e.g. as in a methyl group or other alkyl group) thereby removing the H as hydrogen bond donor. The modification can be a substitution of a free electron pair of oxygen (O) or nitrogen (N) atom by substituent, such as a carbon (e.g. as in a methyl group or other alkyl group) thereby removing the electron pair as hydrogen bond acceptor. The modification may comprise the replacement of an O by sulphur (S) or SH and then performing one of the above modifications, especially alkylation of the S or SH. A preferred method of replacement of O by S or SH is by biosynthesis and providing an enzyme, e.g. a transcriptase with S or SH modified nucleotides, such as $s^4U$. The transcriptase may be in a cell.

The inventive modification may be a one-step modification or a modification by more than one step, such as two, three or more steps. E.g. a first part of the modification is performed in one reaction environment, such as a cell, and a second modification is performed in another reaction environment, e.g. after isolation of the PNA from the cell. Preferably, such a second or further modification is dependent on the first modification, e.g. is performed on the atoms changed by the first modification. In particular preferred is a multi-step modification, wherein the first modification is an enzymatic modification, such as by incorporation of modified nucleotides/nucleobases by an enzyme, such as by a RNA or DNA polymerase, into the PNA. In this step, for enzymatic processivity, only small modifications are included so as not or tolerably impair enzyme activity. Small modifications are e.g. a change in only 1 or 2 atoms (not counting hydrogen) as compared to a corresponding natural nucleobase. In a further step, the incorporated modified nucleobase can be further modified by any means, e.g. to the modified nucleobases described herein, such as by wet chemical methods, including alkylation. Such a further modification can be outside a cell, enzymatic or non-enzymatic. It preferably targets the modifications introduced in the first step. A (first) modification in a cell may be an induced or enhanced modification, such by supplying the cell with modified nucleobases (e.g. as modified nucleotides), which the cell then incorporates in biosynthesised PNA. "Enhanced" means beyond natural occurrences of modifications.

It is also possible that a (first) modification is a natural process inside a cell without providing the cell with a modified nucleobase. Such a natural process is e.g. thiolation of tRNA (Thomas et al., Eur J Biochem. 1980, 113(1): 67-74; Emilsson et al., Nucleic Acids Res 1992, 20(17): 4499-4505; Kramer et al., J. Bacteriol. 1988, 170(5): 2344-2351). Such naturally occurring modifications can also be detected by the inventive method, e.g. by detecting base mismatches with these modified nucleobases, or altered base pairing behaviour, directly or by a further (second) modification of these naturally modified nucleobases. Some natural modifications may be the result of a stress response or other environmental influences. Thereby, the inventive method can be used to detect such responses of a cells and influences in a cell. An example is a $s^4U$ modification, especially in tRNA, in response to UV light, especially near-UV irradiation (Kramer et al., supra). $s^4U$ modification, especially in tRNA, may also be used to measure growth rate of cells (Emilsson et al., supra). This modification, to be used as growth indicator, may be detected according to the inventive method. Preferably, eubacteria or archaea are used for such natural modification.

In preferred embodiments of the invention the step of modification is performed by incorporation of a thiol modified nucleobase into the PNA (first part of modification) and alkylating said thiol nucleobase with an alkylating agent (second part of modification). Thiol-reactive alkylating agents include iodoacetamides, maleimides, benzylic halides and bromomethylketones. Alkylating agents may comprise an alkyl group as mentioned above and a leaving group, such as halogenide, e.g. Br or Cl. The agents react by S-alkylation of thiols to generate stable thioether products. Arylating reagents such as NBD (4-nitrobenzo-2oxa-1,3-diazole) halides react with thiols or amines by a similar substitution of the aromatic halide by the nucleophile. Also available are thiosulfates for reversible thiol modification. Thiosulfates react stoichiometrically with thiols to form mixed disulfides. Thiols also react with isothiocyanates and succinimidyl esters. Isothiocyanates and succinimidyl esters may also be used to react with amines.

Modifications of a thiol may also comprise a step of converting the thiol to a thioketone. The thioketone group may then be further modified by addition or removal of a hydrogen bonding partner. The conversion to a thioketone may comprise a removal of hydrogen, such as on a transition metal cluster as catalyst as described in Kohler et al. (Angew. Chem. Int. Ed. Engl. 1996, 35(9): 993-995). The conversion to a thioketone allows additional options for reaction chemistry to perform the inventive modification. Kohler et al. also describe the introduction of a thiol or thioketone to an aryl, which is also an option for the present invention to create a thiomodification (thiol, thioketone) in the inventive modified nucleobase.

Alkylation of the thiol is also referred to as thiol(SH)-linked alkylation. The benefit of thiol alkylation is its selectivity for the "soft" thiol whereas non-thiolated nucleobases can remain unchanged (HSAB theory—"hard and soft (Lewis) acids and bases", Pearson et al., JACS 1963, 85(22): 3533-3539). Iodoacetamides readily react with all thiols to form thioethers; they are somewhat more reactive than bromoacetamides, which may also be used. Maleimides are excellent reagents for thiolselective modification, quantitation and analysis. In this reaction, the thiol is added across the double bond of the maleimide to yield a thioether. An alkylation is also possible via the above mentioned thioketone.

Preferably, the modification comprises alkylating on position 4 of a uridine. At this position an interference with the natural hydrogen binding behaviour of uridine is very effective. Such a modification can be with an alkylating agent, e.g. an alkylating agent that comprises the hydrogen bonding partner, preferably a hydrogen bond acceptor, or an alkylating agent that does not comprise a hydrogen binding partner—and thereby block hydrogen bonding that would normally happen at position 4 of uridine. Such an alkylation can be performed in a two-step modification via a 4-thiouridine as mentioned above.

Another preferred alkylation is at position 6 of a guanosine. Such an alkylation increases mispairing rate from the standard GC pair to a G*A wobble pair with only 2 effective hydrogen bonds (instead of 3 in GC). In particular preferred embodiments, introduction of alkylation at position 6 of guanidine comprises the modification of guanidine to 6-thioguanosine ($s^6G$) and alkylating the thio-position. Thus, this is a further preferred example of such an alkylation in a two-step modification via a 6-thioguanosine as mentioned above. 6-thioguanosine can be incorporated into a PNA by biosynthesis in the presence of 6-thioguanosine nucleotides.

Preferred alkylating agents have the formula Hal-(C)$_x$O$_y$N$_z$ (hydrogens not shown), with Hal meaning halogen, C carbon chain of x C atoms, branched or unbranched, with x being 1 to 8, O meaning y oxygen substituents to a C atom with y being 0 to 3, N meaning z nitrogen substituents to a C atom with z being 0 to 3. N is preferably at least one —NH$_2$ or double bonded =NH, O being preferably a —OH or double bonded =O. Hal is preferably selected from Br or I.

In particular preferred, the PNA comprises one or more 4-thiouridine or 6-thioguanosine, preferably 2, 3, 4, 5, 6, 7, 8, 9, 10 or more 4-thiouridine or 6-thioguanosine. Modifying one or more nucleobases may comprise attaching a hydrogen bonding partner, such as a hydrogen bonding acceptor or donor, to the thiol modified nucleobase. Such an attachment can be done by any chemical modification, with alkylation being preferred, such as by a halide containing alkylating agent as mentioned above.

An alternative to alkylation is modification by oxidation. Such a modification is for example disclosed in Burton, Biochem J 204 (1967): 686 and Riml et al., Angew Chem Int Ed Engl. 2017; 56(43):13479-13483. For example, a nucleobase, especially a thiolated nucleobase, can be modified by oxidation to alter a hydrogen-bonding donor or acceptor. In case of a two-step method via thiolated nucleobase as described above, the sulphur of the thiol group can be oxidized, such as by OsO$_4$, NaIO$_3$, NaIO$_4$, or a peroxide such as chloroperoxy-benzoic acid or H$_2$O$_2$. For example, a s4U can be oxidized into a C (Schofield et al., Nature Methods, doi:10.1038/nMeth.4582), which alters base pairing/hybridization behaviour from U-A to C-G. As shown by Burton (supra), said oxidation does not require the thiol intermediary, however, said thiol intermediary is preferred, especially in case of biosynthesis modification (see below). Such C analogues are for example trifluoroethylated cytidine (e.g. product of oxidation in the presence of 2,2,2-trifluoroethylamine). The C analogues may retain cytosine's base pairing behaviour and/or the pyrimidin-2-one ring. The 4 position on the pyrimidin-2-one ring may be substituted, such as by an amino group (as in C) or comprise other substituents such as an R—NH-group with R being selected from an alkyl group, an aromatic group, an alkane group, NH$_2$, trifluoroethylene, MeC, etc. (see Schofield et al., supra, especially supplementary FIG. 1; incorporated herein by reference).

In a preferment, a modified nucleobase, e.g. a thiol modified base, is incorporated into the PNA through biosynthesis in a cell or by cellular enzymes (e.g. by in vitro transcription). Also, a chemical introduction of the modified nucleobase is possible, e.g. by (non-biological) chemical PNA synthesis, such as organic or semisynthetic synthesis. Biosynthesis is the synthesis of a PNA based on a template PNA (usually DNA, in particular genomic DNA) and a template dependent synthesis (transcription, reverse transcription). Suitable enzymes for such transcription are RNA polymerases, DNA polymerases, reverse transcriptases. The enzyme can incorporate natural and modified nucleotides (with the modified nucleobase) into the biosynthesized PNA molecule. Nucleotide monomer units are connected when forming the PNA. Such monomers can be provided in modified form and incorporated into the PNA. Preferably, only one natural nucleotide type (A, G, C, T/U) is modified, i.e. has modified (non-natural) counterparts that are incorporated into the PNA. Also preferred, all natural nucleotide types are present with the modified nucleobase(s) being fewer in number than the corresponding natural (non-modified) nucleobase. "Corresponding" means the natural nucleobase with the least atom (not counting hydrogen) changes being necessary to restore the natural nucleobase. E.g. A, G, C, T/U are provided in addition modified U (or any other modified nucleotide type selected from A, G, C, T). Preferably the ratio of modified nucleotides to non-modified (natural) nucleotides of a given type is 20% or less, e.g. 15% or less or 10% or less or even 5% or less (all molar-%). The modified nucleotide will be incorporated instead of the corresponding natural nucleotide but will then later in the inventive method cause atypical base pairing (changed base pairing behaviour as detailed above), which in turn will lead to another complementary nucleotide base pairing to the modified nucleotide than as it would to the natural counterpart nucleotide. Hence a change in sequence of a hybridized complementary strand, e.g. a newly synthesized complementary strand, will emerge. So, base pairing to at least one modified nucleobase may lead to base pairing with another nucleotide than base pairing with a nucleobase that has not been modified, with said nucleobases being otherwise the same.

It is also possible to incorporate alkylated nucleobases into the PNA via biosynthesis, e.g. alkylated nucleobases as described above but without using a thiol intermediary. For example, alkylated nucleotides can be incorporated into cells and used by said cells during PNA synthesis. Such methods have been described by Jao et al., Proc. Nat. Acad. Sci. USA 105 (41), 2008:15779 and Darzynkiewicz et al. Cytometry A 79A, 2011:328. In particular, an effective modified nucleotide to be used according to the invention is 5-ethynyl-uridine (5-EU). Ethynyl-labelled uridine is cell permeable and incorporates into nascent RNA instead of its natural analogue uridine. In preferred embodiments, the resulting ethynyl-functionalized PNA is further modified, such as via Cu(I)-catalyzed click chemistry (e.g. as described in Presolski et al., Current Protocols in Chemical Biology 3, 2011:153; or Hong et al. Angew. Chem. Int. Ed. 48, 2011:9879) to introduce additional functionalized groups via azide-functionalized molecules, e.g., NHS ester, maleimides, azido-acids, azido-amines, to influence the hydrogen bonding capability of the ketone in ortho position to the ethynyl-group.

In other embodiments, such azide-functionalized molecules can be introduced into the cells themselves to be biosynthesized into PNA molecules as modified nucleobases. The resulting azide-functionalized PNA can subsequently be detected via Cu(I)-catalyzed (CuAAC) or Cu(I)-free strain promoted (SPAAC) Click Chemistry to introduce a functional group which alters the hydrogen bonding capabilities of the nucleobase as compared to the unmodified nucleobase (C, T/U, A, G).

A further example of modifying one or more nucleobases of the PNA includes incorporation of vinyl-functionalized nucleobases into the PNA, such as 5-vinyl-uridine. Vinyl groups can be further modified to alter hydrogen bonding capabilities of the otherwise unmodified nucleobase (see Rieder et al. Angew. Chem. Int. Ed. 53, 2014:9168).

In particular preferred embodiments, modifying one or more nucleobases of the PNA comprises cyclization of an allyl group and/or comprises halogenization, especially iodination, of a nucleobase of the PNA. The modified nucleobase is preferably an allyl nucleobase, such as N$^6$-allyladenosine ("a$^6$A"), which can be further modified by cyclization involving the allyl group. Such an allyl nucleobase can be incorporated into the PNA during PNA synthesis, especially in a cell as described for other embodiments herein. Halogenization and/or cyclization may follow the principles described in Shu et al., J. Am. Chem. Soc., 2017, 139 (48): 17213-17216. Preferably the method comprises an incorporation of $N^6$-allyladenosine in a cell followed by iodination with elemental iodine ($I_2$), for example, which leads to cyclization of the iodized former allyl group, e.g. with a nitrogen on the purine (in case of modified A or G) or pyrimidine (in case of modified C or T/U) group of the nucleobase. Said modification leads to altered base pairing, which can be read during sequencing or hybridization. E.g. $a^6A$ behaves like A and can be metabolically incorporated into newly synthesized RNAs inside mammalian cells. The iodination of $N^6$-allyl group of $a^6A$ under mild buffer conditions spontaneously induces the formation of $N^1,N^6$-cyclized adenosine and creates mutations at its opposite site during complementary DNA synthesis of reverse transcription.

In a further preferred embodiment, modifying one or more nucleobases of the PNA comprises introduction of a 5-Bromo-uridine (5-BrU) nucleobase into the PNA. 5-BrU is a mutagen that is present as tautomer which means that it is present in its keto- and enol-form which base-pairs to either Adenine or Guanine (see FIG. 37a), which in turn leads to an increase of T>C conversions (as compared to not-modified U) in an amplification reaction like PCR. Thus, in this and general preferred embodiments of the invention, modifying one or more nucleobases of the PNA introduces a tautomeric nucleobase, which tautomeric forms can base pairs with both purine bases (A and G) in case of modified T/U and modified C or can base pair with both pyrimidine bases (T and C) in case of modified A and G. Base pairing with both purine/pyrimidine bases means here a more equalized (but not necessarily equal) base pairing behaviour than in case of non-modified A, G, U/T, C (which rarely pair with the non-complementary base). In other words, the tautomeric base has increased base pairing with the non-complementary base of the same base core structure (purine or pyrimidine) than the unmodified base (wobble behaviour). Said increase is at standard conditions, especially for PCR.

Such wobble behaviour can be determined by an increased result of mixed bases at a particular position corresponding to the modified nucleobase. Wobble base detection is a preferred read-out of the inventive method in any embodiment (compare FIGS. 5B, 24B, 37C).

In further related embodiments, 5-BrU or any other halogenated nucleobase can be further modified by substitution of the halogen by an amino group. For example, 5-BrU can be heated with ammonia to convert it into 5-aminouridine. Such an amino-modified nucleobase changes base pairing during reverse transcription and/or will introduce additional wobble behaviour.

The PNA (with the modified nucleobase) may comprise or consist of RNA or DNA. Example RNA is mRNA, microRNA (miRNA or miR), short hairpin RNA (shRNA), small interfering RNA (siRNA), PIWI-interacting RNA (piRNA), ribosomal RNA (rRNA), tRNA-derived small RNA (tsRNA), transfer RNA (tRNA), small nucleolar RNA (snoRNA), small nuclear RNA (snRNA), long non-coding RNA (lncRNA), or precursor RNA molecules thereof. DNA is for example genomic DNA, cDNA, plasmidic DNA or a DNA vector. The PNA can be in a duplex or a single strand.

"Comprise" relates to an open-ended term and may also allow molecules to contain other members, e.g. other types of nucleotides (RNA or DNA, including artificially modified nucleotides such as LNA, may exist). "Consist of" is regarded as a closed definition requiring members to adhere to the requirement, i.e. complete RNA or complete DNA.

Preferably, for each nucleotide type selected from A, G, C, U or T the modified PNA comprises more natural nucleotides than modified nucleotides. Here, PNA relates to the final PNA with all modifications according to the invention. The PNA preferably comprises 1, 2, 3, 4, 5, 6, 7, 8, 9, 10 or more and up to 30 modified nucleotides. Preferably, few nucleobases are modified, such as 20% or less, e.g. 15% or less or 10% or less or even 5% or less (all molar-%) nucleobases in the PNA molecule are modified.

The PNA molecule may have any length. Preferably it has a length of at least 10 nt (nucleotides). Especially preferred is a length of 10 nt, 20 nt, 30 nt, 40 nt, 50 nt, 75 nt, 100 nt, 250 nt, 500 nt, 1000 nt, 2500 nt, 5000 nt, 10000 nt, 25000 nt, 50000 nt, 100000 nt or more nt in length or any range in between these values. Preferred ranges are of 10 nt to 100000 nt or of 50 nt to 50000 nt in length.

Preferably the PNA is from a particular cellular fraction of nucleotides, such as a total RNA fraction, a mRNA fraction or a DNA fraction, such as plasmid DNA or genomic DNA. Fractions can be selected by isolating PNA with a common characteristic, such as length, nucleotide type or sequences, such as a poly(A)-tail or a 5'-cap in mRNA.

The inventive method contains the step of base pairing the PNA by a complementary nucleic acid. In said base pairing, at least one of the modified nucleobases should be base paired (usually by base pairing several nucleobases of the PNA). Base pairing with the complementary nucleic acid can be facilitated by hybridizing the PNA with a nucleic acid strand. This may also occur during extension reaction, e.g. PCR, or by hybridizing probe nucleic acids. The complementary nucleic acid may have any length, for example those lengths disclosed above for PNA.

The sequence of the complementary nucleic acid is identified at least at the position that is complementary to at least one modified nucleobase. Sequence determination can be done by any common procedure known in the art. Such methods include methods based on generating complementary strands, e.g. by PCR, completely or in part such as in next generation sequencing (NGS), a fragment based sequencing method. If desired, fragment reads can be assembled to a combined sequence. However, for the inventive uses, this not necessary as long as the complementary nucleobase to the modified nucleobase is identified, in particular with its neighbouring sequence (such as neighbours in +/−5 nt, +/−10 nt, +/−15 nt or +/−20 nt). Further methods to determine a sequence include binding to a probe, whereby through the known hybridizing probe sequence the sequence of the PNA is determined as complementary sequence.

Another option is small nucleic acid sequencing, especially if the complementary nucleic acid is small, such as in case of complementary nucleic acids to miRNA, shRNA, siRNA. Small nucleic acids may be in the length range of e.g. 10 nt to 200 nt, preferably 12 nt to 100 nt or 14 nt to 50 nt. Longer lengths than 200 nt or shorter lengths than 10 nt are also possible. The fragments of the complementary nucleic acids may have such a length on average. Fragments can be generated by physical or chemical means as known in the art for NGS. In case of small nucleic acids, including fragments such as obtained during NGS, it is preferred to ligate adaptors to the nucleic acids which may be used as hybridisation sequences for primers or probes. Such adaptors may also contain characteristic sequences, like barcodes, to identify the small nucleic acid by a label. Barcodes may provide a label for the origin of the sample from which the PNA was obtained or of the PNA molecule or its complementary nucleic acid that was fragment (fragment origin). Such barcodes may be useful in multiplexed sequencing, wherein many nucleic acids of different sequence, such a plurality of different complementary nucleic acids and/or a plurality of fragments of one or more complementary nucleic acids are sequenced. Such a plurality may e.g. be 2 to 1000 nucleic acids or more. Another possibility, that does not necessarily require adaptors, is by hybridising primers or probes to the complementary nucleic acid sequence that corresponds to the PNA. Such primers or probes may be hybridized to known sequences or randomly, e.g. by using random primers. Random primers are described below with regard to the inventive kit and any such random primer may be used in the inventive method.

In a preferred embodiment of the invention, the PNA of a single cell is identified according to the invention. Accordingly, the PNA of a cell is isolated and kept separate from PNA of other cells. "Keeping PNA separate" means that the PNA of the cell under investigation remains identifiable without mixing PNA sequencing information of the cell under investigation with the sequencing information of other cells. This can be achieved by physically separating the PNA or by labelling, especially by labelling the PNA or the complementary nucleic acids with a label, e.g. by a barcode, that identifies the cell of interest. This allows the analysis of a PNA metabolism of single cells. Single cells analysis can be performed by single cell sequencing methods (Eberwine et al. Nat. Methods. 11 (1): 25-27). Alternative to sequencing, it is also possible to prepare the complementary nucleic acids or their fragments, preferably but not necessarily with adapters, in a library. The library may then be independently sequenced or provided for other uses.

The inventive modification, such as thiol-specific alkylation, prompts the quantitative "mis-"incorporation of complementary nucleotides, which now form different hydrogen bond patterns as described above. E.g. guanosine can be incorporated instead of adenosine across the modified nucleobase (e.g. alkylated 4-thiouridine) complementary nucleic acid binding, such as during transcription or reverse transcription. Still, (reverse) transcriptase-processivity is usually unaffected since the alternatively base paired nucleotide can be amplificated together with its PNA without further hindrance. Preferred are combinations with a second modification after a first enzymatic modification (such as by incorporating modified nucleobases). Such a combination with well-established and non-toxic $s^4U$ metabolic labeling protocols as mentioned above.

The inventive sequencing method that leads to a sequence change in the complementary nucleic acid due to the modified nucleobase can be coupled to available high-throughput sequencing methods, such as NGS. Sequence changes, in particular if incomplete or partial, differing between different individual molecules of PNA/complementary nucleic acids can be identified by available computational methods. E.g. T>C conversions (due to U modifications that lead to increased G base pairing) can be tracked in next-generation sequencing datasets. Such highly automated methods, in combination with computerized analysis, allows the invention to provide rapid access to intracellular RNA processing kinetics, a preferred application of the invention. The invention can accurately report the RNA polymerase II-dependent transcriptional output due to complementary base pairing. Insights into the intracellular kinetics of RNA biogenesis, processing and turnover is essential to unravel the molecular basis for changes in gene expression patterns that impinge on essentially any given biological process in life.

Accordingly, in a preferment, the inventive method can be used to determine modifications or easily modified alterations of PNAs in cells. Such "easily modified alterations" e.g. relate to the above described multi-step method, wherein a first modification (also termed alteration) is performed in a cell and a later modification is done in a second or further step, usually outside a cell after isolation of the PNA.

Preferably, the inventive method is used to modify RNA (as PNA) with at least a first modification/alteration performed in a cell, in particular in living cell. This allows tracking of RNA expression changes since expressed RNA is modified.

The regulated expression of genetic information is essential to maintain cellular homeostasis, provides cellular flexibility to respond to altering environmental conditions, and—if dysregulated—contributes to human diseases such as cancer. Underlying these essential biological processes are tightly regulated molecular events that control the relative kinetics of RNA transcription, processing, and degradation in a transcript-specific manner.

The cellular RNA pool, encompassing a myriad of RNA species—including mRNA or non-coding RNAs, such as microRNAs—is defined by the transcription of selected loci in the genome, and can be qualitatively and quantitatively assessed by RNA profiling techniques, such as high-throughput sequencing. However, the abundance measurement of steady-state RNA levels does not accurately mirror transcriptional activity per se. In fact, RNA stability plays a major role in determining the relative abundance of any given RNA molecule. Approaches to measure transcription and RNA decay rates at the genomic scale are therefore useful to unravel insights into the dynamics of RNA expression and its underlying regulatory mechanisms. According to the invention, it is possible to determine the intracellular kinetics of RNA biogenesis and turnover.

RNA can be altered or modified by a cell's own metabolism, e.g. by incorporating altered or modified nucleotides into naturally processed RNA. Such alterations can be used to selectively introduce the inventive modifications that (alone or after a further modification) change hydrogen bonding behaviour. Due to the metabolic influence, such a method is referred to as "metabolic sequencing"—in case the modified nucleotide is then sequenced. The sequencing step or generally any base pairing step to a complementary (poly)nucleotide can be automated and processed in a high-throughput sequencing method as mentioned above. The invention provides a high-throughput-compatible metabolic labelling protocol that is suitable to determine the intracellular kinetics of RNA biogenesis and turnover. It accurately measures RNA polymerase II-dependent poly-adenylated transcriptional output, and recapitulates global post-transcriptional gene regulatory signatures, thus solving the problem of providing RNA expression kinetics (including biogenesis and turnover) in a cell at high temporal resolution.

The cell can be any cell, such as a bacterial cell, including eukaryotic and procariotic cells, gram negative and gram-positive cells, fungal cells, algae cells, plant cells, animal cells, mammalian cells, such as rodent cells, primate cells, human cells, non-human cells, archaebacterial cells, avian cells, amphibian cells, such as frog cells, reptilian cells, marsupial cells.

It is possible to monitor changes by temporal control of the modification, e.g. a phase of cell RNA expression without modification is compared with phase of cell RNA expression with modification. Such phases are preferably compared in the same cell or cell culture. E.g. a phase with modification is followed by a phase without modification or vice versa. Accordingly, in a preferment of the invention, one or more cells are cultured in at least two culturing phases, wherein one culturing phase comprises incorporation of a modified nucleotide into biosynthesized RNA, which is modified by addition or removal of a hydrogen bonding partner; and another culturing phase that lacks such incorporation of the modified nucleotide into biosynthesized RNA. It is also possible that the "another culturing phase" comprises incorporation of a modified nucleotide into biosynthesized RNA but at a different, e.g. lower, concentration as in the other one culturing phase. The different or lower concentration as in the other one phase should be sufficient to observe a difference (in particular different concentration) in the incorporation of modified nucleotides into biosynthesized RNA. The inventive method can be accordingly defined as a method of identifying a polynucleic acid (PNA) comprising the steps of expressing a PNA in cell; modifying one or more nucleobases of the PNA; isolating the PNA from the cell; optionally further modifying the PNA; wherein the modification(s) before or after the isolation or together add or remove a hydrogen bonding partner of one or more nucleobase, thereby altering the base pairing capacity of the one or more nucleobases; base pairing a complementary nucleic acid to the PNA, including base pairing to at least one modified nucleobase; identifying the sequence of the complementary nucleic acid at least at the position that is complementary to at least one modified nucleobase. A particular preferred metabolic-labeling (i.e. modification by a cells metabolism, such as by its enzymes like RNA polymerases) is by 4-thiouridine-incorporation events. This can be used to change the base pairing behavior of U.

In particular preferred is the method in at least two culturing phases of cells, wherein in at least two culturing phases different levels of PNA modification, in particular RNA modification, are facilitated. This can be achieved by providing the cell with different concentrations of the modified nucleobase, thereby allowing the cell to incorporate the modified nucleobase at different levels or concentrations into PNA, especially RNA. As above, preferably the modified nucleobase is a thiol modified nucleobase. The level of PNA modification in one phase may be no modification. The phases, especially those with PNA modification should have a pre-set time period for said PNA modification. By comparing the incorporation between the different phases, it is possible to calculate a turnover rate in the pre-set time period. In a particular preferred embodiment, a turnover or degradation rate is calculated based on the incorporation of modified nucleobase into PNA in at least one phase in comparison to the other phase. Preferably, the phases are consecutive cultivation phases.

A further comparison can be between cultivation phases of different cells. Such a comparison allows an estimate of differential expression and PNA turnover between these cells. One of the cells or group of cells may be a control and another cell or another group of cells may be candidate cell or group of cells under investigation. Both cells or group of cells may have a phase of incorporation of modified nucleobases into PNA, which is compared. Preferably such a phase of incorporation is controlled by providing the cells with modified nucleobases for incorporation into PNA. Preferably the same amounts of modified nucleobases are provided to each cell or to each group of cells, suitable for comparison of cell metabolism. Preferably a phase of incorporation is followed by a phase of no further incorporation, e.g. by ceasing to supply the cell or group of cells with further modified nucleobases. It is also possible that a phase of incorporation is followed by a phase of reduced incorporation or by incorporation at different levels. Any change in levels of incorporation of modified nucleobases into PNA is followed by an adaption of the cell's metabolism, which may be monitored by the inventive method. E.g. if a phase of incorporation is followed by a phase of lower or no incorporation, then it is possible to monitor degradation of modified PNA. If a phase of no or limited incorporation is followed by a phase of incorporation or higher then limited incorporation, then it is possible to monitor build-up of modified PNA.

Accordingly, one use of the inventive method is in comparing identified sequences of the complementary nucleic acid at least at the position that is complementary to at least one modified nucleobase (as described above) in at least two cells or in at least two different growth phases in a cell, wherein said at least two cells or growth phases have differential expression (usually gene expression, including mRNA or regulatory RNA expression) between said at least two cells or said growth phases. Said differential (gene) expression can be caused by inhibition or stimulation of at least one gene in a cell. Such a method can be used to screen for differential expression effects of a certain perturbation in cellular metabolism. Said differential expression may be of an unknown gene, such as in a screening method, wherein regulatory inhibitors or activators or any other substances with a phenotypical effect are investigated for particular genetic effects in a cell. In other embodiments of this method, the target gene may be known and further secondary effects on gene expression of other genes is investigated. For example, the known gene can be a known regulatory gene, such as an oncogene or a tumor suppressor gene.

The cell or group of cells may be in a culture in vitro or in a living organism, such as a plant, bacterial cell, fungal cell, algae cell, non-human animal or human, in vivo. It case of in vivo cells, the modified nucleobases may be supplied to the cell by administering the modified nucleobases to the organism, e.g. systemically like into a vascular system or topically to an organ of interest of the organism. Accordingly, it is possible to monitor metabolism of PNA in vivo, or in a particular organ of interest. The PNA may then be isolated from the organism, such as by a biopsy or, in case of secreted PNA, from a body fluid sample, or by sacrificing a non-human organism. Preferably PNA of single cells from the organism is isolated and analyzed according to the inventive method, e.g. by labelling and/or library generation and/or by single cell sequencing as mentioned above. Any description of culturing phases also applies to treatment in vivo and is referred to as "growth phase". "Growth phases" do not require growth of cells or multiplication of cells but refer to the PNA metabolism or "growth" that is identified and analyzed.

Comparison of different levels of PNAs and PNA turnover is important to elucidate differences in cell metabolism between different states cells are in during an organism's development and disease. To be able to measure turn overrate of PNAs can help elucidate which pathways are active and which are less active or inactive. In that respect the turnover rate provides for an additional measure to the steady state concentration measurement of PNA, in particular RNA, measuring just the concentration of PNA, such as mRNA present in a cell or tissue or organ.

Preferably the biosynthesized PNA, preferably RNA, of the two culturing phases are collected from said cells, preferably also mixed, and wherein base pairing a complementary nucleic acid to the PNA comprises generation of complementary polynucleic acid strands, preferably DNA strands, by transcription, such as reverse transcription in case of RNA as PNAs.

It is a particular benefit of the invention that the PNA created with modification and comparable PNA without or less modification, or the respective complementary nucleic acids need no separation. The base pairing of the PNA with the complementary nucleic acids can be in mixture—of both modified PNA and non-modified PNA. The sequence of the PNA/complementary nucleic acids can then be determined in combination because the sequence/identity of the complementary nucleic acids can be determined in both cases (with and without modification) and by comparison the modification events can be inferred. Such comparison is preferably a computerized sequence comparison. The inventive method, especially preferred according to its embodiment of base pairing to at least one modified nucleobase that leads to base pairing with another nucleotide than base pairing with a nucleobase that has not been modified, further comprises determining the sequence of the complementary polynucleic acid strands and comparing the strand sequences, wherein an altered complementary nucleic acid as a result of the modification by addition or removal of a hydrogen bonding partner can be identified by comparison with the complementary nucleic acid without modification. Preferably the sequences of nucleotides are determined as fragments, such as used in NGS and high throughput sequencing. Sequences to be determined (which many harbour the position that is complementary to the at least one modified nucleobase) may have a length of 10 nt to 500 nt, preferably of 12 nt to 250 nt or of 15 nt to 100 nt.

Computerized identification of the sequence of the complementary nucleic acid at least at the position that is complementary to at least one modified nucleobase may comprise a comparison with a sequence of a non-modified PNA. Such comparative sequences may be obtained from sequence databases such as at EBI or at NCBI or determined by PNA generation without introducing a modification, such as by natural bases base pairing to natural complementary bases. A computer program product for such comparison or a computer readable medium for the method can be included in the inventive kit.

The invention further provides a kit suitable for performing a method of the invention comprising a thiol modified nucleobase and an alkylating agent suitable for alkylating the thiol modified nucleobase at the thiol group, wherein the alkylating agent comprises a hydrogen bonding donor or acceptor, preferably wherein the alkylating agent is any one mentioned above, especially preferred iodoacetamide. However, any of the above described alkylating agents, agents suitable for any of the above modifications, in particular modified nucleotides with the modified base, such as thiol modified nucleotides can be included in the inventive kit.

The kit preferably further comprises primers, nucleotides selected from A, G, C, and T, a reverse transcriptase or a combination thereof, preferably all these components. Example primers are random primers, which are mixtures of randomly selected primers. Such a random primer mixture may have at least 50 or at least 100, at least 500 different primers. Random primer may contain random hexamers, random pentamers, random pentamers random octamers, etc.

The kit may further comprise a PNA polymerase and preferably further a buffer for polymerization of the polymerase. The polymerase may be DNA or RNA polymerase.

The inventive kit may also comprise adaptor nucleic acids. Such adaptors may be ligated to nucleic acids to generate adaptor bound complementary nucleic acids as described above. The adaptors may comprise one or more barcodes as described above. The kit may also comprise a ligase, such as a DNA ligase.

The components of the kit may be provided in suitable containers, such as vials or flasks.

The kit may also comprise instructions or a manual for performing any of the inventive method.

The present invention is further described by the following figures and examples, without necessarily being limited to these aspects of the invention.

BRIEF DESCRIPTION OF THE DRAWINGS

FIG. 18. 4-thiouridine metabolic labeling in Drosophila S2 cells. Quantification of s$^4$U-incorporation into total RNA after s$^4$U-metabolic labeling for the indicated time in a pulse labeling experiment in Drosophila S2 cells. Substitution rate of s$^4$U compared to unmodified uridine determined by HPLC is shown and was determined as previously described (Spitzer et al. (2014) Meth Enzymol 539, 113-161). Values represent mean±SD of three independent replicates. Maximum incorporation rates after 24 h labeling are indicated.

FIG. 20. Frequency of $s^4U$-incorporation in metabolically labeled small RNAs. Tukey boxplots show the fraction of T>C conversion reads containing one, two, or three T>C mutations for each of 71 abundantly expressed (>100 ppm) miRNAs in small RNA libraries prepared from size selected total RNA of Drosophila S2 cells subjected to $s^4U$ metabolic labeling for 24 h. The median fraction of T>C conversion reads is indicated.

FIG. 22. Precursor-miRNA tailing counteracts efficient miRNA biogenesis. Correlation between pre-miRNA uridylation and T>C mutation rates in SLAM-seq small RNA libraries prepared from ago2$^{ko}$ S2 cells after treatment with $s^4U$ for the indicated time. Pearson's correlation coefficient ($r_p$) and associated p-Value are shown.

GSEA of MYC-target signature in cell lines from (I) or AML patients with high or low MYC expression. (L) MYC-target signature expression across 5583 patient samples separated based on high or low MYC expression and cancer type. ****, p<0.0001 (Wilcoxon's rank-sum test).

Figure 29:
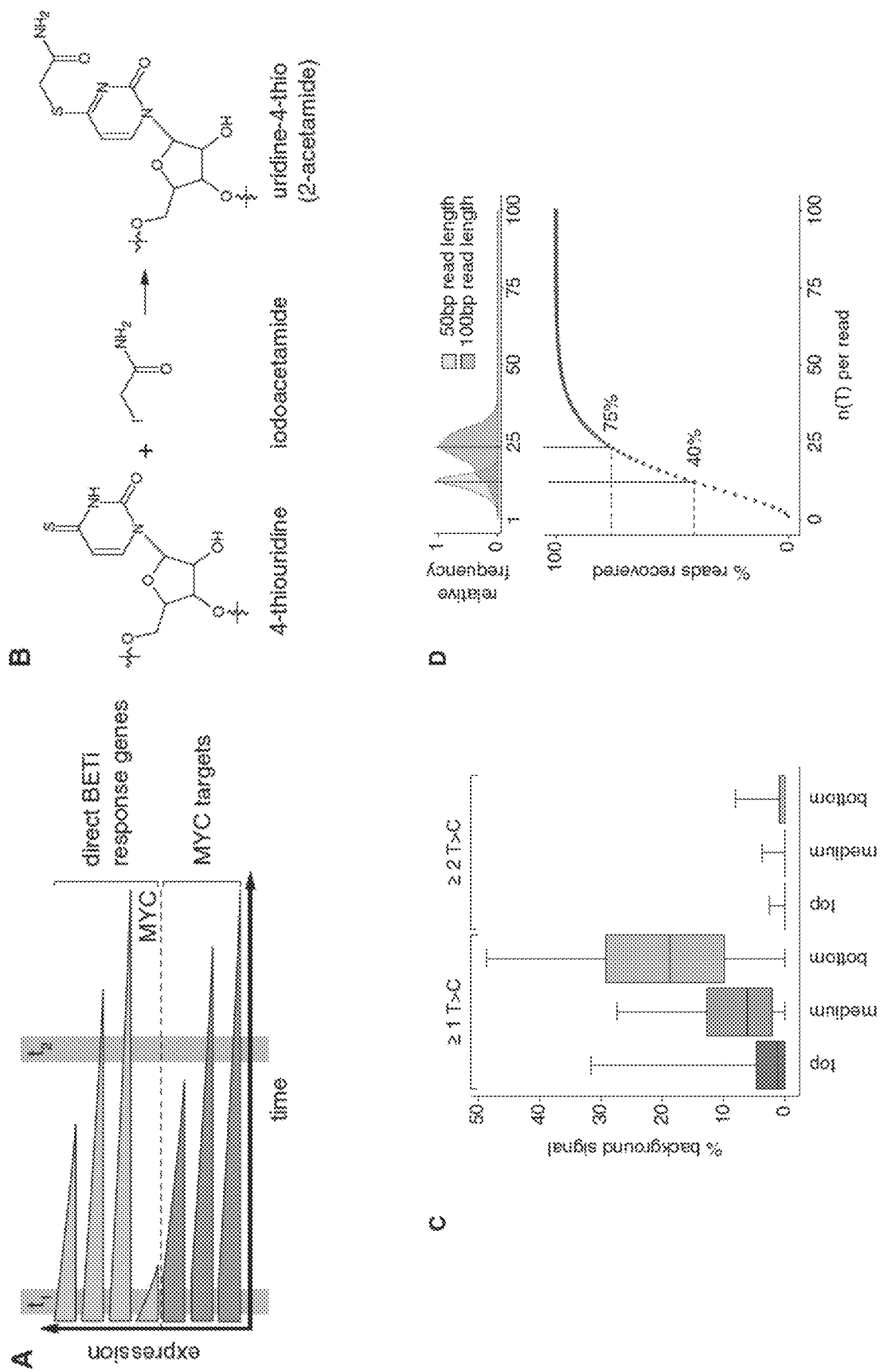
Figure 29:
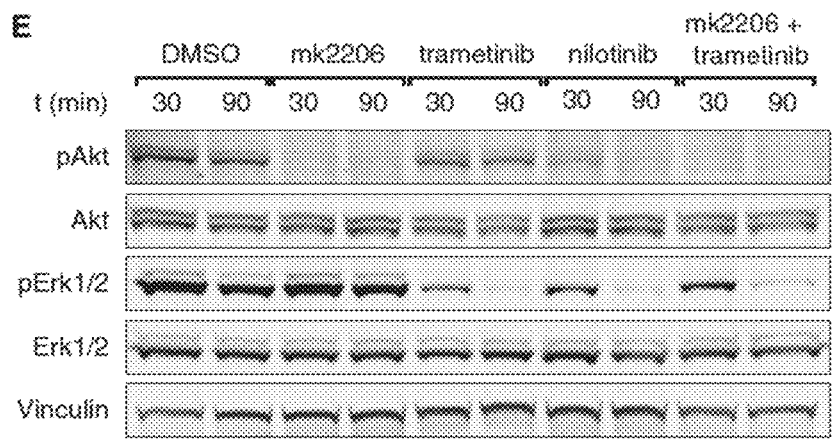

FIG. 29. Experimental setup of SLAM-seq for mapping differential gene expression. (A) Schematic of a targeted perturbation and its primary and secondary effects on mRNA levels for genes with different turnover rates, exemplified by BETi treatment and indirect suppression of MYC target genes. (B) Alkylation of a 4-thiouridine residue in mRNA by iodoacetamide. (C) Contribution of background error rates to reads with ≥1 or 2 T>C conversions in a SLAM-seq experiment with 60' labeling time. Background signal was measured by parallel alkylation and sequencing of mRNA from $s^4U$ treated and untreated cells. Boxplots show error rates for genes with high (top 10%) medium (45-55%) and low (bottom 10%) mRNA turnover estimated from the fraction of labeled reads in $s^4U$ treated libraries. Whiskers indicate 5-95% range. (D) Recovery of newly synthesized mRNA by SLAM-seq as a function of T-content per read. Estimations are based on a labeling efficiency of 11.4% per T in newly synthesized mRNA. Top histograms show T-content of 3'UTR reads for different read lengths. (E) Validation of MAPK and AKT pathway inhibition in K562 cells treated with indicated kinase inhibitors for SLAM-seq samples shown in FIG. 25E.

Figure 30:
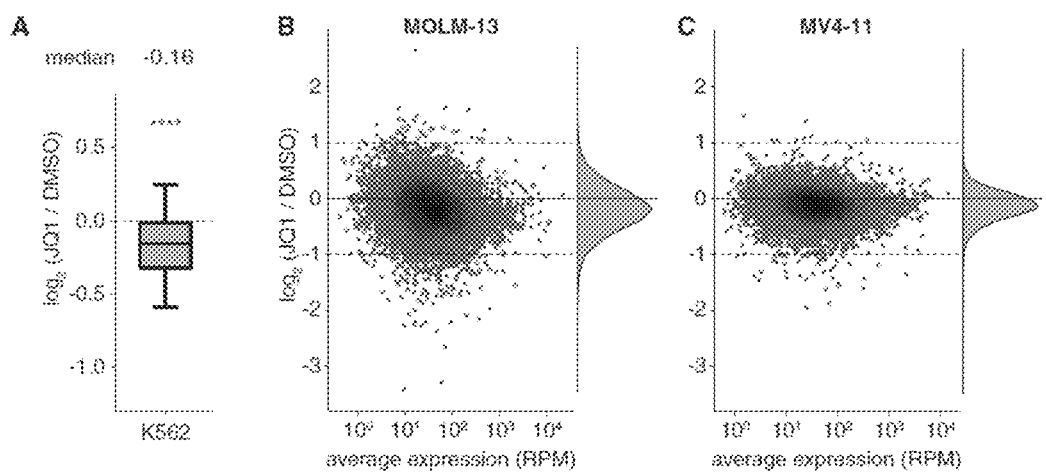
Figure 30:
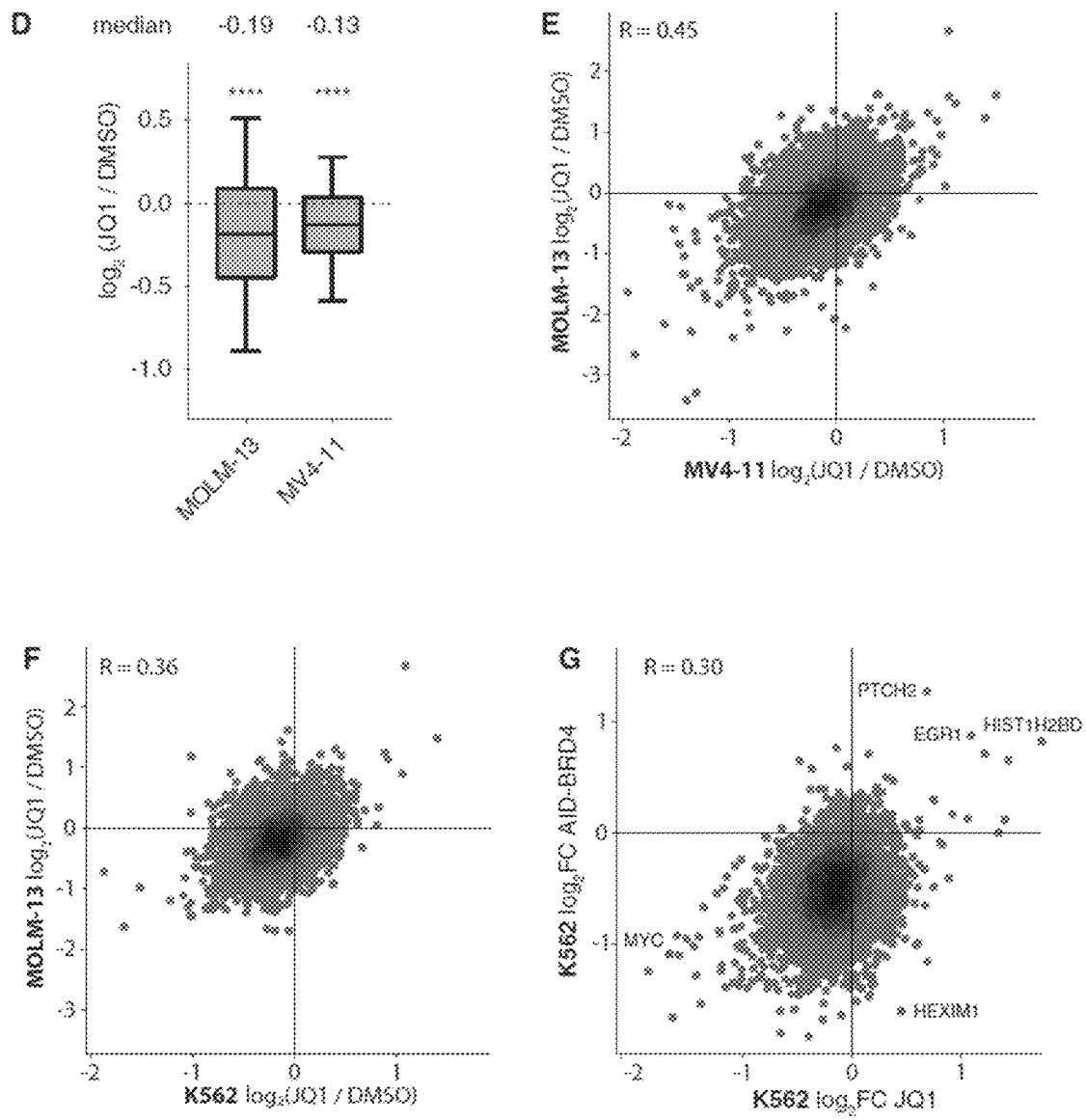

FIG. 30. Direct JQ1 responses in myeloid leukemia cell lines. (A) Boxplot summarizing global gene expression changes measured by SLAM-seq for K562 cells treated with JQ1 in FIG. 26D. (B, C) Primary response to JQ1 treatment mapped by SLAM-seq as in FIG. 2D for cell lines MOLM-13 and MV4-11. (D) Summary of global gene expression changes upon JQ1 treatment for MOLM-13 and MV4-11 cells as in (A). (E, F) Pairwise comparison of gene expression changes upon JQ1 treatment for indicated cell lines. (G) Comparison of SLAM-seq responses to JQ1 and acute BRD4 degradation in K562 cells shown in FIGS. 26, B and C. Genes commonly induced upon JQ1-treatment in MOLM-13, MV4-11 and K562 as well as upon BRD4-degradation are highlighted in blue. **** indicates p<0.0001 calculated by Wilcoxon's signed rank test for deviation of the median from 0.

Figure 31:
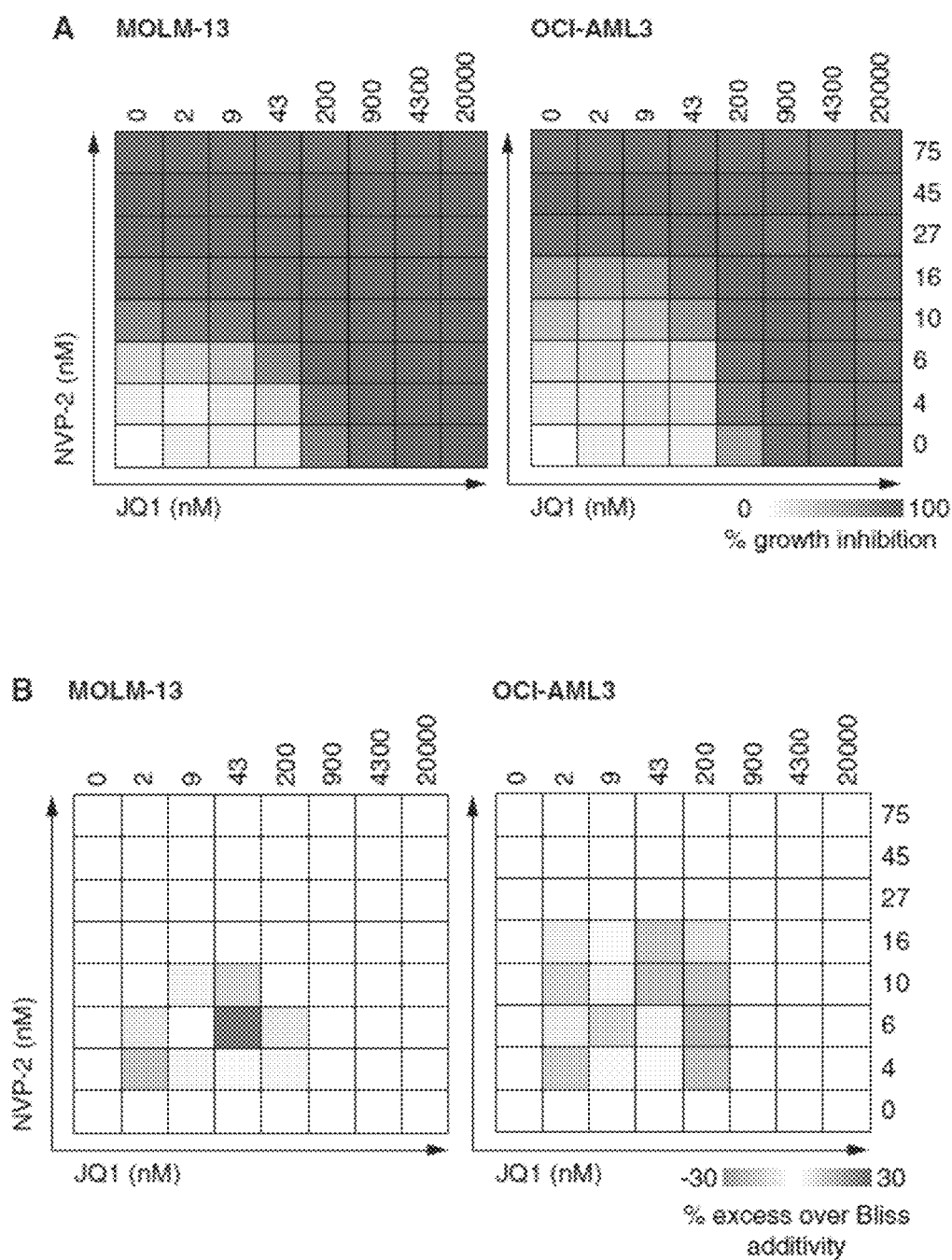
Figure 31:
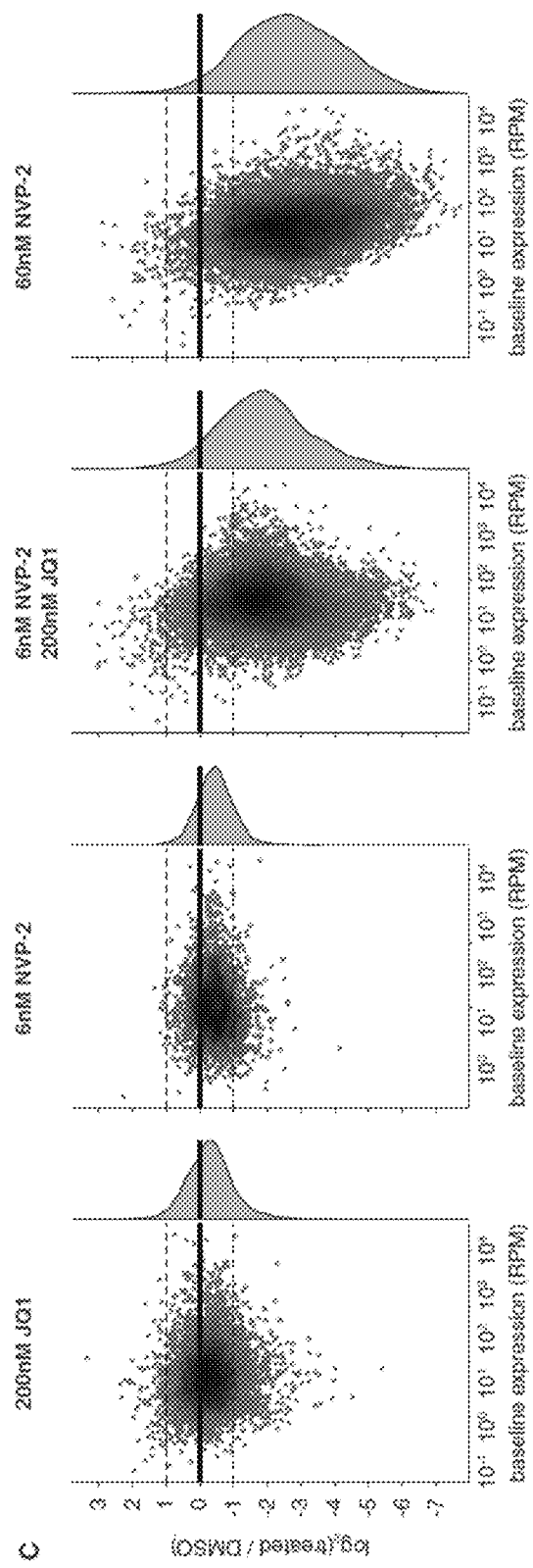
Figure 31:
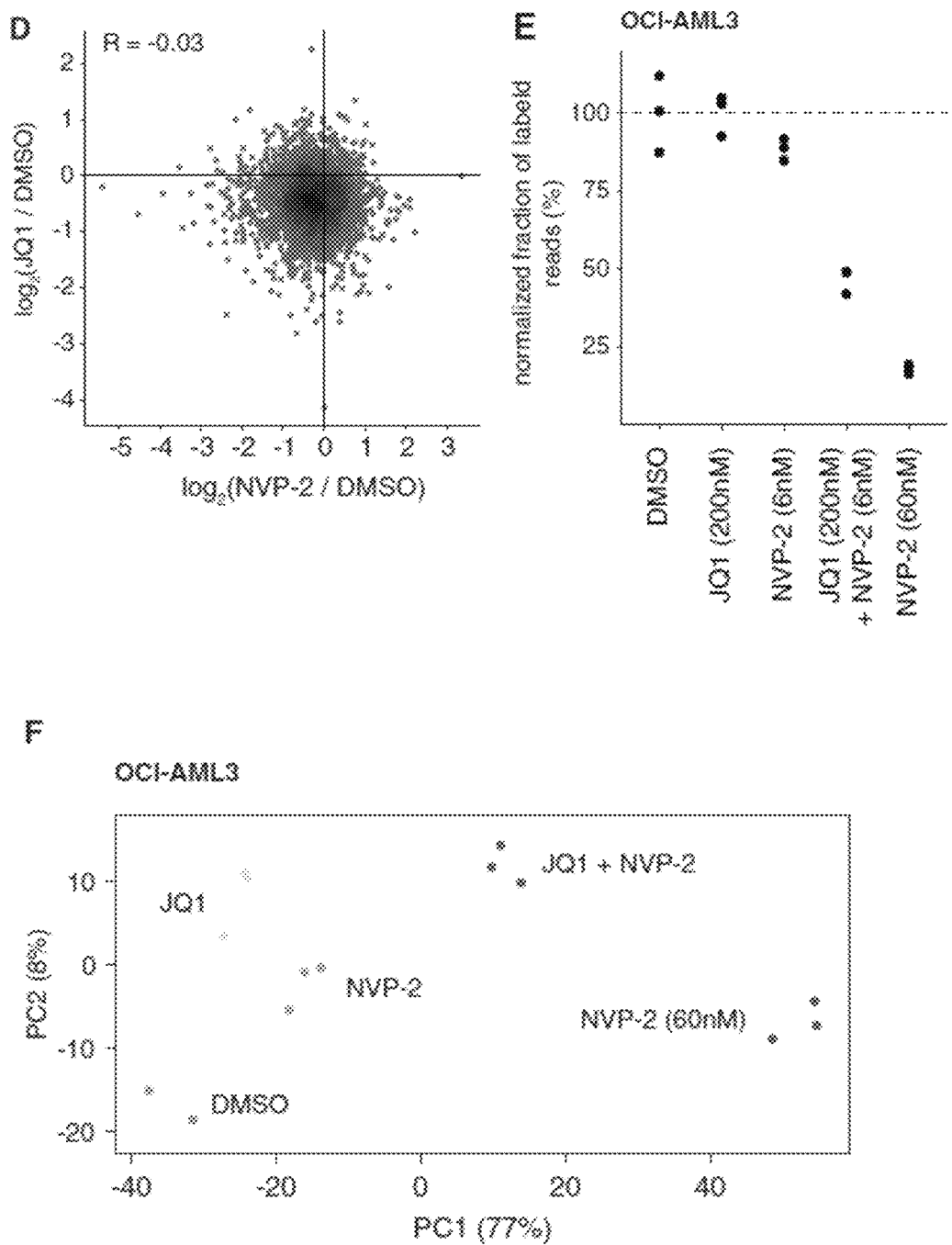

FIG. 31. Synergy of CDK9 and BET bromodomain inhibition at the cellular and the transcriptional level. (A) Growth inhibition of MOLM-13 and OCI-AML3 cells by indicated doses of NVP-2 and JQ1 for 3 days measured by the CellTiter-Glo luminescent cell viability assay. (B) Synergistic effects of JQ1 and NVP-2 in (A) expressed as excess over Bliss additivity. (C) Primary responses to JQ1, NVP-2 and combined treatment at indicated doses in MOLM-13 cells treated for 30' prior to $s^4U$ labeling for 60'. (D) Pairwise comparison of responses to JQ1 and an intermediate dose of NVP-2 (6 nM) shown in (C). R denotes Pearson correlation coefficient. (E) Global changes in mRNA output upon NVP-2 and JQ1 treatment of OCI-AML3 cells as in (C). Points indicate the fraction of $s^4U$ labeled over total reads in SLAM-seq for three independent replicates. (F) Principal component analysis of SLAM-seq reads from OCI/AML-3 cells treated with NVP-2 and JQ1 in (E). Percentages denote the fraction of overall variance explained by each principal component.

Figure 32:
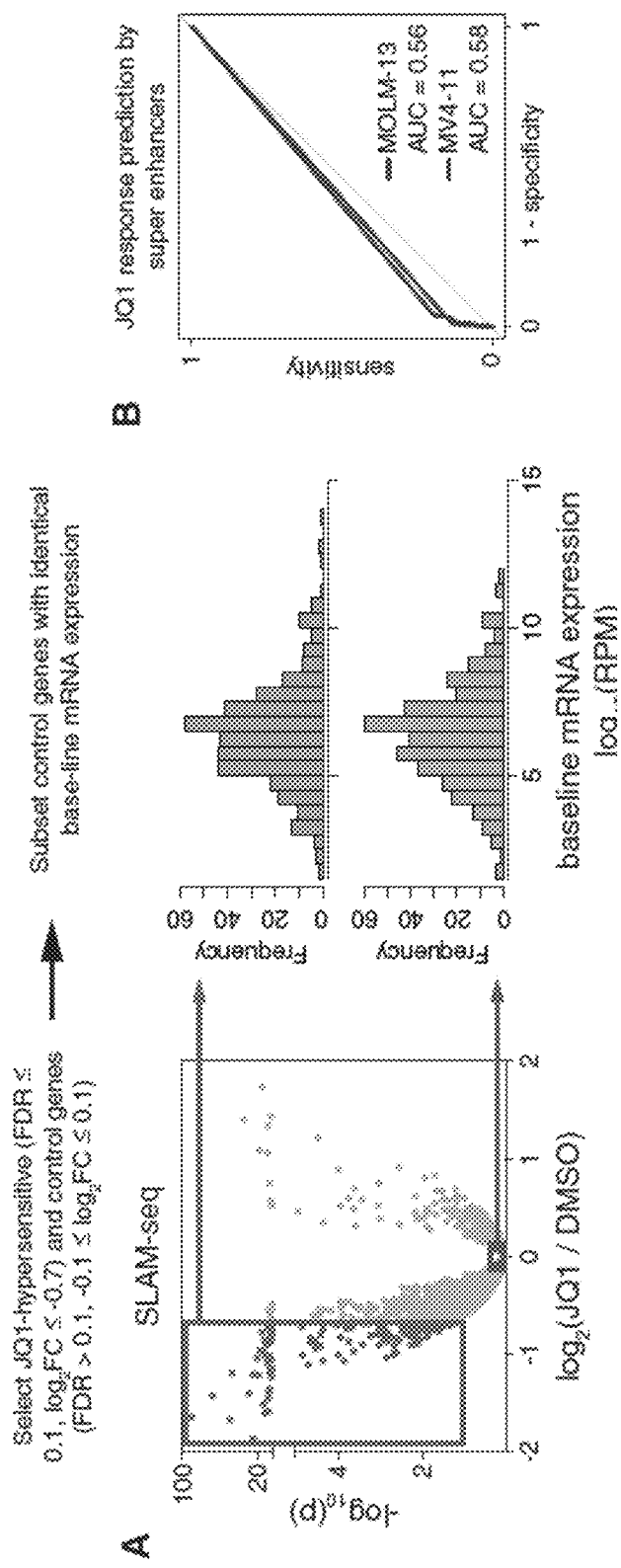
Figure 32:
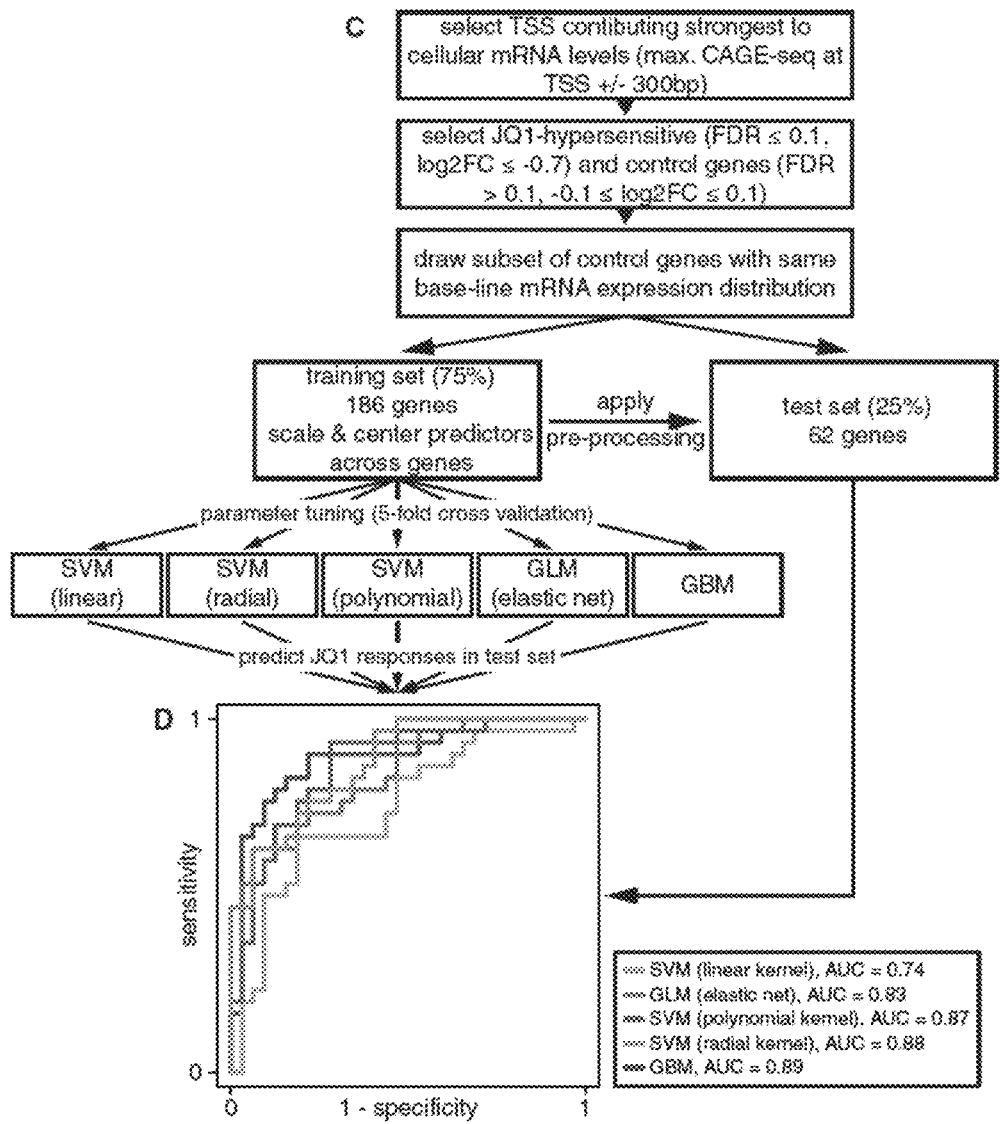

FIG. 32. Deriving and testing predictors of JQ1-hypersensitivity. (A) Workflow for the selection of JQ-1 hypersensitive genes and a balanced set of control genes based on SLAM-seq responses after 90' JQ1 treatment (30' pre-treatment+60' $s^4U$ labeling). Control genes were selected by iterative subsampling and testing for equal base-line expression by using a Kolmogorov-Smirnov test (KS). (B) ROC curve for the prediction of JQ1 hypersensitive versus control genes by super enhancers (SE). Each SE was assigned to the gene with the closest TSS and genes were sorted by super enhancer rank. (C) Workflow for deriving TSS-based classifiers of BETi-hypersensitivity in K562 cells shown in FIG. 27E. SVM—support vector machine, GLM—generalized linear model derived by elastic net regularization, GBM—gradient boosted model.

Figure 33:
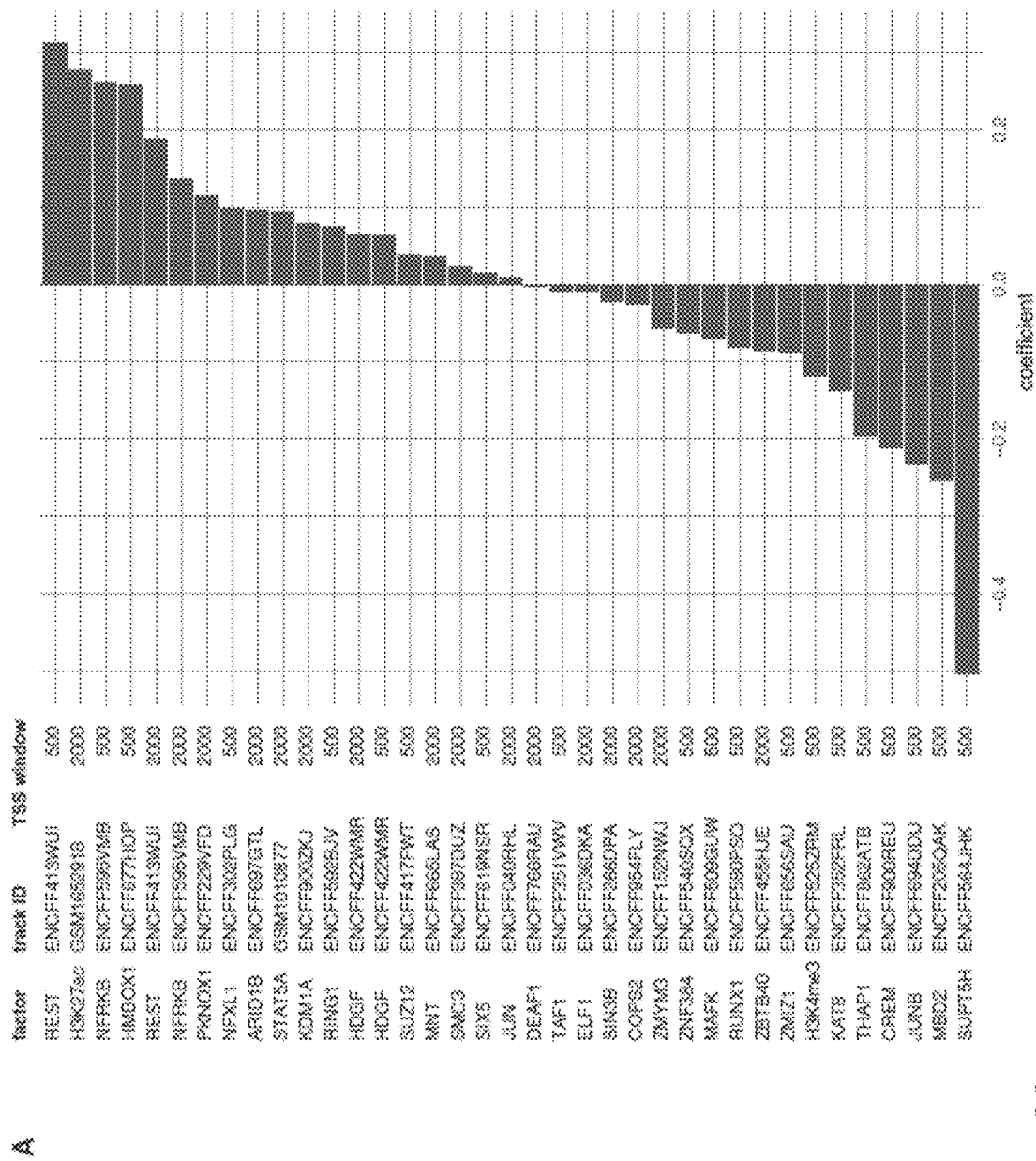
Figure 33:
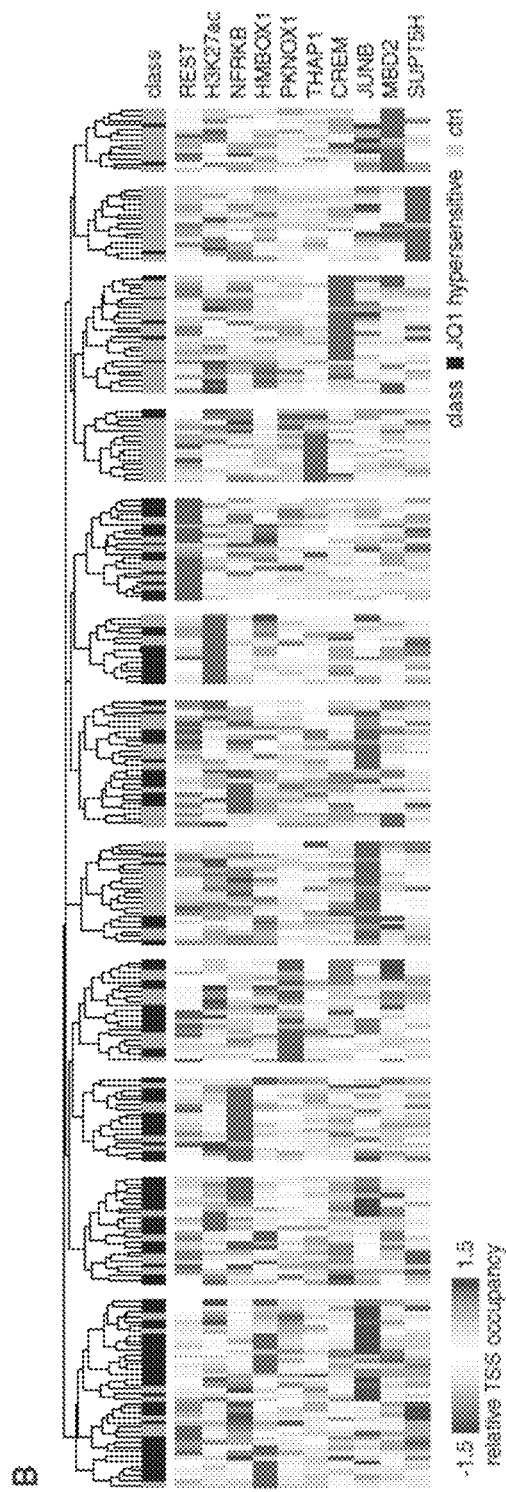

FIG. 33. Characterization of a GLM predicting JQ1-hypersensitivity in K562 cells. (A) Bargraph of coefficients for all predictors contributing to the GLM shown in FIG. 27E. The adjacent table lists each predictor, identifiers of the corresponding published ChIP-seq track (see also table S1) and whether signals were measured within 500 or 2000 bp from transcription start sites. (B) Heatmap and hierarchical clustering of JQ1-hypersensitive and control genes based on relative ChIP-seq signals of the 5 strongest positive and negative unique predictors in (A).

Figure 34:
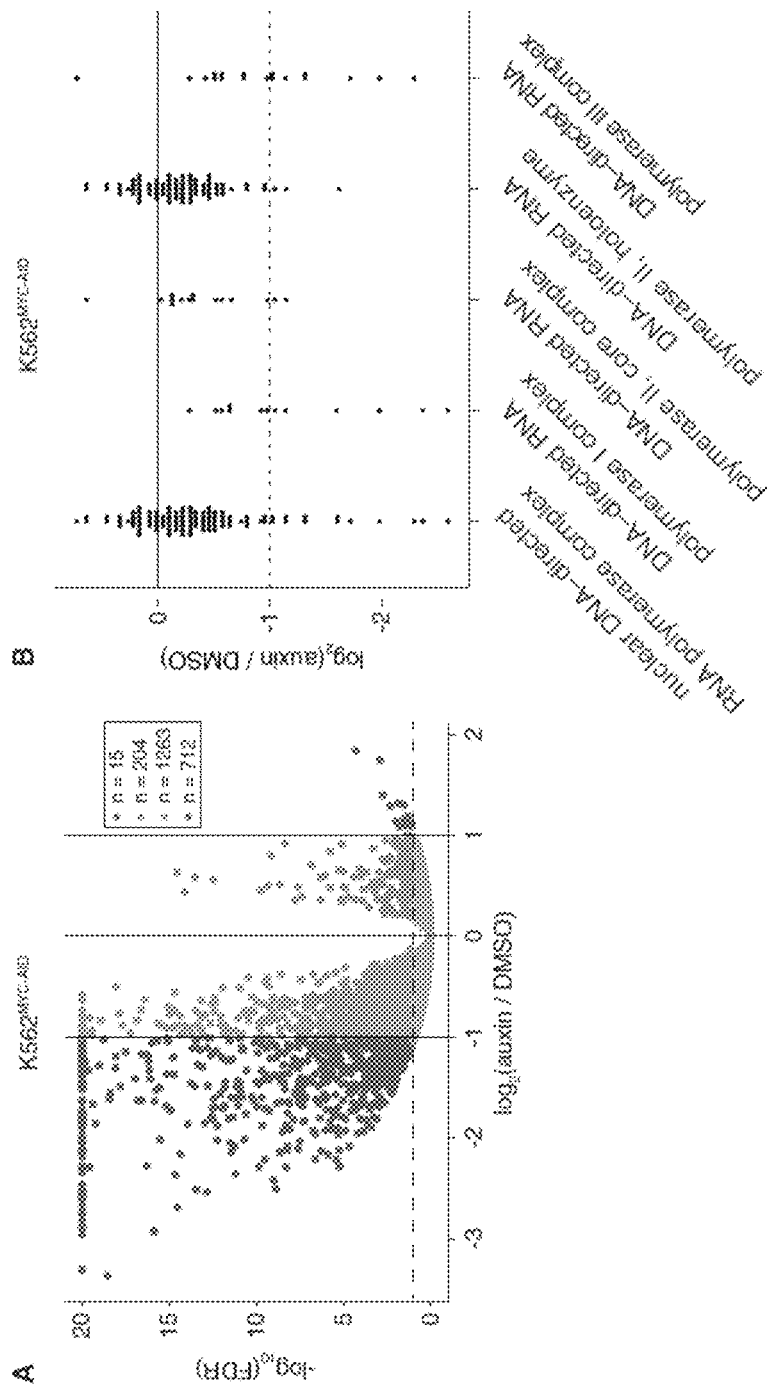
Figure 34:
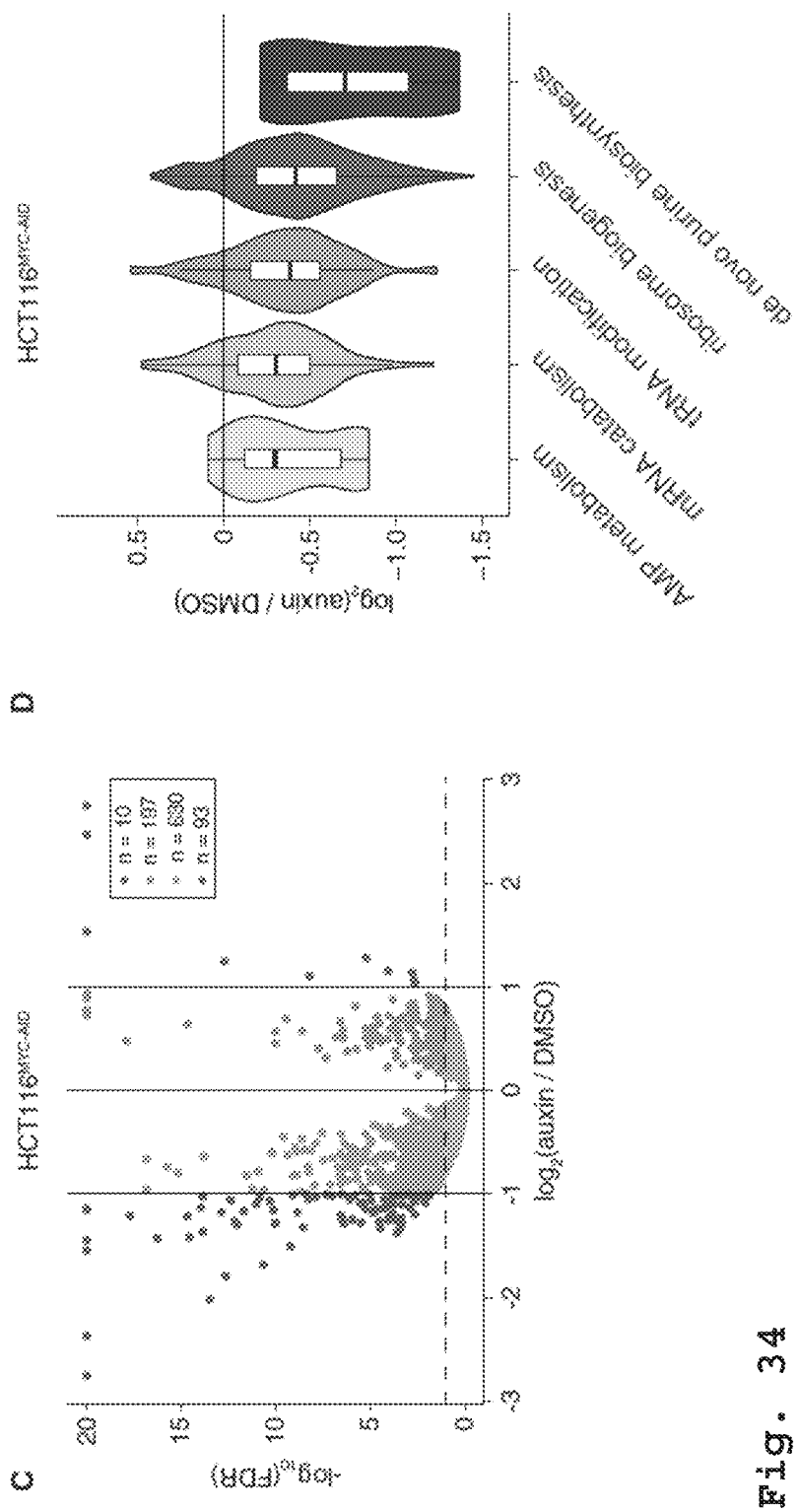

FIG. 34. Primary responses to MYC degradation in endogenously tagged MYC-AID cell lines. (A) Volcano plot of SLAM-seq responses of K562MYC-AID cells treated with auxin shown in FIG. 4C. The inset lists the total numbers of down- and up-regulated genes (FDR≤0.1) and genes deregulated by more than two-fold. Ordinate values are limited to 20 for legibility. (B) SLAM-seq responses of HCT116MYC-AID cells in (B) for genes associated with indicated GO-terms. (C) Volcano plot showing SLAM-seq results of HCT116MYC-AID cells treated with auxin as in (A). (D) SLAM-seq responses to acute MYC degradation in K562MYC-AID cells for genes encoding subunits of different RNA polymerase complexes, grouped by GO term.

Figure 35:
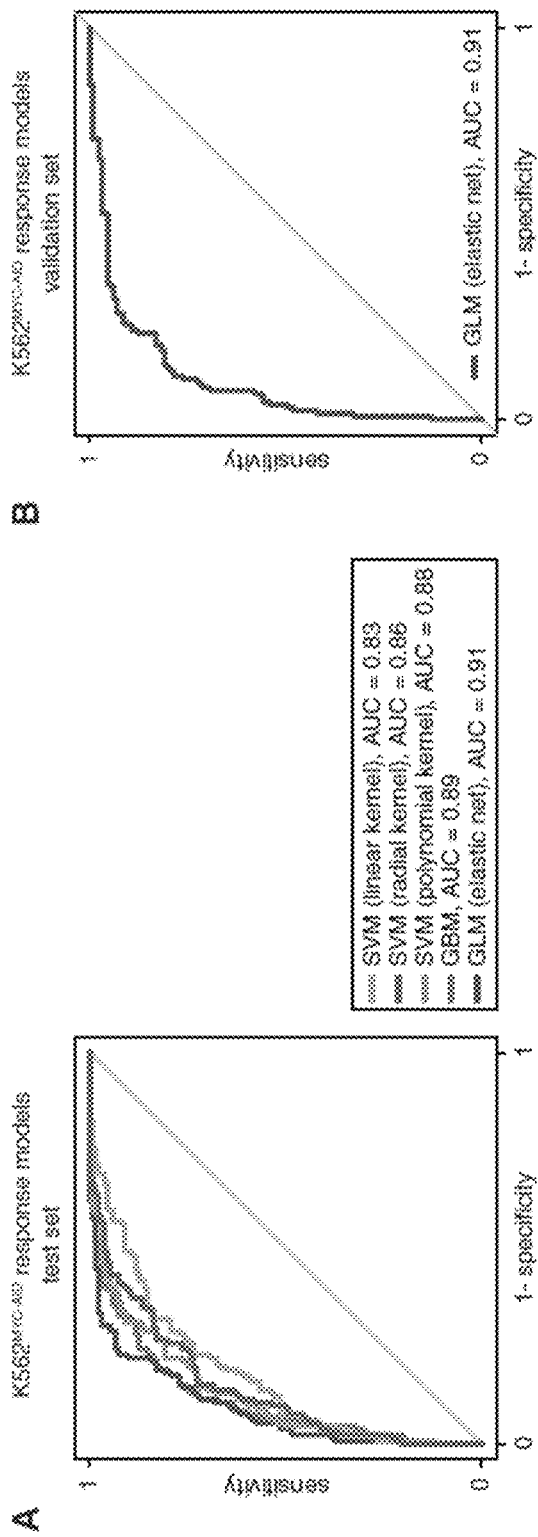
Figure 35:
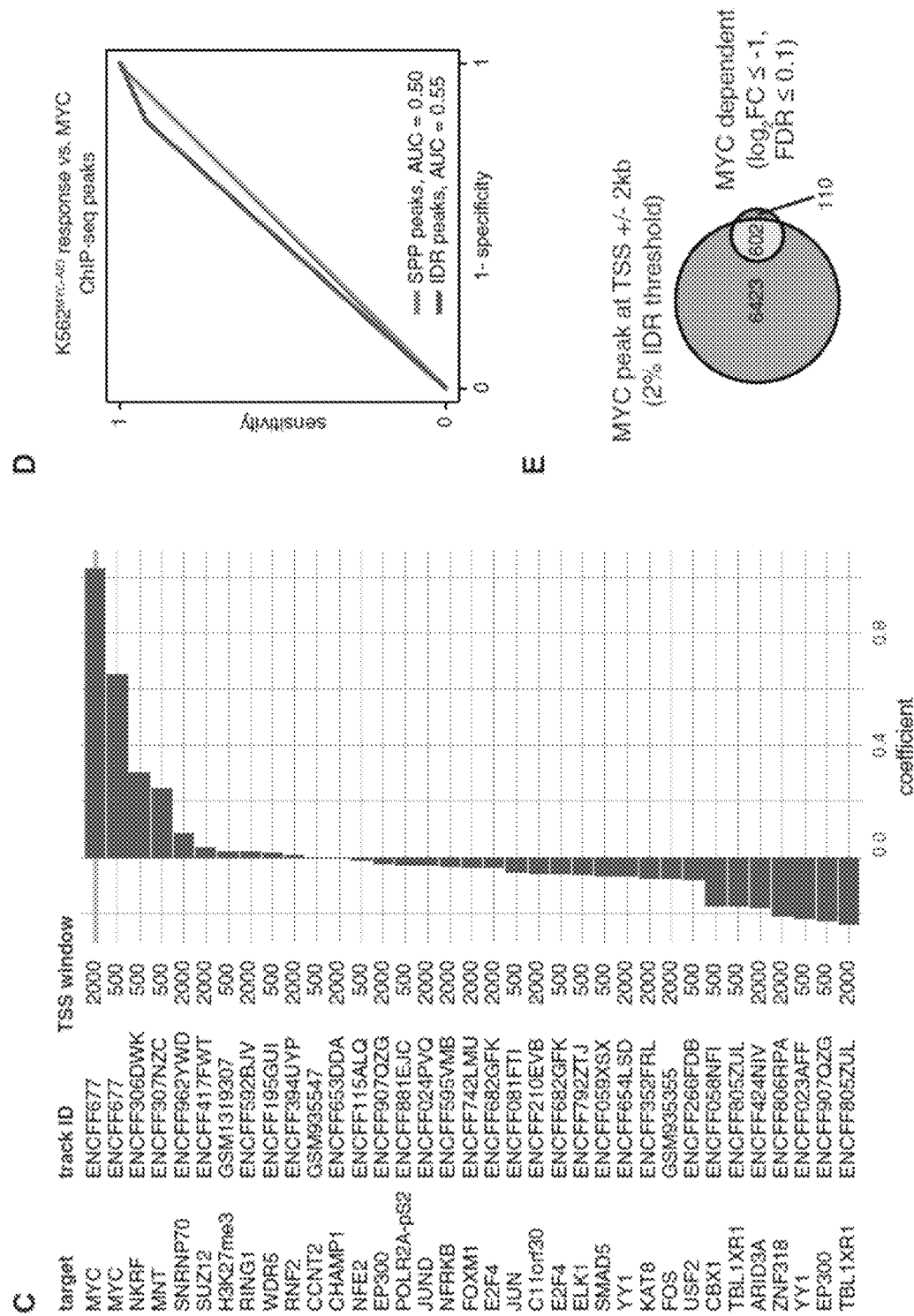

FIG. 35. Chromatin-based prediction of MYC-dependent gene expression. (A) ROC curve measuring the performance of 5 classifiers in discerning MYC-dependent genes (FDR≤1, log 2FC≤−1) from genes not responding to MYC-degradation (FDR≤0.1, −0.2≤log 2FC≤0.2) in FIG. 28C. Models were derived as in FIG. 32, trained on a test set of 802 genes and evaluated on a test set of 268 genes. (B) ROC curve evaluating the performance of the GLM shown in (A) on an additional set of genes held-out for validation. (C) Coefficients of all predictors of the GLM shown in (A). (D) ROC for prediction of MYC-dependent genes by presence of a MYC ChIP-seq peak within 2000 bp from a gene's TSS. For each gene, the TSS contributing strongest to cellular mRNA levels was selected based on CAGE-seq signal as in FIG. 32. SPP peaks—peaks called by SPP, IDR peaks—peaks passing an irreproducible discovery rate threshold of 2%. (E) Venn diagram of 7135 genes grouped into MYC-bound genes and MYC-dependent genes as above.

Figure 36:
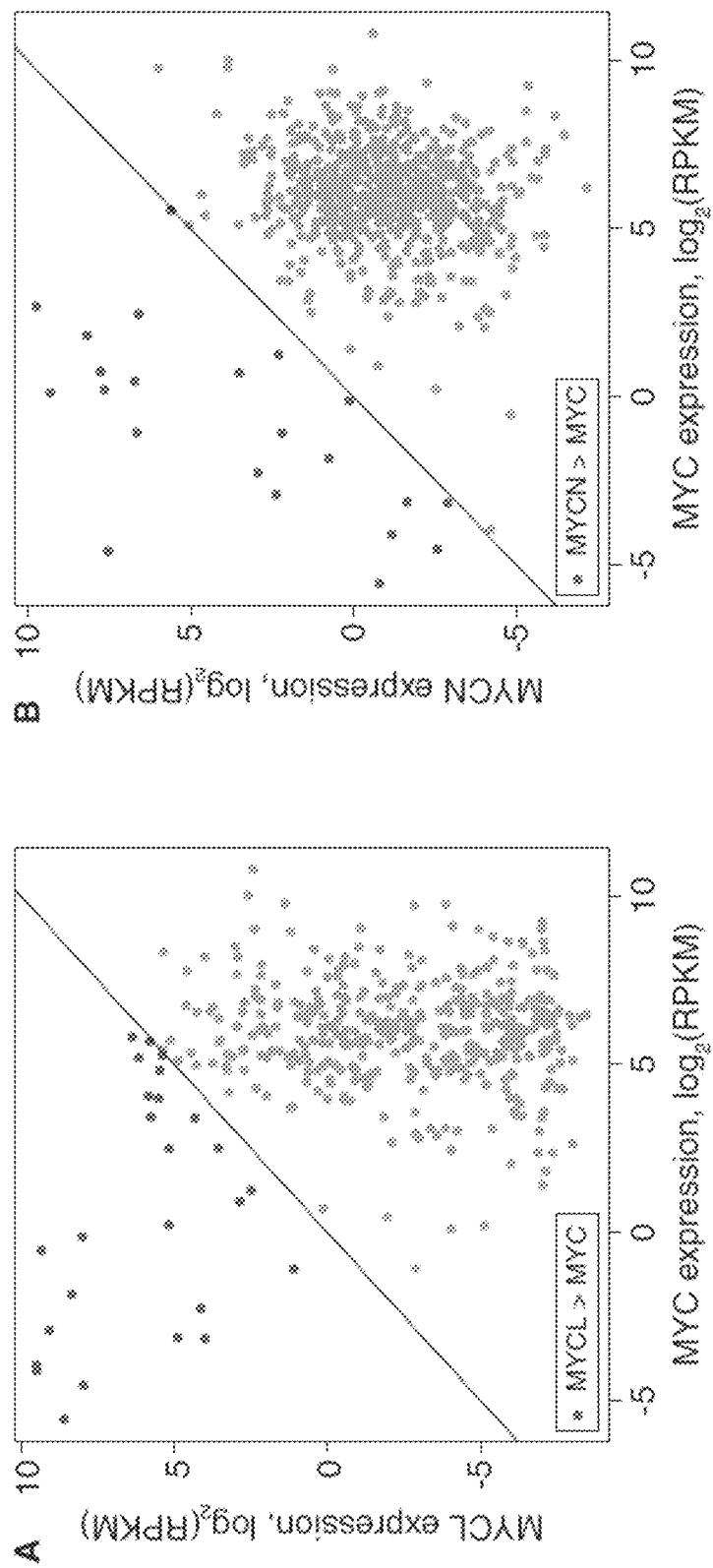

FIG. 36. Expression of MYC orthologs in human cancer cell lines. (A) Comparison of MYC and MYCL expression in RNA-seq profiles from 672 cancer cell lines. (B) Comparison of MYC and MYCN expression in cancer cell lines as in (A).

Figure 37:
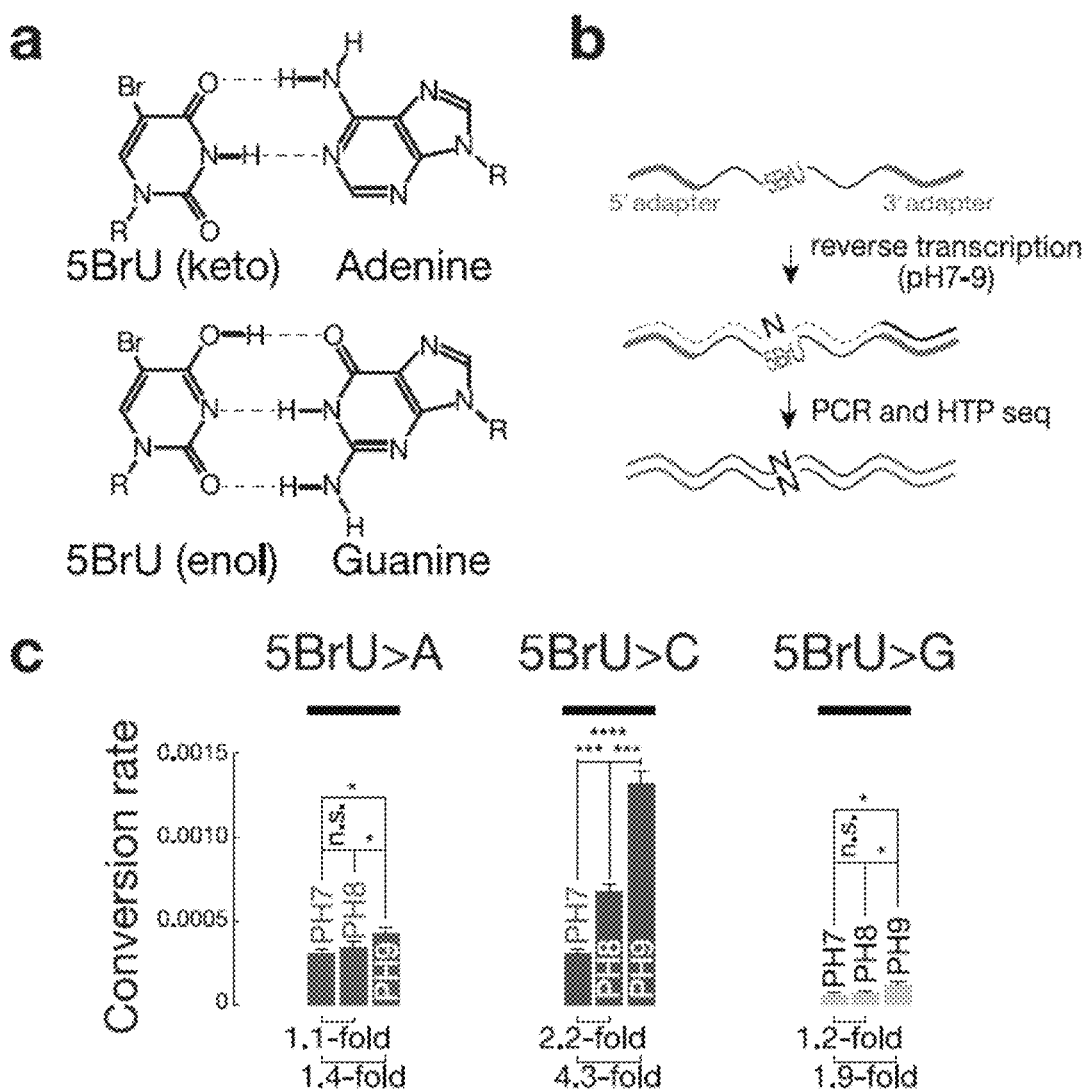

FIG. 37. pH-dependent base-pairing frequencies during reverse transcription of a 5-Bromouridine (5BrU)-containing RNA oligonucleotide measured by sequencing. (a) The tautomeric forms of 5BrU exhibit different pH-dependent base-pairing properties to adenine or guanine. (b) Schematic outline of experiment to detect pH-dependent effect on nucleotide misincorporation at a 5BrU-modified position in the context of RNA. (c) Conversion rates for the specific conversions observed at the 5BrU modified nucleotide position after reverse transcription under the indicated pH condition. Fold-increase in conversion rates relative to pH7 condition is indicated. The number of independent measurements are n=3, and the bars represent average conversion rates ±SD. P-Values (unpaired, parametric Student's t-test) are indicated. N.s., not significant (p>0.05); *, p<0.05; , p<0.01; *, p<0.001; and ****, p<0.0001.

EXAMPLES

Example 1: Materials and Methods

Carboxyamidomethylation of $s^4U$

If not indicated otherwise, carboxyamidomethylation was performed under standard conditions (50% DMSO, 10 mM iodoacetamide, 50 mM sodiumphosphate buffer pH8, for 15 min at 50° C.) using either 1 mM 4-thiouracil (SIGMA), 800 µM 4-thiouridine (SIGMA), or 5-50 µg total RNA prepared from $s^4U$ metabolic labeling experiments. The reaction was quenched by addition of excess DTT.

Adsorption Measurements 1 mM 4-thiouracil was incubated under optimal reaction conditions (10 mM iodoacetamide, 50% DMSO, 50 mM sodiumphosphate buffer pH8, for 15 min at 50° C.) if not indicated otherwise. Reaction was quenched by the addition of 100 mM DTT and adsorption spectra were measured on a Nanodrop 2000 instrument (Thermo Fisher Scientific), followed by baseline subtraction of adsorption at 400 nm.

Mass Spectrometry 40 nmol 4-thiouridine or 6-thioguanosine were reacted in the absence or presence of 0.05, 0.25, 0.5 or 5 µmol iodoacetamide under standard reaction conditions (50 mM sodiumphosphate buffer, pH 8; 50% DMSO) at 50° C. for 15 min. The reaction was stopped with 1% acetic acid. Acidified samples were separated on a Ultimate U300 BioRSLC HPLC system (Dionex; Thermo Fisher Scientific), employing a Kinetex F5 Pentafluorophenyl column (150 mm×2.1 mm; 2.6 µm, 100 Å; Phenomenex) with a flow rate of 100 µl/min. Nucleosides were on-line analyzed using a TSQ Quantiva mass spectrometer (Thermo Fisher Scientific) after electrospray ionization with the following SRMs: 4-Thiouridine m/z 260→129, alkylated 4-Thiouridine m/z 318→186, 6-Thio-Guanosine m/z 300→168 and alkylated 6-Thio-Guanosine m/z 357→225. Data were interpreted using the Trace Finder software suite (Thermo Fisher Scientific) and manually validated.

Primer Extension Assays

Primer extension assays were essentially performed as described previously by Nilsen et al. (Cold Spring Harb Protoc. 2013, 1182-1185). Briefly, template RNA oligonucleotides (5L-let-7-3L or 5L-let-7-$s^4$Up9-3L; Dharmacon; see Table for sequences) were deprotected according to the instructions of the manufacturer and purified by denaturing polyacrylamide gel-elution. 100 µM purified RNA oligonucleotides were treated with 10 mM iodoacetamide (+IAA) or EtOH (−IAA) in standard reaction conditions (50% DMSO, 50 mM sodiumphosphate buffer, pH 8) for 15 min at 50° C. The reaction was stopped by addition of 20 mM DTT, followed by ethanol precipitation. RT primer (see Table for sequence) was 5' radiolabeled using $\gamma$-$^{32}$P-ATP (Perkin-Elmer) and T4-polynucleotide kinase (NEB), followed by denaturing polyacrylamide gel-purification. 640 nM $\gamma$-$^{32}$P-RT primer was annealed to 400 nM 5L-let-7-3L or 5L-let-7-$s^4$Up9-3L in 2× annealing buffer (500 mM KCl, 50 mM Tris pH 8.3) in a PCR machine (3 min 95° C., 30 sec 85° C. Ramp 0.5° C./s, 5 min 25° C. Ramp 0.1° C./s). Reverse transcription was performed using Superscript II (Invitrogen), Superscript III (Invitrogen), or Quant-seq RT (Lexogen) as recommended by the manufacturer. For dideoxynucleotide reactions, a final concentration of 500 µM ddNTP (as indicated) was added to RT reactions. Upon completion, RT reactions were resuspended in formamide loading buffer (Gel loading buffer II, Thermo Fisher Scientific) and subjected to 12.5% denaturing polyacrylamide gel electrophoresis. Gels were dried, exposed to storage phosphor screen (PerkinElmer), imaged on a Typhoon TRIO variable mode imager (Amersham Biosciences), and quantified using ImageQuant TL v7.0 (GE Healthcare). For analysis of drop-off, signal-intensities at p9 were normalized to preceding drop-off signal intensities (bg, FIG. 4B) for individual reactions. Values reporting the change in drop off signal (+IAA/−IAA) for $s^4$U-containing and non-containing RNA oligonucleotides were compared for the indicated reverse transcriptases. A corresponding set-up was used to analyse 6-thioguanosine modification as alternative to 4-thiouridine.

TABLE

| RNA oligonucleotides used for primer extension assay. $s^4U$ indicates 4-thiouridine; $s^6U$ indicates 6-thioguanosine. Inspected sequence of let-7 is indicated in italics. | |
|---|---|
| Name | RNA sequence (5'-3') |
| 5L-let-7-3L | ACACUCUUUCCCUACACGACGCUCUUCCGAUC*UUGAGGUAGUA GGUUGUAUAGUAG*AUCGGAAGAGCACACGUCUC (SEQ ID NO: 1) |
| 5L-let-7-$s^4$U-p9-3L | ACACUCUUUCCCUACACGACGCUCUUCCGAUC*UUGAGGUAG $s^4U$ AGGUUGUAUAGUAG*AUCGGAAGAGCACACGUCUC (SEQ ID NO: 2) |
| inspected let-7-$s^6$G sequence | *UGAGGUA $s^6G$ UAGGUUGUAUAGU* (SEQ ID NO: 3) |
| DNA oligonucleotide used for primer extension assay. | |
| Name | DNA sequence (5'-3') |
| RT primer | GTGACTGGAGTTCAGACGTGTGCTCTTCCGATCT (SEQ ID NO: 4) |

DNA oligonucleotides used for cDNA amplification followed by Illumina high-throughput sequencing. Barcode nucleotides (N) are TABLE-continued indicated in italics.

| Name | DNA sequence (5'-3') |
|---|---|
| Solexa_PCR_fwd | AATGATACGGCGACCACCGAGATCTACACTCTTTCCCTACACG ACGCTCTTCCGATCT (SEQ ID NO: 5) |
| Solexa_IDX_rev | CAAGCAGAAGACGGCATACGAGAT*NNNNNN*GTGACTGGAGTTC AGACGTGTGCTCTTCCGATCT (SEQ ID NO: 6) |

HPLC Analysis of $s^4$U- or $s^6$G-Labeled RNA

Analysis of $s^4$U- or $s^6$G-incorporation into total RNA following metabolic labeling was performed as previously described by Spitzer et al. (Meth Enzymol. 539, 113-161 (2014)).

Cell Viability Assay 5000 mES cells were seeded per 96 well the day before the experiment. Medium containing different concentrations of $s^4$U (as indicated) was added to the cells for 12 h or 24 h. Cell viability was assessed by CellTiter-Glo® Luminescent Cell Viability Assay (Promega) according to the instructions of the manufacturer. Luminescent signal was measured on Synergy using Gen5 Software (v2.09.1).

Cell Culture

Mouse embryonic stem (mES) cells (clone AN3-12) were obtained from Haplobank (Elling et al., WO2013/079670) and cultured in 15% FBS (Gibco), 1× Penicillin-Streptomycin solution (100 U/ml Penicillin, 0.1 mg/ml Streptomycin, SIGMA), 2 mM L-Glutamine (SIGMA), 1×MEM Nonessential amino acid solution (SIGMA), 1 mM sodium pyruvate (SIGMA), 50 µM 2-Mercaptoethanol (Gibco) and 20 ng/ml LIF (in-house produced). Cells were maintained at 37° C. with 5% $CO_2$ and passaged every second day.

Modification of RNA to Alter Sequencing ("SLAM-Seq")

mES cells were seeded the day before the experiment at a density of $10^5$ cells/ml in 10 cm dishes. $s^4$U-metabolic labeling was performed by incubation of mES cells in standard medium but adding 100 µM $s^4$U or $s^6$G (SIGMA) from a 500 mM stock solution in water. During the metabolic labeling, $s^4$U or $s^6$G containing medium was exchanged every 3 h. For the uridine chase experiment, $s^4$U or $s^6$G containing medium was discarded, cells were washed twice with 1× PBS and incubated with standard medium supplemented with 10 mM uridine (SIGMA). Cells were directly lysed in TRIzol® (Ambion) and RNA was extracted following the manufacturer instructions except that 0.1 mM final concentration of DTT was added during isopropanol precipitation. RNA was resuspended in 1 mM DTT. 5 µg of total RNA were treated with 10 mM iodoacetamide under optimal reaction conditions and subsequently ethanol precipitated and subjected to QuantSeq 3' end mRNA library preparation (Moll et al., Nat Methods 11 (2014); WO2015/140307).

RNA Library Preparation

Standard RNA seq libraries were prepared using NEBNext® Ultra™ Directional RNA Library Prep Kit for Illumina® (NEB) following the instructions of the manufacturer. Cap-seq libraries were prepared as previously described by Mohn et al. (Cell. 157, 1364-1379 (2014)) except that ribosomal RNA depletion using magnetic RiboZero Kit (Epicenter) was performed prior to fragmentation. Messenger RNA 3' end sequencing was performed using the Quant-seq mRNA 3' end library preparation kit (Lexogen) according to the instructions of the manufacturer.

Data Analysis

Gel images were quantified using ImageQuant v7.0a (GE Healthcare). Curve fitting was performed according to the integrated rate law for a first-order reaction in Prism v7.0 (GraphPad) or R (v2.15.3). Statistical analyses were performed in Prism v7.0a (GraphPad), Excel v15.22 (Microsoft) or R (v2.15.3).

Bioinformatics

Figure 5:
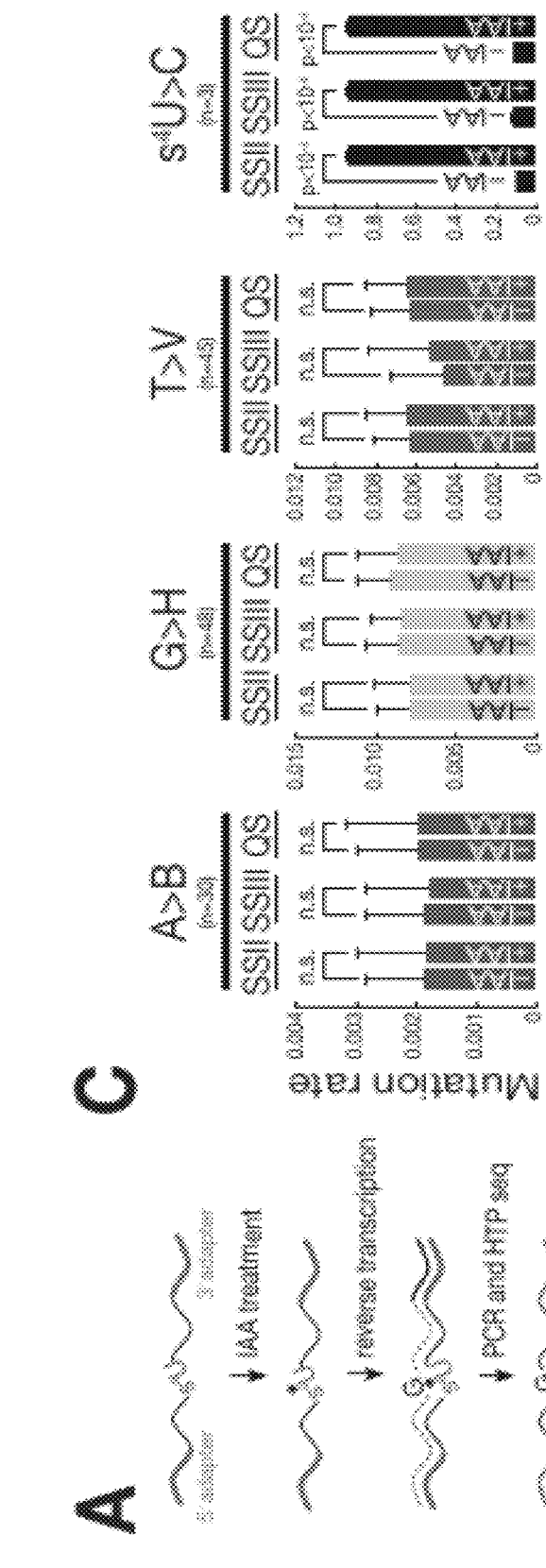
FIG. 5. Alkylation enables the quantitative identification of $s^4U$-incorporations in RNA at single nucleotide resolution. (A) RNA with or without 4-thiouridine ($s^4U$) incorporation at a single position (p9) was treated with iodoacetamide (IAA) and subjected to reverse transcription and gel-extraction of full-length product followed by PCR amplification and high-throughput (HTP) sequencing. (B) Mutation rates for each position of a control RNA (left panels) and a $s^4U$-containing RNA (right panels) in the presence or absence of iodoacetamide (IAA) treatment employing the indicated reverse transcriptase are shown. Bars represent average mutation rates ±SD of three independent replicates. Numbers of sequenced reads in each replicate (r1-r3) are indicated. Nucleotide identity occurrence at p9 is shown. (C) Mutation rates for the indicated mutations in the presence or absence of iodoacetamide (IAA) treatment employing Superscript II (SSII), Superscript III (SSIII), or Quant-seq reverse transcriptase (QS). Mutation rates were averaged across positions with the same nucleotide identity for both, $s^4U$-containing and non-containing RNA oligonucleotides. P-Values (determined by Student's t-test) are indicated. N.s., not significant (p>0.05).
Figure 5:
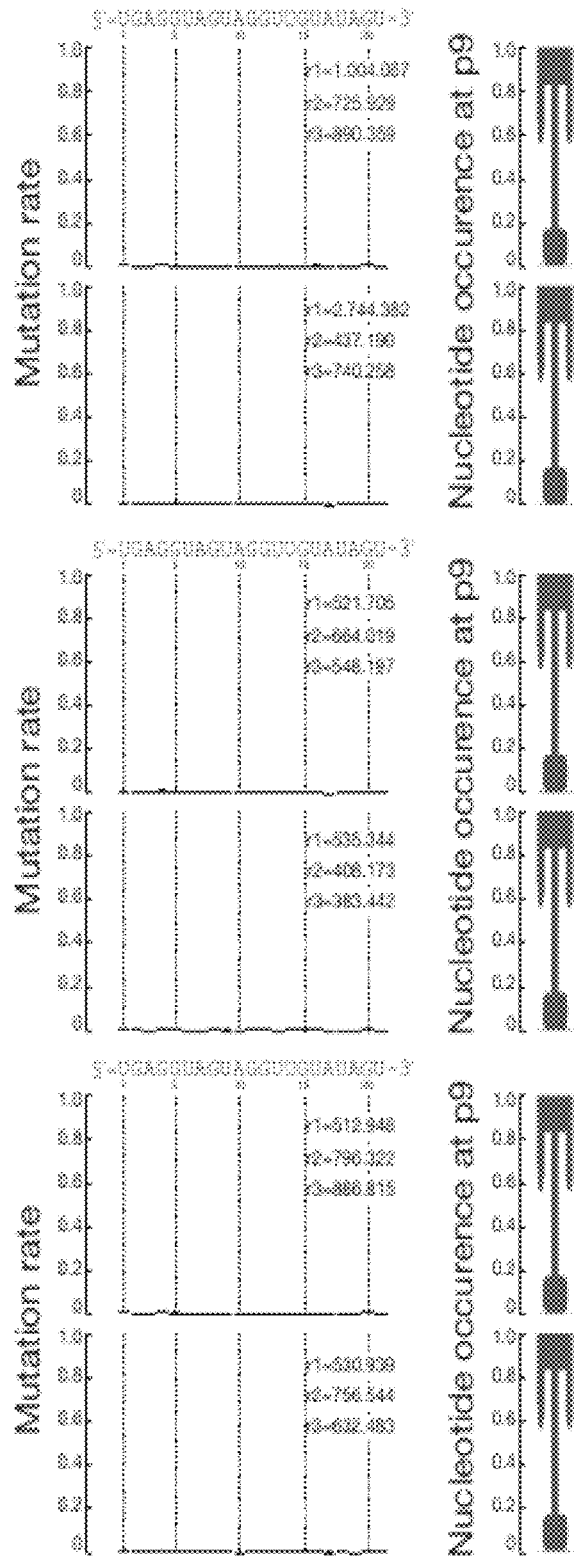

For sequencing analysis of synthetic RNA samples (FIG. 5) barcoded libraries were demultiplexed using Picard Tools BamIndexDecoder v1.13 allowing 0 mismatches in the barcode. Resulting files were converted to fastq using picard-tools SamToFastq v1.82. Cutadapt v1.7.1 was used to trim adapters (allowing for default 10% mismatch in adapter sequence) and filter for sequences of 21 nt length. Resulting sequences were aligned to mature dme-let-7 sequence (5''-TGAGGTAGTAGGTTGTATAGT-3', SEQ ID NO: 7) using bowtie v0.12.9 allowing for 3 mismatches and converted to bam using samtools v0.1.18. Sequences containing ambiguous nucleotides (N) were removed. Remaining aligned reads were converted to pileup format. Finally, the fraction of each mutation per position was extracted from pileup. Output table was analyzed and plotted in Excel v15.22 (Microsoft) and Prism v7.0a (GraphPad).

For mRNA 3' end sequencing data analysis, barcoded libraries were demultiplexed using Picard Tools BamIndexDecoder v1.13 allowing 1 mismatch in the barcode. Adapters were clipped using cutadapt v1.5 and reads were size-filter for ≥15 nucleotides. Reads were aligned to mouse genome mm10 using STAR aligner v2.5.2b. Alignments were filtered for alignment scores ≥0.3 and alignment identity ≥0.3 normalized to read length. Only alignments with ≥30 matches were reported. Only chimeric alignments with an overlap ≥15 bp were allowed. 2-pass mapping was used. Introns <200 kb were filtered, alignments containing non-canonical junctions were filtered. Alignment with a mismatch to mapped bases ratio ≥0.1 or with a maximum number of 10 mismatches were filtered. The maximum number of gaps allowed for junctions by 1,2,3,N reads was set to 10 kb, 20 kb, 30 kb and 50 kb, respectively. The minimum overhang length for splice junctions on both sides for (1) non-canonical motifs, (2) GT/AG and CT/AC motif, (3) GC/AG and CT/GC motif, (4) AT/AC and GT/AT motif was set to 20, 12, 12, 12, respectively. "Spurious" junction filtering was used and the maximum number of multiple alignments allowed for a read was set to 1. Exonic reads (Gencode) were quantified using FeatureCounts.

For Cap analysis gene expression (CAGE), barcoded libraries were demultiplexed using Picard Tools BamIndexDecoder v1.13 allowing 1 mismatch in the barcode. The first 4 nt of the reads were trimmed using seqtk. Reads were screened for ribosomal RNA by aligning with BWA (v0.6.1) against known rRNA sequences (RefSeq). The rRNA subtracted reads were aligned with TopHat (v1.4.1) against the *Mus musculus* genome (mm10). Maximum multi-hits were set to 1, segment-length to 18 and segment-mismatch to 1. Additionally, a gene model was provided as GTF (Gencode VM4).

For analysis of mRNA 3' end sequencing (Quant-seq) datasets, reads were demultiplexed using Picard Tools BamIndexDecoder v1.13 allowing 1 mismatch in the barcode. Five nucleotides at the 5' end of demultiplexed reads were trimmed. Reads were aligned to mouse genome mm10 and alignments in annotated 3' UTRs (Gencode) were counted using SLAMdunk (Neumann & Rescheneder, t-neumann-.github.io/slamdunk/; Herzog et al., Nature Methods 14, 1198-1204 (2017)). Briefly, SLAMdunk relies on NextGenMap, a flexible and fast read mapping program, and was tailored using an adapted scoring scheme eliminating T>C mismatch penalties for the mapping step. T>C containing reads and non-T>C containing reads aligning to 3' UTRs were quantified to deduce $s^4$U- or unlabeled transcript abundance, respectively.

For transcriptional output analysis, the number of normalized reads (in cpm; "Steady-state Expression") and the number of normalized reads containing ≥1 T/C mutation (in cpm; "Transcriptional Output") were obtained for every gene after aligning the high-throughput sequencing data with SLAMdunk to the mouse genome mm10. Mitochondrial (Mt-) and predicted (GM-) genes were excluded from the analysis. Background T/C reads (T/C reads observed without $s^4$U labeling) were subtracted from the T/C reads in the 1 h time-point and an expression threshold of >5 cpm for the mean of "Steady-state Expression" was set. To identify genes with a high transcriptional output, a linear regression was fitted after plotting log 10(SteadyState Expression) vs. log 10(Transcriptional Output) (number of genes: 6766), described by the equation Y=0.6378*X−1.676. For each gene, the distance to the fitted curve was calculated ("ΔY") as in ΔY=TranscriptionalOutput (cpm) −(0.6378*SteadystateExpression (cpm)−1.676). "High transcriptional output" genes were defined by ΔY>0.5 (number of genes: 828). "High expression genes" were defined by steady-state CPM>log 10(2.15) (number of genes: 825). To predict the transcription factor network defining each class of genes, Ingenuity Pathway Analysis (Qiagen) v27821452, a web-delivered application that enables biologists to discover, visualize and explore therapeutically relevant networks significant to their experimental results, such as gene expression data sets, was used with the input of "High transcriptional Output" or "High expression" genes. For a detailed description of Ingenuity Pathways Analysis visit www.Ingenuity.com. The top 5 predicted upstream regulators are shown.

To predict pathways of "High transcriptional Output" or "High expression" genes, the online tool Enrichr was used with the input of the two gene classes. The top 5 predicted pathways are displayed.

Example 2: Thiol-Linked Alkylation for the Metabolic Sequencing of RNA

Figure 1:
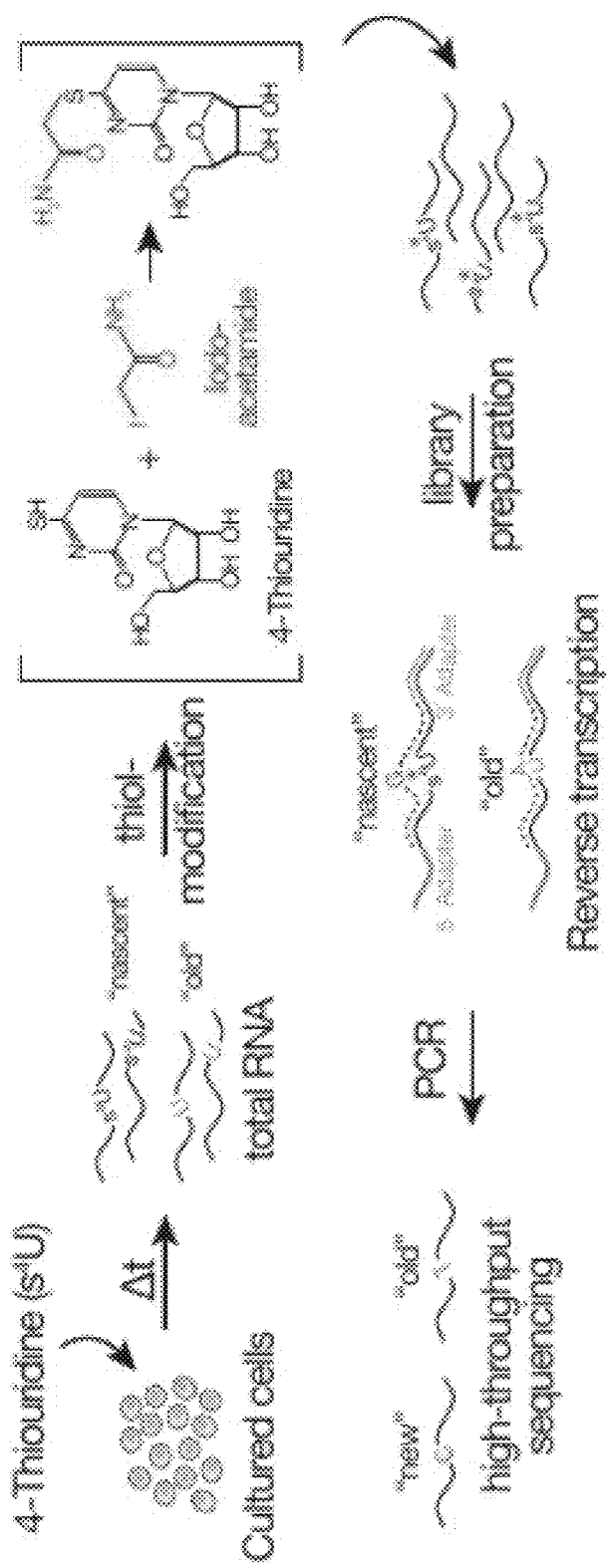
FIG. 1. Schematic overview of thiol(SH)-linked alkylation for the metabolic sequencing of RNA. Cells are treated with 4-thiouridine ($s^4U$), which upon cellular uptake incorporates into newly transcribed RNA. Upon total RNA preparation at given time points $s^4U$-residues present in newly generated RNA species are carboxyamidomethylated by treatment with iodoacetamide (IAA), resulting in a bulky group at the base-pairing interface. When combined with well-established RNA library preparation protocols, the presence of the bulky group at the sites of $s^4U$-incorporation leads to the specific and quantitative misincorporation of G across alkylated $s^4U$ during reverse transcription (RT). $s^4U$-containing sites can be identified bioinformatically in high-throughput sequencing libraries at single nucleotide resolution by calling T-to-C transitions.

As proof-of-principle thiol nucleotide-analog was selected as example of a derivatization strategy that bypasses the need for biochemical separation of $s^4$U- or $s^6$G-labeled and unlabeled RNA species to determine RNA expression kinetics in cultured cells (FIG. 1): This strategy is based on well-established metabolic labeling approaches but avoids the ineffective and time-consuming biotinylation-step. It contains a short chemical treatment protocol that involves the modification of $s^4$U-containing RNA with iodoacetamide, a sulfhydryl-reactive compound, which—upon reaction with $s^4$U or $s^6$G—creates a bulky group at the base-pairing interface (FIG. 1). When combined with well-established RNA library preparation protocols, the presence of the bulky group at the sites of $s^4$U-incorporation leads to the specific and quantitative misincorporation of G during reverse transcription (RT), but does not interfere with RT-processivity. $s^4$U- or $s^6$G-containing sequences can therefore be identified by sequence comparison or bioinformatically in high-throughput sequencing libraries at single nucleotide resolution by calling T to C transitions. Importantly, no enzyme that converts uridine to cytosine is known and similar error rates (i.e. T>C conversions) in high throughput RNA sequencing datasets using e.g. the Illumina HiSeq 2500 platform are rare, occurring at a frequency of less than one in a ten thousand. This approach is referred to "SLAM-seq" as abbreviation of its most preferred embodiment, the thiol(SH)-linked alkylation for the metabolic sequencing of RNA.

SLAM-seq is based on nucleotide-analog derivatization chemistry that enables to detect metabolic-labeling-derived 4-thiouridine-incorporation events in RNA species at single-nucleotide resolution by high-throughput sequencing. We show that the new method accurately measures RNA polymerase II-dependent poly-adenylated transcriptional output, and recapitulates global post-transcriptional gene regulatory signatures in mouse embryonic stem cells. The invention provides a scalable, highly quantitative, cost- and time-effective method for the rapid and transcriptome-wide analysis of RNA expression kinetics at high temporal resolution.

Figure 2:
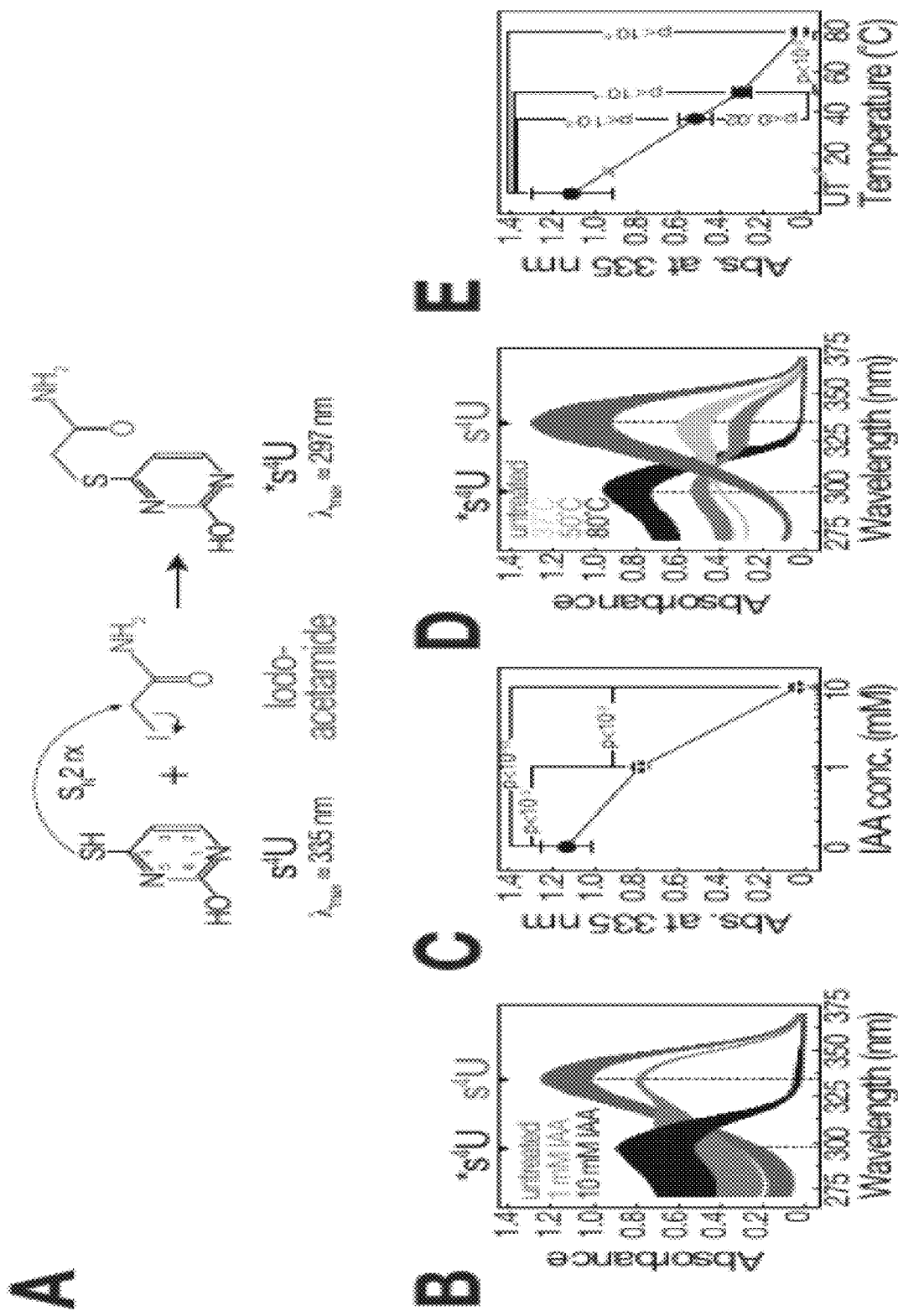
FIG. 2. 4-thiouracil-derivatization by thiol-linked alkylation. (A) 4-thiouracil ($s^4U$) reacts with the thiol-reactive compound iodoacetamide (IAA), attaching a carboxyamidomethyl-group to the thiol-group in $s^4U$ as a result of a nucleophilic substitution ($S_N2$) reaction. Absorption maxima of educt (4-thiouracil; $s^4U$; $\lambda_{max}≈335$ nm) and product (carboxyamidomethylated 4-thiouracil; $*s^4U$; $\lambda_{max}≈297$ nm) are indicated. (B) Absorption spectra of 4-thiouracil ($s^4U$) in the absence and presence of the indicated concentration of iodoacetamide (IAA). 1 mM $s^4U$ was incubated with the indicated concentration of IAA for 1 h at 37° C. in the presence of 50 mM sodium phosphate buffer (pH 8.0) and 10% DMSO. Data represents mean±SD of at least three independent replicates. (C) Quantification of absorption at 335 nm as shown in (B). P-values (Student's t-test) are indicated. (D) Absorption spectra of 1 mM 4-thiouracil ($s^4U$) in the absence and presence of 10 mM iodoacetamide (IAA) after incubation at the indicated temperature for 5 min in the presence of 50 mM sodium phosphate buffer (pH 8.0) and 10% DMSO. Data represents mean±SD of at least three independent replicates. (E) Quantification of absorption at 335 nm as shown in (D). P-values (Student's t-test) are indicated. (F) Absorption spectra of 1 mM 4-thiouracil ($s^4U$) in the absence and presence of 10 mM iodoacetamide (IAA) after incubation at 37° C. for the indicated time in the presence of 50 mM sodium phosphate buffer (pH 8.0) and 10% DMSO. Data represents mean±SD of at least three independent replicates. (G) Quantification of absorption at 335 nm as shown in (F). P-values (Student's t-test) are indicated. (H) Absorption spectra of 1 mM 4-thiouracil ($s^4U$) in the absence and presence of 10 mM iodoacetamide (IAA) after incubation at 50° C. for 2 min in the presence of 50 mM sodium phosphate buffer (pH 8.0) and the indicated amount of DMSO. Data represents mean±SD of at least three independent replicates. (I) Quantification of absorption at 335 nm as shown in (H). P-values (Student's t-test) are indicated. (J) Absorption spectra of 1 mM 4-thiouracil ($s^4U$) in the absence and presence of 10 mM iodoacetamide (IAA) after incubation at 50° C. for 5 min in the presence of 50 mM sodium phosphate buffer with the indicated pH and the 10% DMSO. Data represents mean±SD of at least three independent replicates. (K) Quantification of absorption at 335 nm as shown in (J). P-values (Student's t-test) are indicated. (L) Absorption spectra of 1 mM 4-thiouracil ($s^4U$) in the absence and presence of 10 mM iodoacetamide (IAA) after incubation at 50° C. for 15 min in the presence of 50 mM sodium phosphate buffer (pH 8.0) and 50% DMSO (optimal reaction [rxn] conditions). Data represent mean±SD of at least three independent replicates. (M) Quantification of absorption at 335 nm as shown in (J). P-values (Student's t-test) are indicated.
Figure 2:
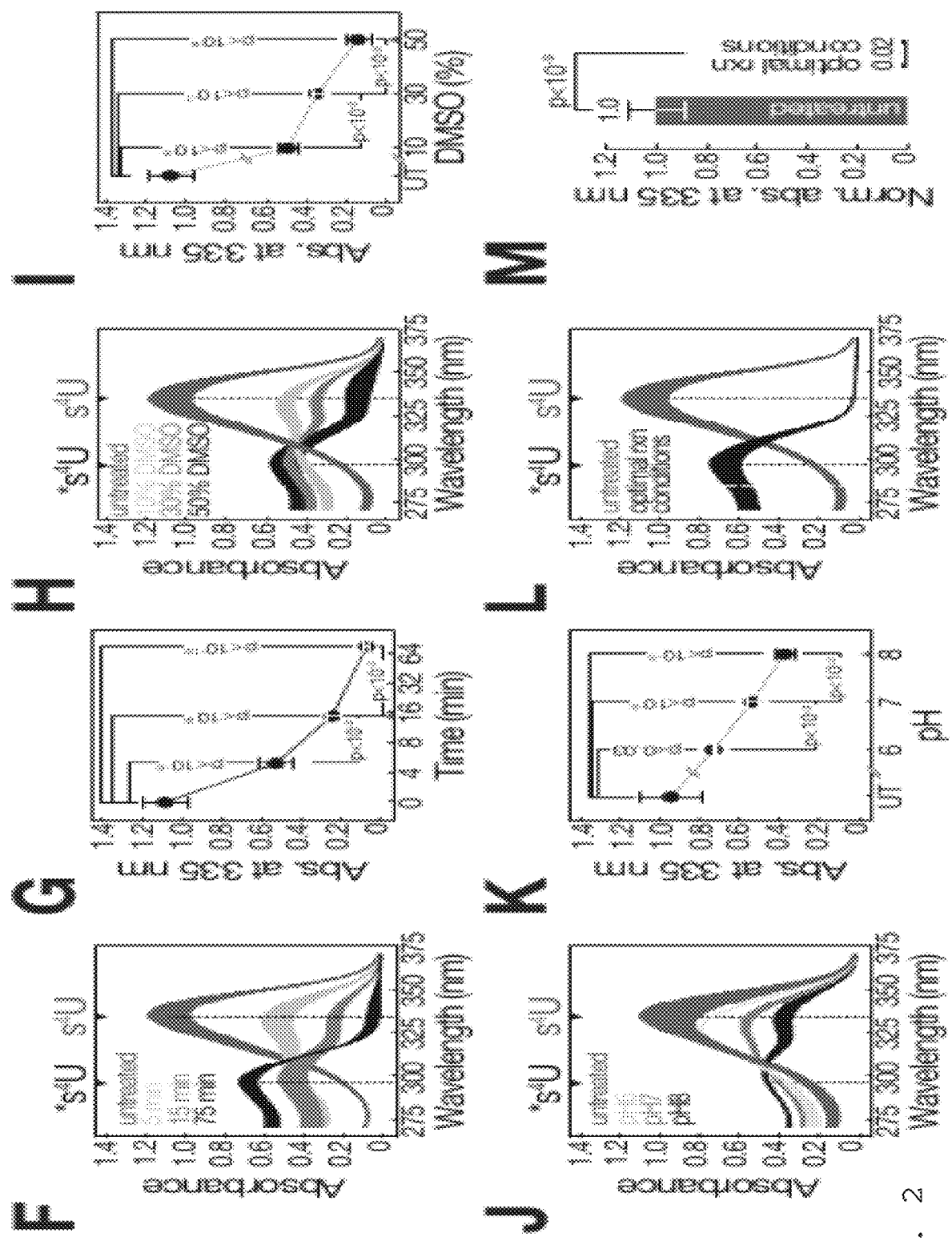
Figure 3:
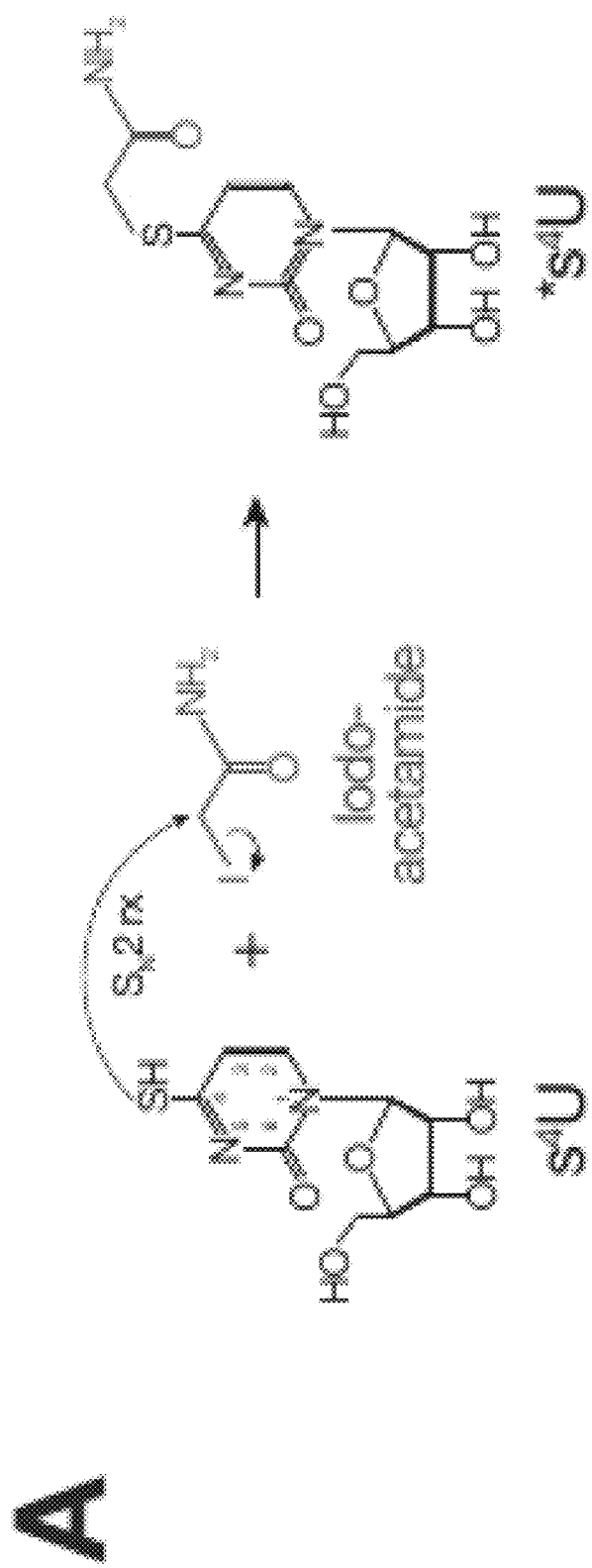
FIG. 3. 4-thiouridine-derivatization by thiol-linked alkylation. (A) 4-thiouridine ($s^4U$) reacts with the thiol-reactive compound iodoacetamide (IAA), attaching a carboxyamidomethyl-group to the thiol-group in $s^4U$ as a result of a nucleophilic substitution ($S_N2$) reaction. (B) Analysis of $s^4U$-alkylation by mass spectrometry. 40 nmol 4-thiouridine were incubated with the indicated concentration of iodoacetamide in standard reaction buffer (50 mM NaPO4 (pH 8), 50% DMSO) at 50° C. for 15 min. The reaction was stopped with 1% acetic acid. Acidified samples were separated on a Ultimate U300 BioRSLC HPLC system (Dionex; Thermo Fisher Scientific), employing a Kinetex F5 Pentafluorophenyl column (150 mm×2.1 mm; 2.6 μm, 100 Å; Phenomenex) with a flow rate of 100 μl/min. Nucleosides were on-line analyzed using a TSQ Quantiva mass spectrometer (Thermo Fisher Scientific) after electrospray ionization with the following SRMs: 4-Thiouridine m/z 260→129, alkylated 4-Thiouridine m/z 318→186. Data were interpreted using the Trace Finder software suite (Thermo Fisher Scientific) and manually validated. (C) Quantification of two independent experiments in two technical replicates shown in (B). Fraction alkylated $s^4U$ at indicated IAA concentrations represent relative normalized signal intensities at peak retention times of $s^4U$ and alkylated $s^4U$. Data represent mean±SD.
Figure 23:
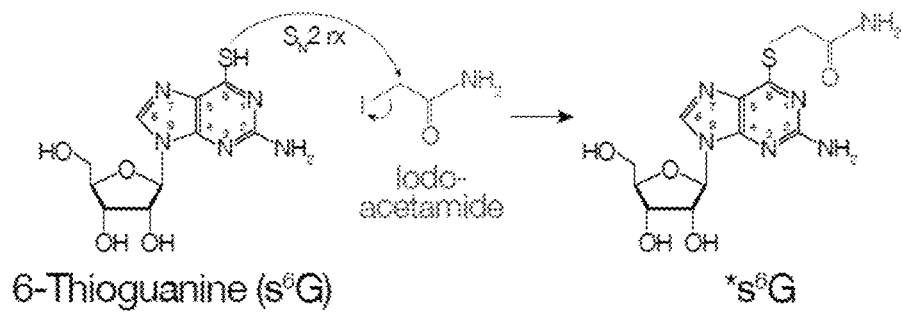
FIG. 23. Chemical modification of 6-thioguanosine ($s^6G$) with iodoacetamide. A chemical reaction of 6-thioguanosine with iodoacetamide (A) and the alkylation efficiencies as determined by mass-spectrometry upon treatment of 6-thioguanosine with iodoacetamide (B) are shown.
Figure 23:
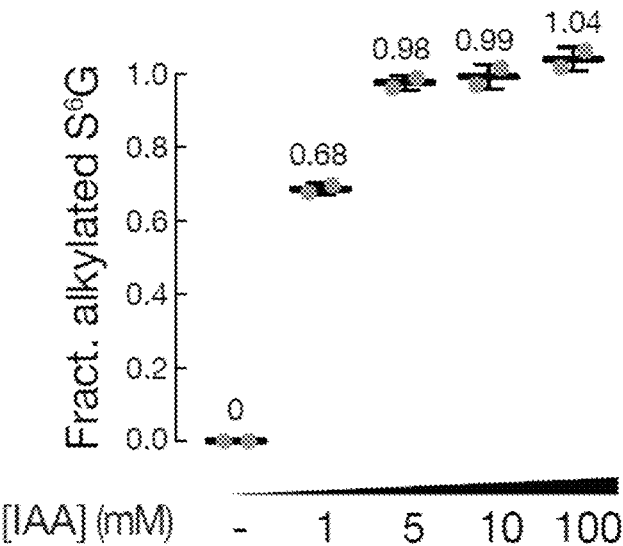

For $s^4$U-derivatization, we employed iodoacetamide (IAA) as an example of an effective primary thiol-reactive compound, attaching a carboxyamidomethyl-group to the thiol group as a result of a nucleophilic substitution ($S_N2$) reaction (FIG. 2A). A similar reaction occurs with other thiolated nucleobases, such as $s^6$G (FIG. 23A). To quantitatively monitor the efficiency of $s^4$U-derivatization as a function of different parameters (i.e. time, temperature, pH, IAA-concentration, and DMSO) we monitored the characteristic absorption spectrum of 4-thiouracil (~335 nm), which—upon reaction with iodoacetamide (IAA)—shifts to ~297 nm (FIG. 2B to K) (45). Under optimal reaction conditions (10 mM IAA; 50 mM NaPO$_4$, pH8; 50% DMSO; 50° C.; 15 min) absorption at 335 nm decreases 50-fold compared to untreated 4-thiouracil, resulting in an alkylation rate of at least 98% (FIGS. 2L and M). (Note, that conversion rates may be underestimated since the absorption spectrum of 4-thiouracil and its alkylated derivative partially overlap.) Analysis of thiol-specific alkylation in a ribose context (i.e. 4-thiouridine or 6-thioguanosine) by mass-spectrometry confirmed a close to complete derivatization efficiency (FIGS. 3 and 23B).

Figure 4:
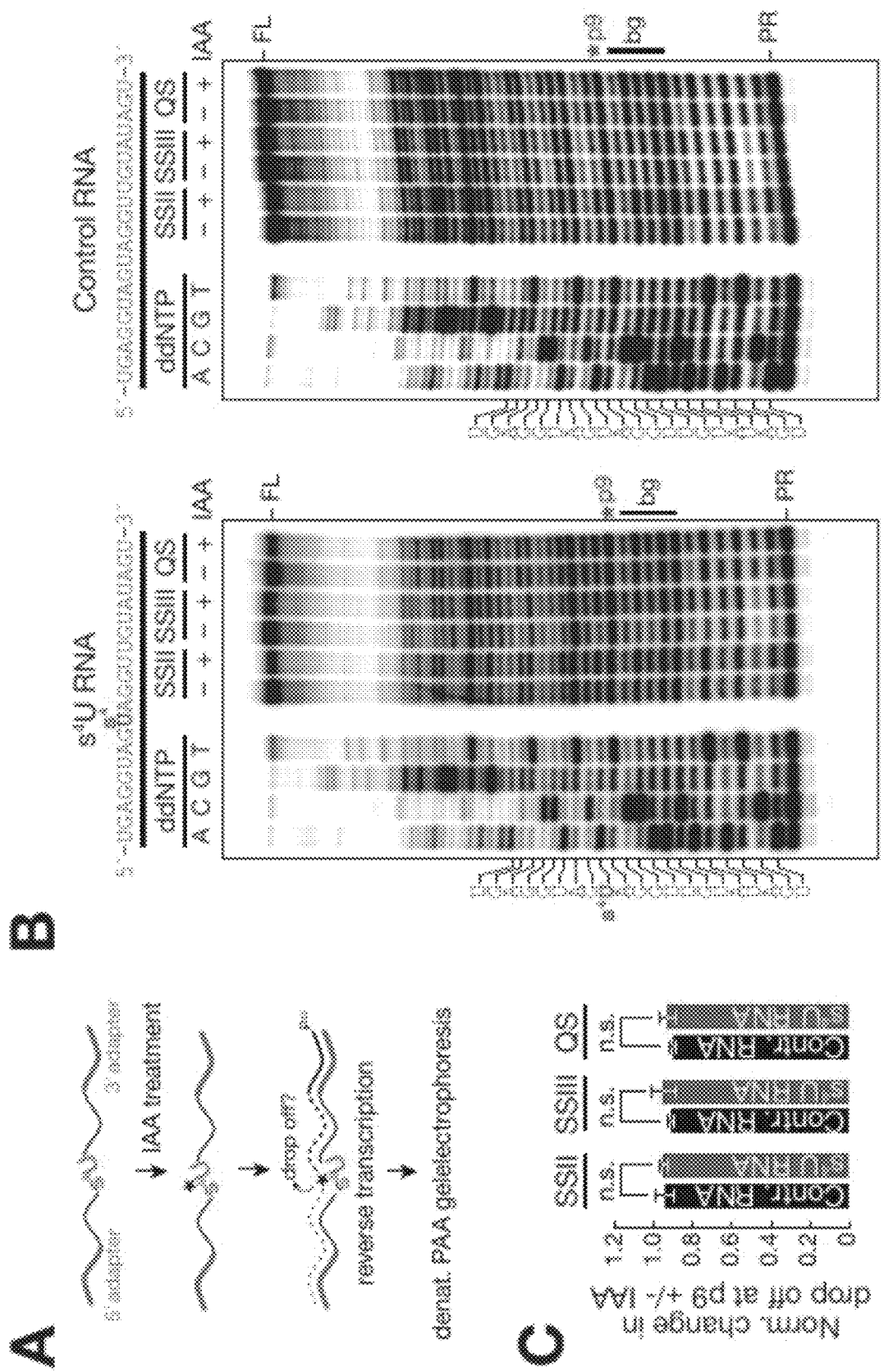
FIG. 4. Alkylation of 4-thiouridine-containing RNA does not affect reverse transcription processivity. (A) To determine the effect of $s^4U$-alkylation on reverse transcriptase-processivity we employed a synthetic 76 nt long RNA that contains 4-thiouridine ($s^4U$) incorporation at a single position (p9) within the sequence of the Drosophila small RNA dme-let-7, flanked by 5' and 3' adapter sequences. Reverse transcription was assayed before and after treatment with iodoacetamide (IAA) using commercially available reverse transcriptases by following the extension of a 5' $^{32}P$-labeled DNA oligonucleotide, reverse and complement in sequence to the 3'adapter sequence. (B) Reactions as prepared in (A) were analyzed by polyacrylamide gel electrophoresis followed by phosphorimaging. Primer extension results of $s^4U$-containing and non-containing RNA in the presence and absence of IAA-treatment, conducted with the reverse transcriptases Superscript II (SSII), Superscript III (SSIII) or Quant-seq RT (QS) are depicted. The sequence of the RNA component excluding adapter sequences are shown; the position of the $s^4U$ residue is indicated in red. RNA sequencing was performed by addition of the indicated ddNTPs to the reverse transcription reaction. PR, 5' $^{32}P$-labeled DNA primer; bg, background stop signal; *p9, termination signal at position 9; FL, full length product. (C) Quantification of three independent replicates of experiment shown in (B). Ratio of drop off signal (+vs−IAA treatment) at p9 after normalization to preceding background drop off signal was determined for control and $s^4U$-containing RNA employing the indicated reverse transcriptases. Data represent mean±SD. Statistical analysis was performed using Student's t-test.
Figure 24:
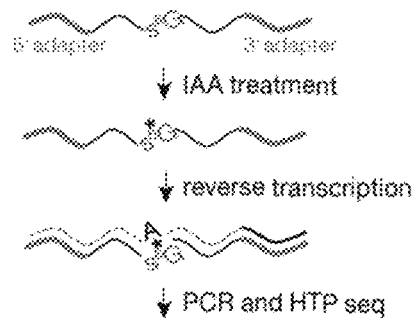
FIG. 24. Alkylation identifies $s^6G$-incorporations in RNA at single nucleotide resolution by G-to-A conversions. (A) RNA with or without 6-thioguanosine ($s^6G$) incorporation at a single position (p8) was treated with iodoacetamide (IAA) and subjected to reverse transcription and gel-extraction of full-length product followed by PCR amplification and high-throughput (HTP) sequencing. (B) Mutation rates for each position of a control RNA (left panels) and a $s^6G$-containing RNA (right panels) in the presence or absence of iodoacetamide (IAA) treatment employing the indicated reverse transcriptase are shown. Values represent average mutation rates ±SD of three independent replicates. Numbers of sequenced reads in each replicate (r1-r3) are indicated. Nucleotide identity occurrence at p8 is shown. (C) Mutation rates for the indicated mutations in the presence or absence of iodoacetamide (IAA) treatment employing Superscript II (SSII), Superscript III (SSIII), or Quant-seq reverse transcriptase (QS). Mutation rates were averaged across positions with the same nucleotide identity for both, $s^6G$-containing and non-containing RNA oligonucleotides. P-Values (determined by Student's t-test) are indicated. N.s., not significant (p>0.05).
Figure 24:
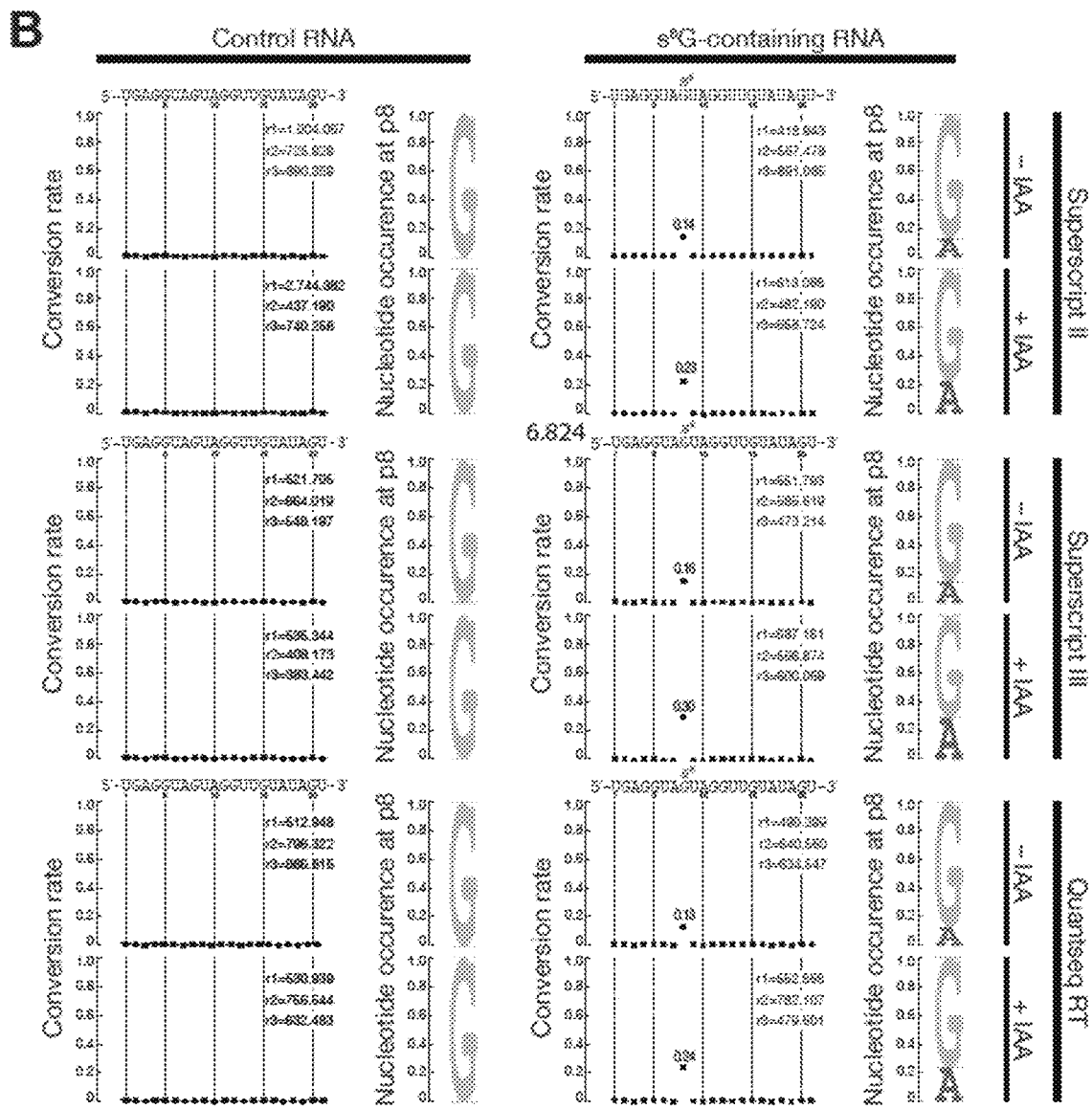
Figure 24:
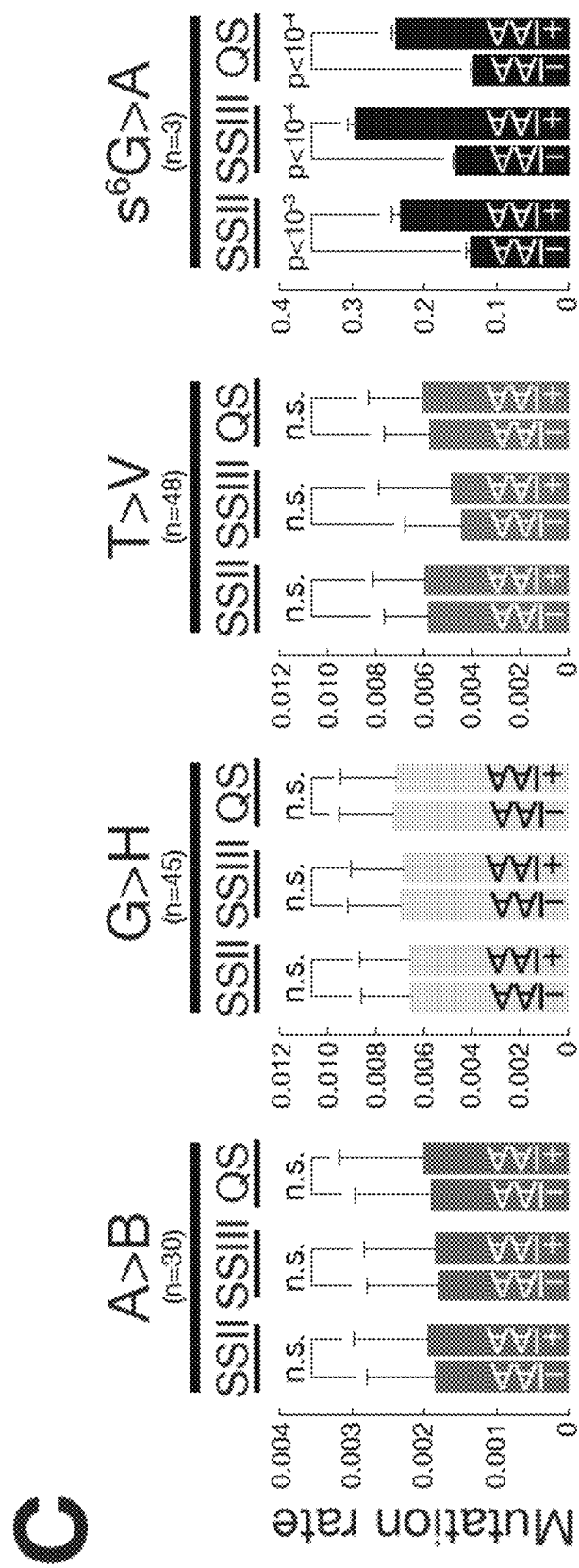

The quantitative recovery of $s^4$U or $s^6$G incorporation events presumes that reverse transcriptases pass alkylated $s^4$U-residues without drop-off. To determine the effect of $s^4$U- or $s^6$G-alkylation on reverse transcriptase-processivity we employed a synthetic RNA (for sequence see Example 1, Table) that contains a single $s^4$U or $s^6$G incorporation and assayed three commercially available reverse transcriptases (RTs)—Superscript II, Superscript III, and Quant-seq RT—in primer extension assays (FIG. 4A). When normalized to background drop-off signal, we did not observe a significant effect of $s^4$U- or $s^6$G-alkylation on RT processivity when compared to a non-$s^4$U- or non-$s^6$G-containing oligo with identical sequence (FIGS. 4B and C and FIG. 24B). We concluded that alkylation does not result in pre-mature termination of reverse transcription.

In order to evaluate the effect of $s^4U$- and $s^6G$-alkylation on reverse transcriptase-directed nucleotide incorporation, we isolated the full-length products of primer extension reactions, PCR amplified the cDNA and subjected the libraries to high-throughput sequencing using an Illumina HiSeq2500 instrument (FIGS. 5A and 24A). As expected, uridine was accurately reverse transcribed by all three RTs in the non-$s^4U$- or non-$s^6G$-containing control RNA, irrespective of its treatment with iodoacetamide with average mutation rates of less than $10^{-2}$ (FIGS. 5B and 24B, left panels). In contrast, the presence of $s^4U$ prompted a constant 10% to 11% T to C conversion even in the absence of alkylation, presumably due to base-pairing variations of $s^4U$-tautomeres (FIG. 5B, right top panels). In case of $s^6G$, a G to A conversion was observed (FIG. 24B, right panel). Notably, alkylation of $s^4U$ by iodoacetamide-treatment prompted an 8.5-fold increase in T to C conversion, resulting in a mutation rate of more than 0.94 across all tested RTs (FIG. 5B right bottom panels). When compared to reported sequencing errors in Illumina high-throughput sequencing datasets (below $10^{-3}$) we obtained a signal-to-noise ratio of >940:1. Importantly, we did not observe a significant effect of iodoacetamide-treatment on mutation rates of any given non-thiol-containing nucleotide (FIGS. 5C and 24C). We concluded that iodoacetamide treatment followed by reverse transcription enables the quantitative identification of $s^4U$- or $s^6G$-incorporations in RNA at single nucleotide resolution while not affecting the sequence information of non-thiol-containing nucleotides.

Figure 6:
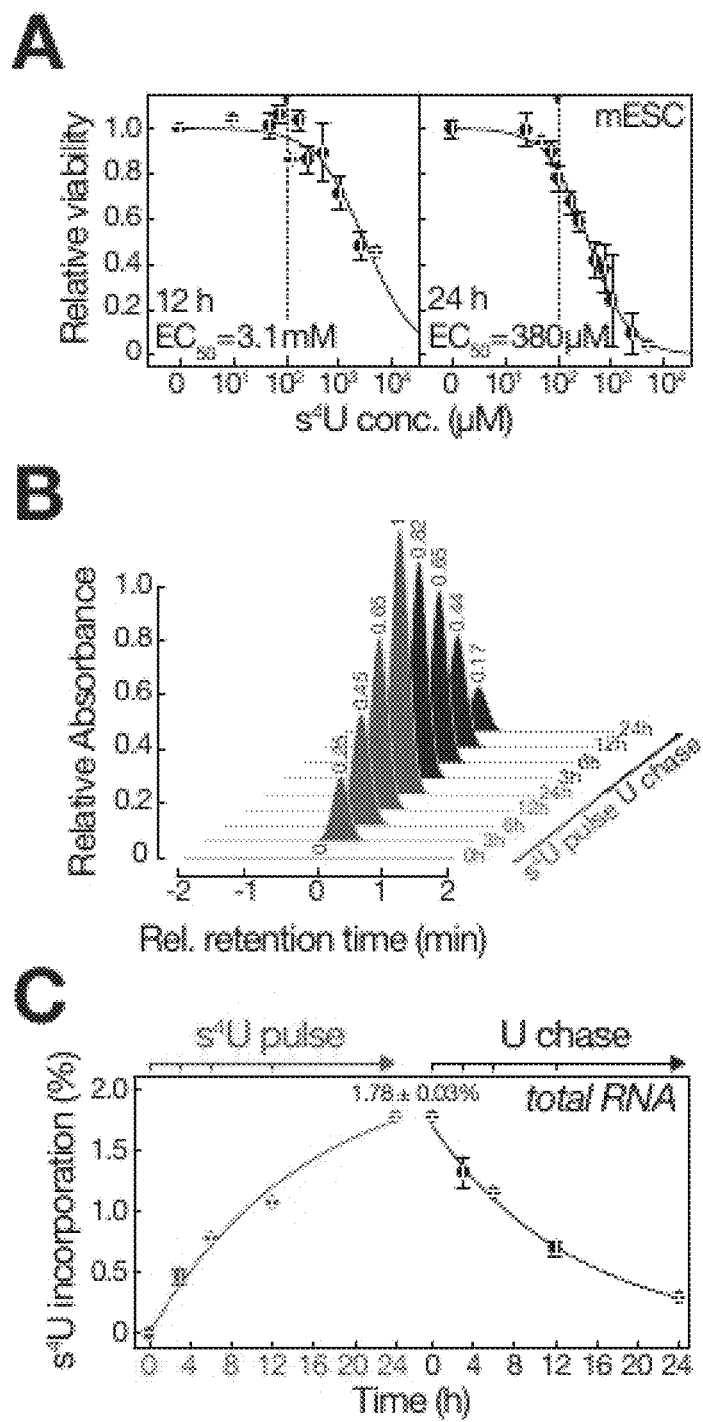
FIG. 6. Effect of $s^4U$ treatment on mES cell viability and metabolic RNA labeling. (A) Viability of mES cells cultured in the presence of the indicated concentration of 4-thiouridine ($s^4U$) for 12 h (left) or 24 h (right) relative to untreated conditions is shown. Final concentration used in subsequent experiments (100 μM) is indicated by triangle and dotted line. (B) Quantification of $s^4U$-incorporation into total RNA after $s^4U$-metabolic labeling for the indicated time in a pulse, or following media replacement in a uridine chase. $s^4U$-incorporation was determined by HPLC analysis following digestion and dephosphorylation of total RNA to single nucleosides. Background-subtracted $s^4U$ signal intensities at 330 nm normalized to 24 h pulse labeling timepoint and absorbance of uridine signal intensities at 260 nm is shown. Column retention time (min) relative to $s^4U$-adsorption maxima is shown. (C) Substitution rate of $s^4U$ compared to unmodified uridine determined by HPLC. $s^4U$ incorporation in total RNA across all timepoints of a $s^4U$-metabolic pulse and chase labeling experiment in mES cells. Values represent mean±SD of three independent replicates. Maximum incorporation rates after 24 h labeling are indicated.

Example 3: Incorporations of Modified Nucleotides in Metabolically Labeled mRNA in mES Cells We tested the ability of mouse embryonic stem cells to tolerate $s^4U$ metabolic RNA-labeling after 12 h or 24 h at varying $s^4U$ concentrations (FIG. 6A). As reported previously, high concentrations of $s^4U$ compromised cell viability with an $EC_{50}$ of 3.1 mM or 380 µM after 12 h or 24 h labeling, respectively (FIG. 6A). Hence, we employed labeling conditions of 100 µM $s^4U$, which did not severely affect cell viability. Under these conditions, we detected a steady increase in $s^4U$-incorporation in total RNA preparation 3 h, 6 h, 12 h, and 24 h post labeling, as well as a steady decrease 3 h, 6 h, 12 h, and 24 h after uridine chase (FIG. 6B). As expected, the incorporation follows a single exponential kinetics, with a maximum average incorporation of 1.78% $s^4U$, corresponding to one $s^4U$ incorporation in every 56 uridines in total RNA (FIG. 6C). These experiments establish $s^4U$-labeling conditions in mES cells, which can be employed to measure RNA biogenesis and turnover rates under unperturbed conditions.

Figure 7:
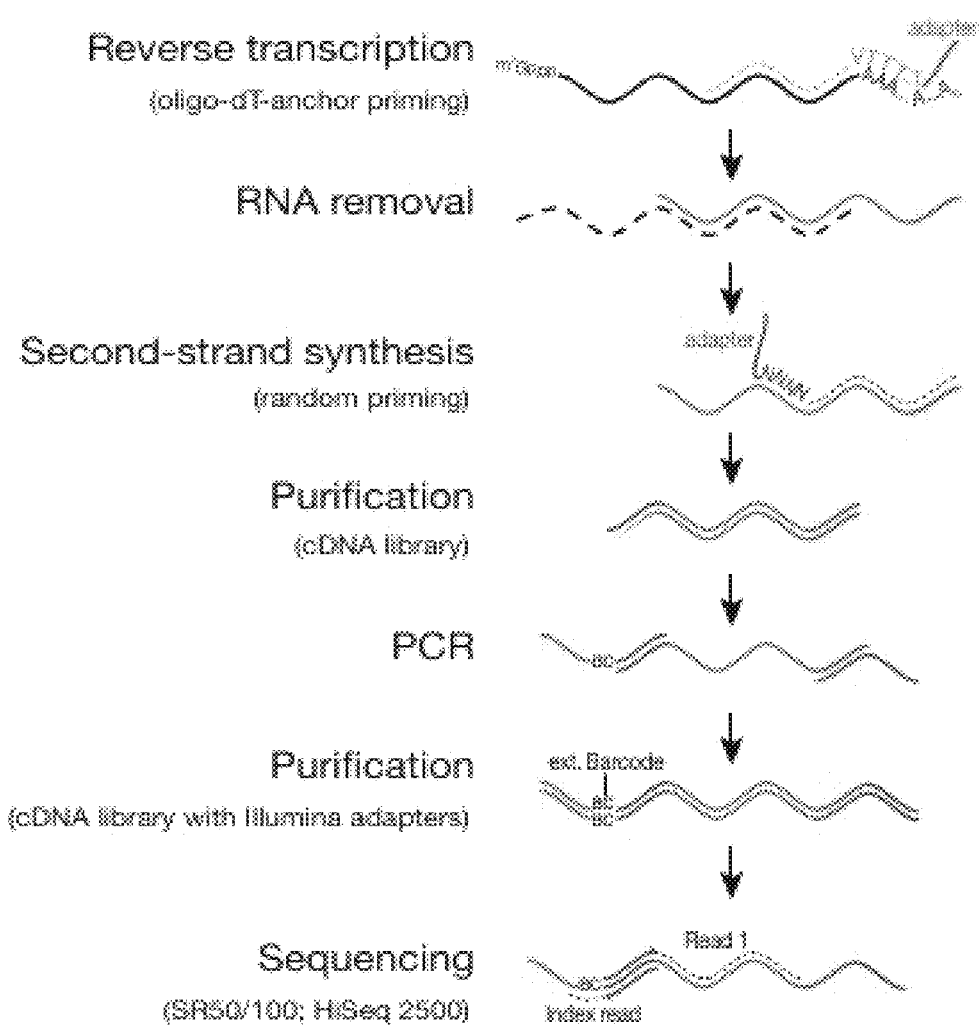
FIG. 7. Quant-seq mRNA 3' end sequencing library preparation protocol. Quant-seq uses total RNA as input, hence no prior poly(A) enrichment or rRNA depletion is required. Library generation is initiated by oligo(dT) priming. The primer already contains Illumina-compatible linker sequences (shown in green, top: "adapter", next step: last bend). After first strand synthesis the RNA is removed and second strand synthesis is initiated by random priming and a DNA polymerase. The random primer also contains Illumina-compatible linker sequences (shown in blue). No purification is required between first and second strand synthesis. The insert size is optimized for shorter reads (SR50 or SR100). Second strand synthesis is followed by a magnetic bead-based purification step. The library is then amplified, introducing the sequences required for cluster generation (shown in red and purple). External barcodes (BC) are introduced during the PCR amplification step for multiplexing.
Figure 8:
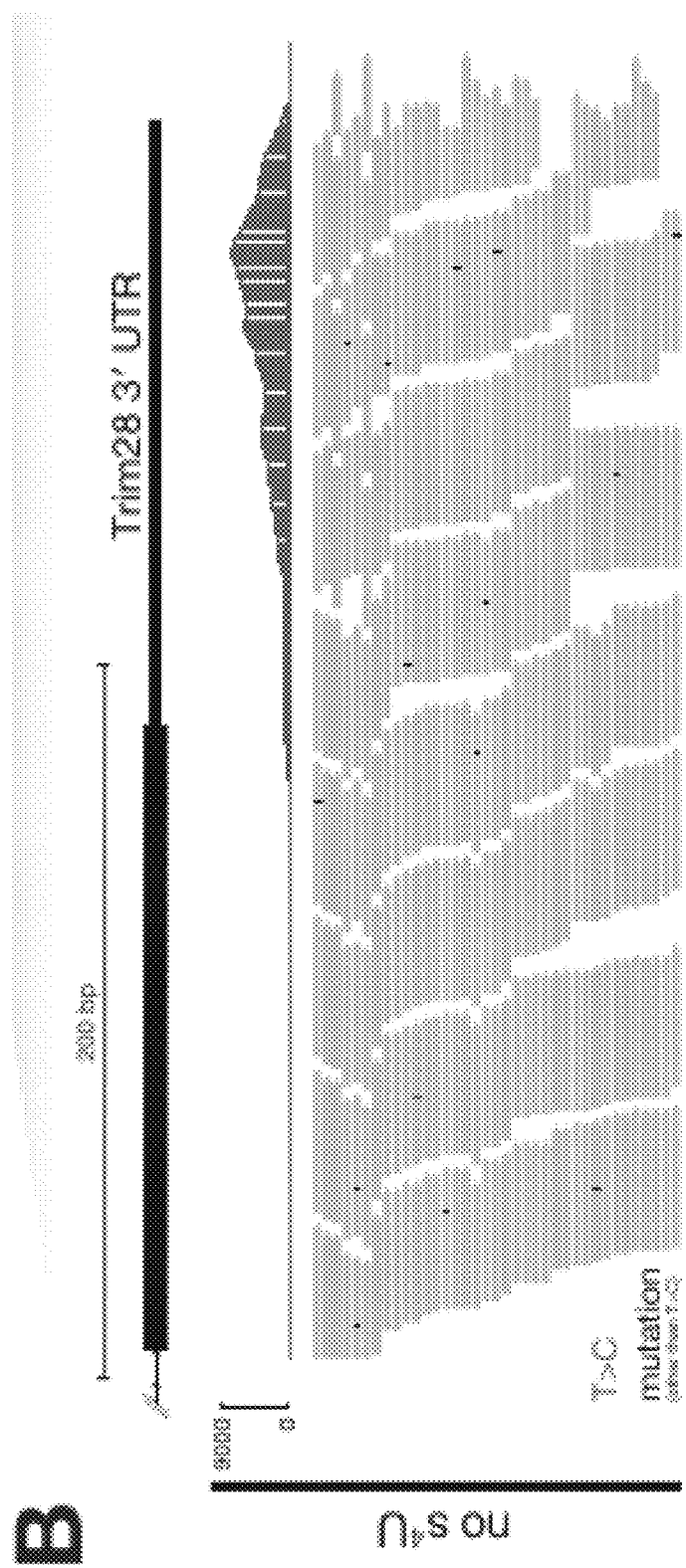
FIG. 8. $s^4U$ incorporation events in mRNA of mES cells upon metabolic labeling. (A) Representative genome browser screen shot for three independent mRNA libraries generated from total RNA of mES cells, prepared using standard mRNA sequencing (top three panels), Cap analysis gene expression (CAGE; middle three panels) and mRNA 3' end sequencing (bottom three panels). A representative area in the mouse genome encoding the gene Trim 28 is shown. (B) Zoom into the genome area encoding the mRNA 3' end of Trim28 including its 3'untranslated region (UTR). Coverage plots of mRNA 3' end sequencing libraries prepared from total RNA of untreated mES cells or mES cells subjected to $s^4U$-metabolic labeling for 24 h followed by modification and sequencing are shown. A subset of individual reads underlying the coverage plots is depicted. Red bars within individual reads represent T>C conversions; black bars represent any mutation other than T>C.

To test the ability of the method to uncover $s^4U$ incorporation events in high throughput sequencing datasets we generated mRNA 3' end libraries (employing Lexogen's QuantSeq, 3' mRNA-sequencing library preparation kit) using total RNA prepared from cultured cells following $s^4U$-metabolic RNA labeling for 24 h (FIG. 7) (Moll et al., supra). Quant-seq 3' mRNA-Seq Library Prep Kit generates Illumina-compatible libraries of the sequences close to the 3'end of the polyadenylated RNA, as exemplified for the gene Trim28 (FIG. 8A). In contrast to other mRNA-sequencing protocols, only one fragment per transcript is generated and therefore no normalization of reads to gene length is needed. This results in accurate gene expression values with high strand-specificity.

Figure 9:
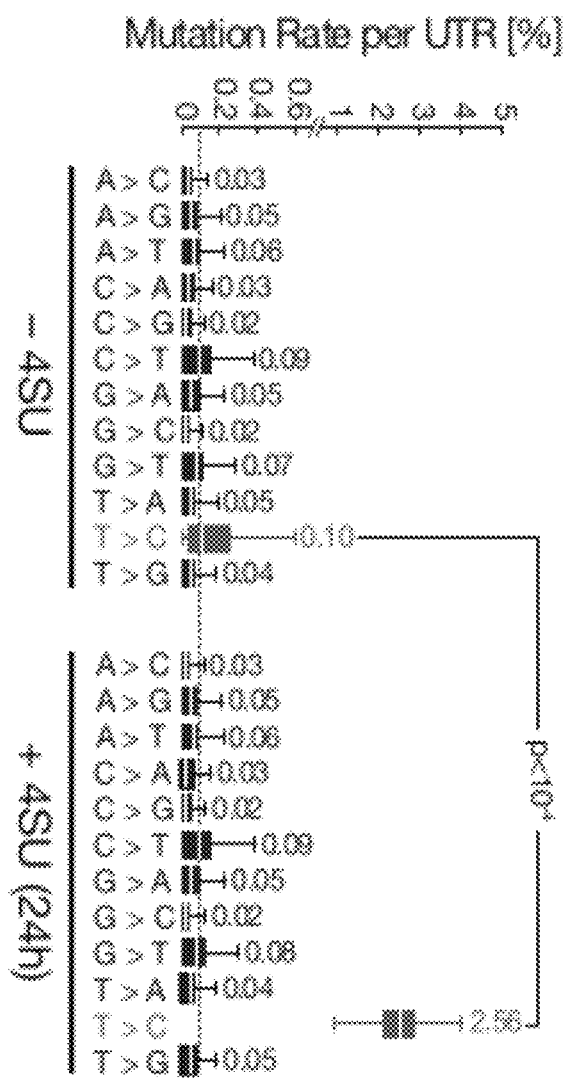
FIG. 9. Global analysis of mutation rates in mRNA 3' end sequencing following $s^4U$ metabolic RNA labeling in mES cells. mRNA 3' end sequencing libraries generated from total RNA of mES cells before and after $s^4U$ metabolic labeling for 24 h were mapped to annotated 3' untranslated regions (UTRs) and any given mutation rate was determined for all expressed genes. Tukey boxplots show mutations per UTR in percent. Outliers are not shown. Median observed frequency for each individual mutation is indicated. Statistical analysis of increase in T>C conversions was determined by Mann-Whitney test.

Furthermore, sequencing-ready libraries can be generated within only 4.5 h, with ~2 h hands-on time. When combined with the invention, Quant-seq facilitates the accurate determination of mutation rates across transcript-specific regions because libraries exhibit a low degree of sequence-heterogeneity. Indeed, upon generating libraries of U-modified RNA through the Quant-seq protocol from total RNA of mES cells 24 h after $s^4U$ metabolic labeling we observed a strong accumulation of T>C conversions when compared to libraries prepared from total RNA of unlabeled mES cells (FIG. 8B). In order to confirm this observation transcriptome-wide, we aligned reads to annotated 3' UTRs and inspected the occurrence of any given mutation per UTR (FIG. 9). In the absence of $s^4U$ metabolic labeling, we observed a median mutation rate of 0.1% or less for any given mutation, a rate that is consistent with Illumina-reported sequencing error rates. After 24 h of $s^4U$ metabolic labeling, we observed a statistically significant ($p<10^{-4}$, Mann-Whitney test), 25-fold increase in T>C mutation rates, while all other mutations rates remained below expected sequencing error rates (FIG. 9). More specifically, we measured a median $s^4U$-incorporation of 2.56% after 24 h labeling, corresponding to one $s^4U$ incorporation in every 39 uridines. (Note, that median incorporation frequency for mRNA are higher than estimated by HPLC in total RNA [FIG. 6C], most certainly because stable non-coding RNA species, such as rRNA, are strongly overrepresented in total RNA.) These analyses confirm that the new method uncovers $s^4U$-incorporation events in mRNA following $s^4U$-metabolic RNA labeling in cultured cells.

We expect the same incorporation results of other modified nucleotides, such as $s^6G$ or 5-ethynyluridine, as reported previously (Eidinoff et al., Science. 129, 1550-1551 (1959); Jao et al. PNAS 105, 15779-15784 (2008); Melvin et al. Eur. J. Biochem. 92, 373-379 (1978); Woodford et al. Anal. Biochem. 171, 166-172 (1988)).

Example 4: Use of 5-Bromo-Uridine and pH-Dependent Base-Pairing Frequencies During Reverse Transcription Yu et al. (The Journal of Biological Chemistry, 268:21, 15935-15943, 1993) demonstrated that the base analogue bromouracil forms mispairs with G (guanine) as a function of pH during polymerization. Further, it has been shown that 5BrU is taken up by cells, phosphorylated, and incorporated into nascent RNA (Larsen et al., Current Protocols in Cytometry. 12 (7.12): 7.12.1-7.12.11, 2001). We demonstrate that both can be used to identify 5BrU-labelling by pH-variant NGS library preparations and sequencing. We used 100 µmol of the synthetic RNA oligonucleotide which contained a 5BrU modification at a single central position. The RNA sequence 5"-<u>ACACUCUUUCCCUA</u>-CACGACGCUCUUCCGAUCUUGAGGUAGU[5BrU] AGGUUGUAUAGUA<u>GAUCGGAAGAGCACACGU-CUC</u>-3" (SEQ ID NO: 8) possesses two underlined linker sequences which were used for reverse transcription and amplification, and [5BrU], 5-Bromouridine label in central position. The reverse transcription was performed by Superscript II (Thermo Fisher Scientific) according to the instructions of the manufacturer using the RT DNA oligonucleotide primer (5"-GTGACTGGAGTTCA-GACGTGTGCTCTTCCGATCT-3", SEQ ID NO: 9) and 5×RT buffer for which pH was adjusted to pH7, pH8, or pH9, respectively. After reverse transcription, 1 µmol reverse transcription product was subjected to PCR amplification using KAPA Real-time Library Amplification Kit (KAPA Biosystems) according to the instructions of the manufacturer, using the DNA oligonucleotides Solexa PCR Fwd (5"-AATGATACGGCGACCACCGAGATCTA-CACTCTTTCCCTACACGACGCTCTTCCGATCT-3', SEQ ID NO: 10) and Solexa IDX rev (5'-CAAGCAGAA-GACGGCATACGAGATNNNNNNGTGACTG-GAGTTCAGACGTGTGCTCTTCCGATCT-3', SEQ ID NO: 11; NNNNNN indicates the position of the barcode-nucleotides). The amplified libraries were sequenced by high-throughput sequencing using the Illumina MiSeq platform. The conversion rates for the 5BrU nucleotide were determined by counting the frequency of nucleotide A (adenine), G (guanine), and C (cytosine) other than the expected majority readout of T (thymine) at the position of 5BrU.

The pH-dependent conversion rates of 5BrU, or T in the final readout, to A (T>A conversion) show a 1.1-fold and 1.4-fold increase with an increase of pH during reverse transcription to pH 8 and pH 9 respectively compare to the background conversion rate of $3 \cdot 10^{-4}$ at pH 7 (FIG. 37C). The T>G conversion increases by 1.2- and 1.9-fold compare to the lower background conversion rate of $1 \cdot 10^{-4}$ at pH 7. In contrast, the T>C conversion rate increases by 2.2-fold and 4.3-fold compare to the background conversion rate of $3 \cdot 10^{-4}$ at pH 7. The signature of the pH dependent changes in conversion rates is characteristic for the 5BrU in the RNA and can be used to identify the number of 5BrU which are incorporated into nascent RNA during transcription.

Example 5: Determining the Poly-Adenylated Transcriptional Output in mES Cells

Figure 10:
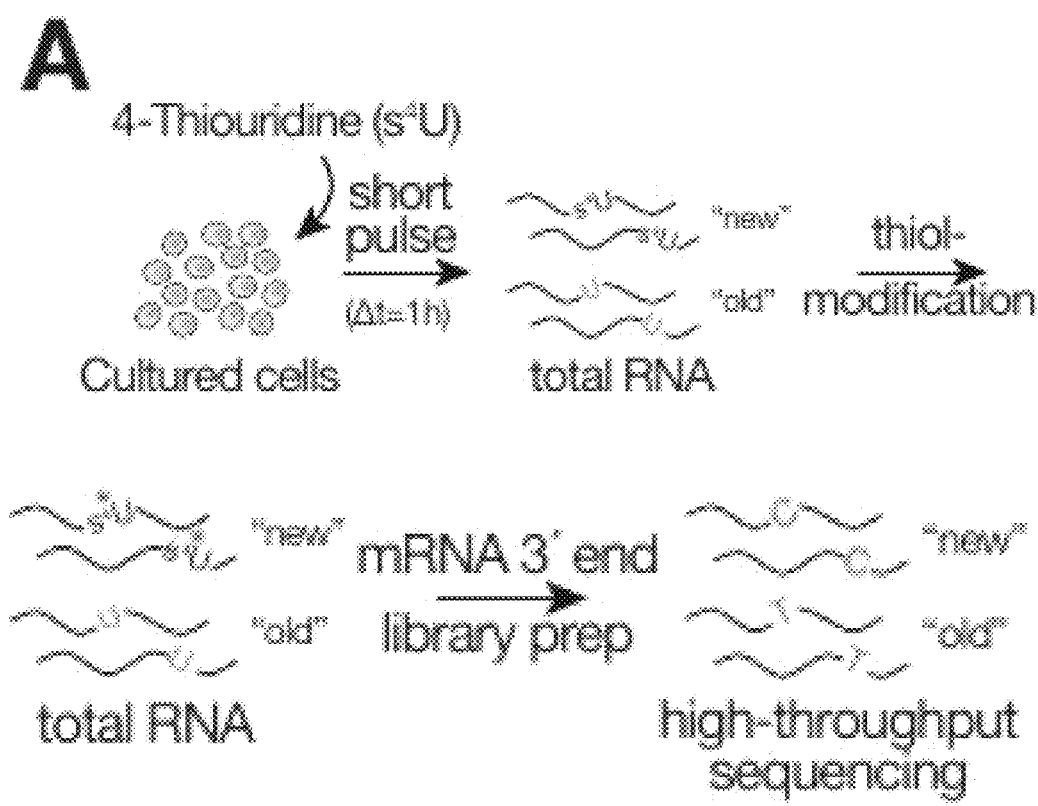
FIG. 10. Determining the poly-adenylated transcriptional output in mES cells. (A) Experimental setup to determine the transcriptional output of poly-adenylated mRNA in mES cells by the invention. (B) Relative abundance of T>C conversion containing transcripts ("SLAM-seq") and non-T>C conversion containing transcripts ("Steady-state") in counts per million (cpm), detected by mRNA 3' end sequencing as described in (A). Transcripts overrepresented in SLAM-seq relative to steady-state are indicated in red (high transcriptional output; n=828). Most abundant transcripts at steady-state are indicated in yellow (high steady state expression; n=825). Transcripts corresponding to mES cell specific primary-miRNA clusters miR-290 and miR-182 are shown. (C) Comparison of 828 genes that were overrepresented among newly transcribed RNA (SLAM-seq) to the top 825 genes detected at steady-state by conventional mRNA 3' end sequencing (Steady-state) in terms of predicted underlying transcription factors (using Ingenuity Pathway Analysis; www.Ingenuity.com), as well as molecular pathways (using Enrichr).
Figure 10:
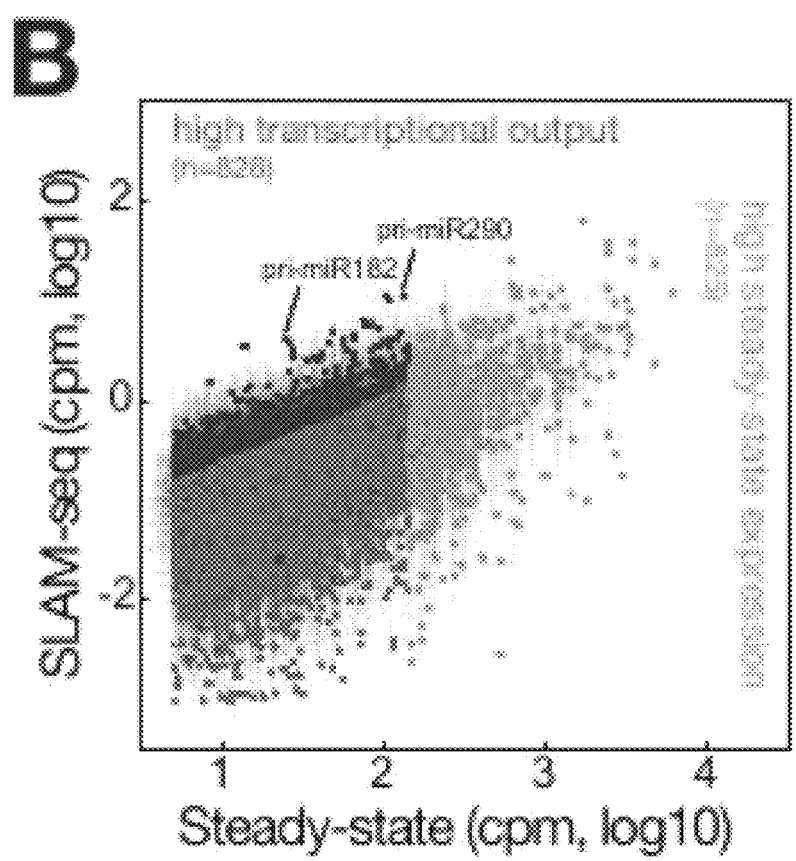
Figure 10:
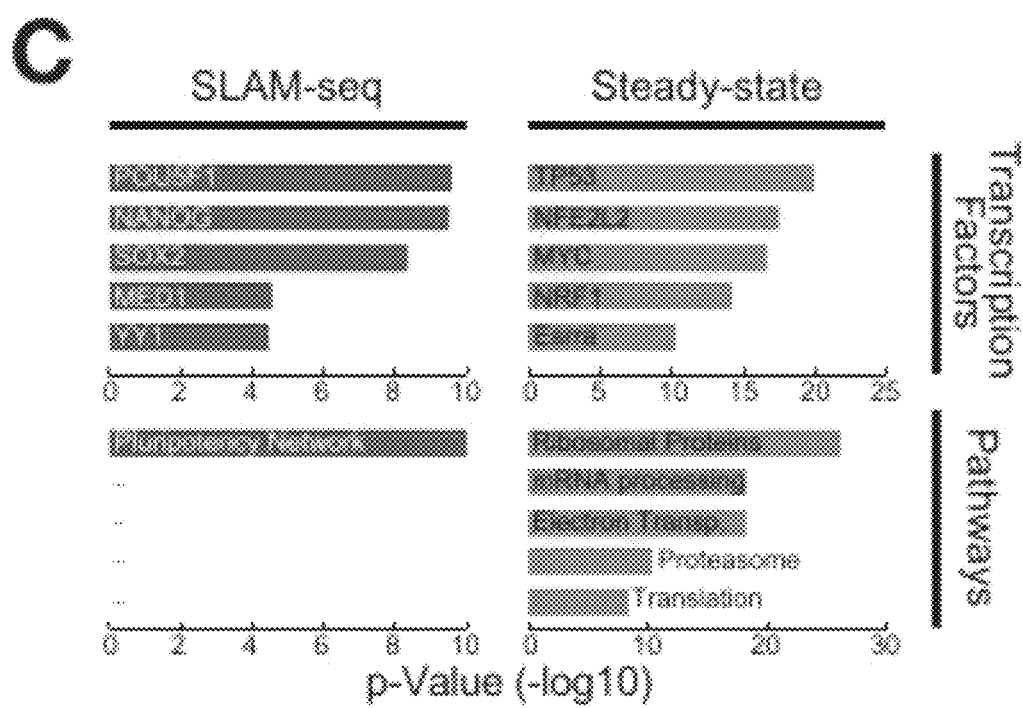

To test if short $s^4U$ pulse labeling followed by mRNA 3' end sequencing accurately reports the poly-adenylated transcriptional output, we subjected mES cells to a short, 1 h $s^4U$-pulse followed by total RNA extraction and mRNA 3' end library preparation (FIG. 10A). Quant-seq-generated libraries were mapped to annotated 3' UTRs in the mouse genome and analyzed for the presence of T>C conversions, representing newly transcribed RNA (FIG. 10A). When comparing the relative abundance of newly transcribed (i.e. T>C conversion containing) to steady-state (i.e. T>C and non-T>C conversion containing) poly-adenylated transcripts, we observed a subset of transcripts consisting of 828 genes that were over-represented among newly transcribed RNA (FIG. 10B). Among the top over-represented transcripts were mES cell-specific microRNA clusters (miR-290- and miR182 cluster), which are thought to be particularly short-lived because they undergo rapid decay upon excision of microRNA hairpins by Drosha in the nucleus, hence do not accumulate to high levels at steady-state (FIG. 10B). To more systematically characterize the de novo transcriptional output measured by the new method, we performed gene list enrichment analysis of the 828 genes that were over-represented among newly transcribed RNA as well as the top 825 genes detected at steady-state by conventional mRNA 3' end sequencing in terms of predicted underlying transcription factors (using Ingenuity Pathway Analysis, www.Ingenuity.com), as well as associated molecular pathways (using Enrichr) (FIG. 10C): As expected, high-level steady-state expression failed to predict the pluripotency-associated transcription factor network and mostly associated with house-keeping pathways, such as ribosomal proteins, mRNA processing or electron transport. In contrast, de novo transcript analysis by the inventive method successfully predicted key mES cell-specific transcription factors, including Oct4 (POU5F1), NANOG and SOX2, as well as the pluripotency network (FIG. 10C). We concluded that short $s^4U$-pulse labeling in combination with RNA modification and mRNA 3' end sequencing enables to uncouple the immediate transcriptional output from transcript stability effects, hence provides a rapid and scalable method to study transcriptional gene regulation.

Example 6: Measuring mRNA Transcript Stabilities

Figure 11:
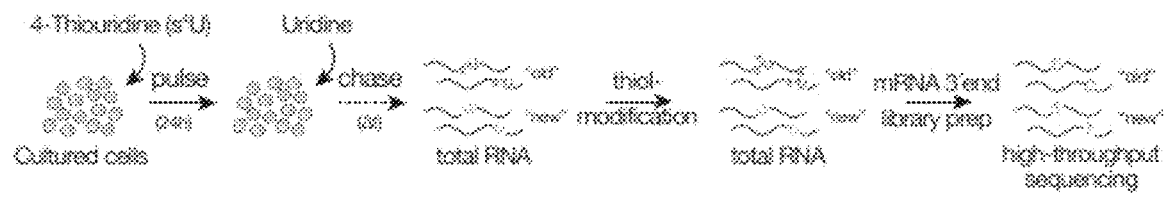
FIG. 11. Global analysis of mRNA stability in mES cells. (A) Experimental setup to determine the stability of poly-adenylated mRNA in mES cells by the invention. (B) Global analysis of mRNA half-lives in mES cells. The relative fraction of T>C conversion containing reads mapping to annotated 3' UTRs of 9430 abundantly expressed genes in mES cells were normalized to the 24 h pulse labeling timepoint and median, upper and lower quartiles over time were fit using single exponential decay kinetics, revealing a median mRNA half-life ($~t_{1/2}$) of 4.0 h. (C) Half-life calculation for individual example transcripts. The average fraction of T>C conversion containing reads relative to 24 h pulse timepoint of three independent replicates for Junb, Id1, Eif5a and Ndufa7 are shown and fit to single exponential decay kinetics. The average half-life ($t_{1/2}$) for each transcript as determined by curve fitting is indicated. (D) Tukey boxplot representation of mRNA half-life determined by mRNA 3' end sequencing for transcripts classified according to their associated GO-terms into regulatory (i.e. transcriptional regulation, signal transduction, cell cycle and development) or house-keeping (i.e. extracellular matrix, metabolic process and protein synthesis). The number of transcripts for each category are indicated. P-value (determined by Mann-Whitney test) is indicated.
Figure 11:
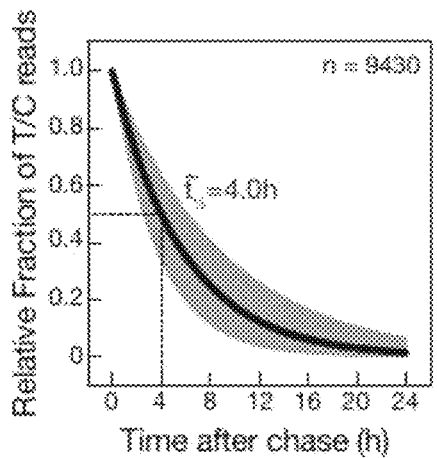
Figure 11:
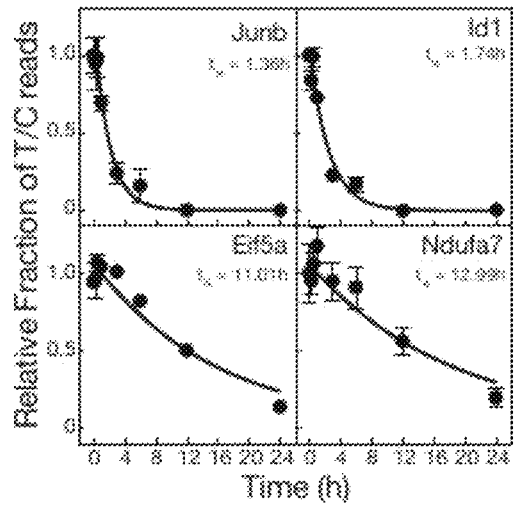
Figure 11:
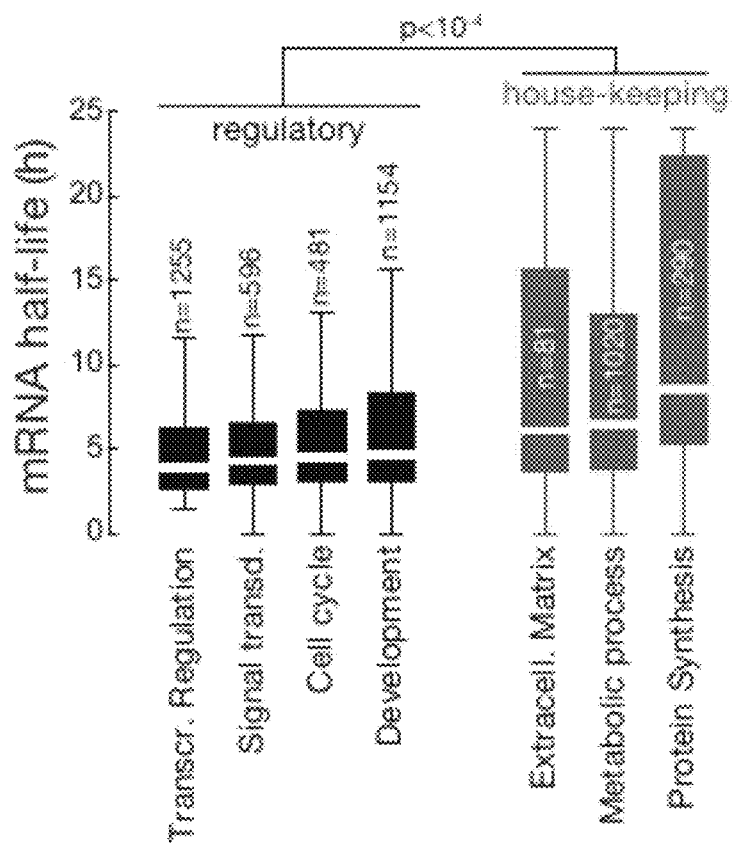

To determine if the inventive method can be employed to measure mRNA transcript stabilities we performed $s^4U$ labeling of RNA in mES cells for 24 h, followed by a chase using an excess of non-thiol containing uridine, and prepared total RNA at various timepoints (0 min, 15 min, 30 min, 1 h, 3 h, 6 h, 12 h, and 24 h) followed by U-modification and mRNA 3' end sequencing (FIG. 11A). Again, we mapped libraries to annotated 3' UTRs in the mouse genome and analyzed them for the presence of T>C conversions, representing old transcripts (FIG. 11A). A global analysis of T>C conversion containing transcripts over time, normalized to steady-state abundance (which remained constant in the course of the analysis) for 9430 genes revealed a median mRNA half-life of 4 h (FIG. 11B). As expected, the half-life of individual transcripts varied by more than one order of magnitude (FIG. 11C).

Control over mRNA stability is essential for the temporal order of gene expression. The new method recapitulated the key underlying principles, because regulatory transcripts, associated with GO terms such as 'transcriptional regulation', 'signal transduction', 'cell cycle', or 'development' exhibited significantly shorter half-lives compared to house-keeping transcripts, falling into GO-terms such as 'extracellular matrix', 'metabolic process', or 'protein synthesis' (FIG. 11D). In conclusion, the invention enables the accurate assessment of mRNA stability, providing a convenient method to study post-transcriptional gene regulation. As shown, the method recapitulates global post-transcriptional gene regulatory signatures in mouse embryonic stem cells.

Example 7: Thiol-Linked Alkylation for the Metabolic Sequencing of Small RNAs

To gain insights into the intracellular kinetics of small RNA silencing pathways, we applied a nucleotide-analog derivatization strategy that bypasses the need for biochemical isolation of labeled RNA species and enables the determination of RNA biogenesis, and turnover kinetics in the context of total RNA (FIG. 12): This strategy is based on a well-established 4-thiouridine ($s^4U$) metabolic RNA labeling approach but replaces the ineffective and experimentally challenging biotinylation-step with a short chemical treatment that involves the reaction of $s^4U$-containing RNA with iodoacetamide, a sulfhydryl-reactive compound, which—upon reaction with $s^4U$—creates a covalently linked amidomethyl-group at the base-pairing interface (FIG. 1). When combined with conventional RNA library preparation protocols, such as small RNA sequencing, the presence of the bulky group at the sites of $s^4U$-incorporation leads to the specific and quantitative misincorporation of G during reverse transcription (RT), but does not interfere with RT-processivity. $s^4U$-incorporation events can be identified by sequence comparison, usually bioinformatically in high-throughput sequencing libraries at single nucleotide resolution and in the context of unlabeled RNA by calling T to C transitions, hence eliminates the need for spike-in solutions to measure absolute labeling efficiencies. Importantly, no enzyme that converts uridine to cytosine is known and T>C error rates in high throughput RNA sequencing datasets using e.g. the Illumina HiSeq 2500 platform are rare, occurring at a frequency of less than one in ten thousand. We refer to this approach as thiol(SH)-linked alkylation for the metabolic sequencing of small RNAs.

Figure 12:
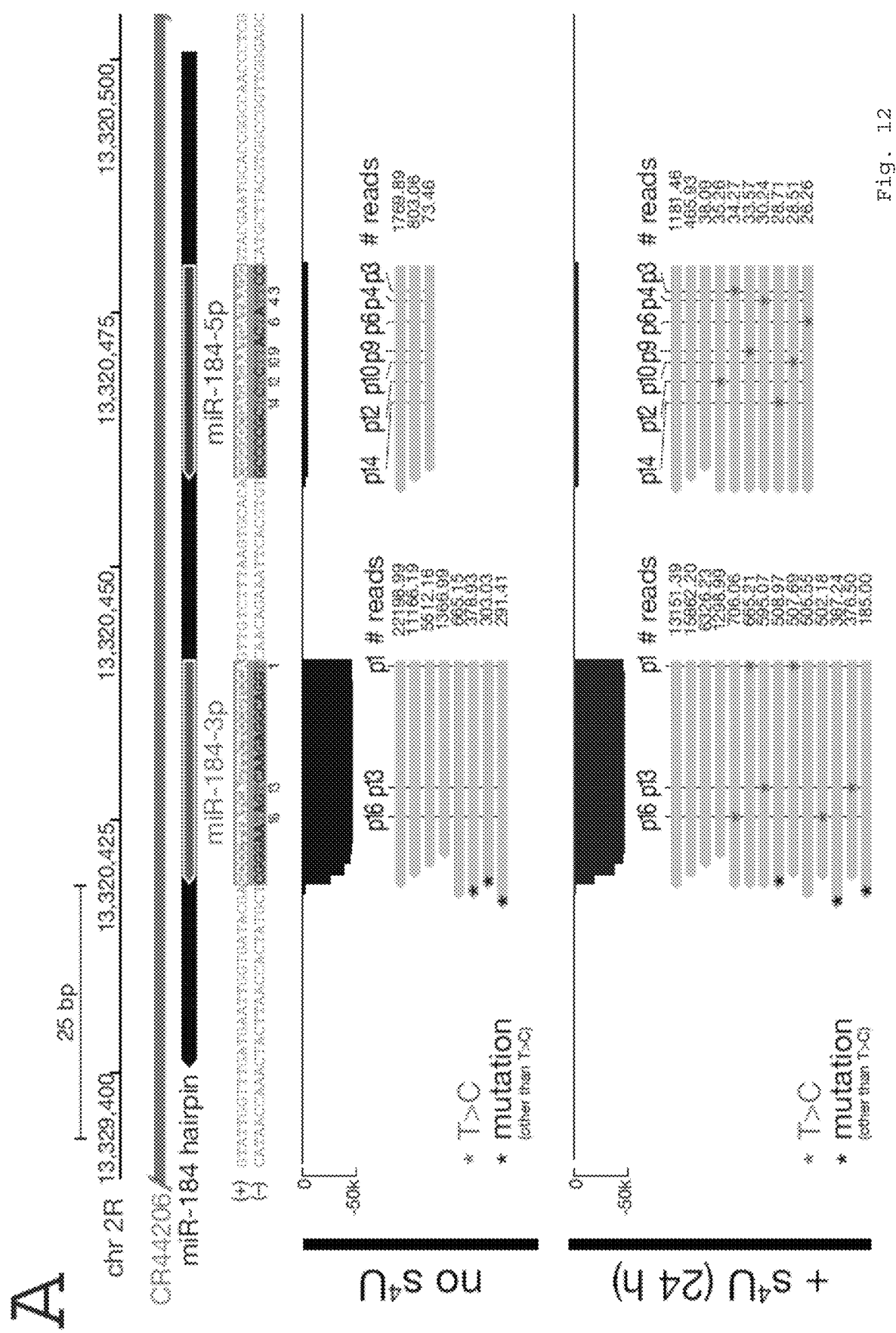
FIG. 12. Thiol-linked alkylation for the metabolic labeling of small RNAs. (A) Representative genome browser screen shot for small RNA libraries generated from size-selected total RNA of Drosophila S2 cells. A representative area in the Drosophila melanogaster genome encoding miR-184 is shown. Nucleotide positions encoding thymine (T, red) are indicated relative to the 5' end of each small RNA species. Reads representing 99% of all 5' isoforms are shown for miR-184-3p and -5p and the respective number of reads are indicated in parts per million (ppm). (B) Small RNA sequencing libraries generated from total RNA of Drosophila S2 cells before and after $s^4U$ metabolic labeling for 24 h were mapped to annotated miRNAs and any given mutation rate was determined for abundantly expressed miRNAs (>100 ppm). Tukey boxplots show mutations per miRNA in percent. Outliers are not shown. Median observed frequency for each individual mutation are indicated. P-Value, as determined by Mann-Whitney test is indicated.
Figure 19:
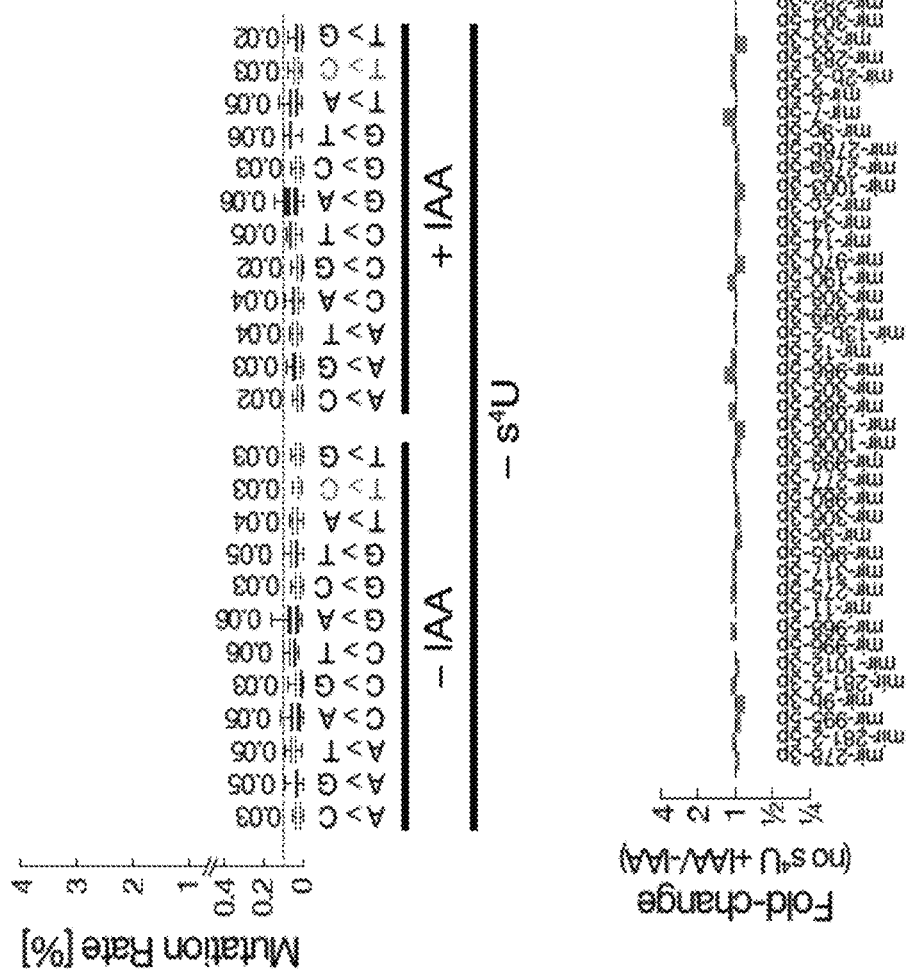
FIG. 19. Iodoacetamide treatment does not affect the quality of small RNA libraries. Small RNA sequencing libraries generated from total RNA of Drosophila S2 cells before and after treatment with iodoacetamide were mapped to annotated miRNAs and abundantly expressed miRNAs (>100 ppm) were analyzed. (A) Any given mutation rate was determined for each miRNA from small RNA libraries of iodoacetamide-treated or untreated total RNA. Tukey box-plots show mutations per miRNA in percent. Outliers are not shown. Median observed frequency for each individual mutation are indicated. (B) Abundance of miRNAs in small RNA libraries prepared from iodoacetamide-treated or untreated total RNA. Pearson correlation coefficient and associated p-value is indicated. (C) Fold-change in expression for individual miRNAs in small RNA libraries prepared from iodoacetamide-treated or untreated total RNA.

To test the ability of this method to uncover metabolically labeled small RNAs, we incubated Drosophila S2 cells with $s^4U$ for 24 h under conditions that do not interfere with cell viability (i.e. 500 µM), followed by total RNA extraction and small RNA sequencing. Metabolic labeling was confirmed by HPLC analysis of total RNA (FIG. 18), revealing a labeling efficiency of 2.3%, corresponding to $s^4U$ incorporation in one out of 43 uridines. Upon generating libraries from size-selected total RNA of Drosophila S2 cells after $s^4U$ metabolic labeling for 24 hours, we observed a strong accumulation of T>C conversions when compared to libraries prepared from unlabeled cells, as exemplified for the miR-184 locus, which gives rise to an abundantly expressed microRNA, miR-184-3p, and its less abundant miR*, miR-184-5p (FIG. 12A). In order to confirm this observation at the genomic scale, we aligned reads to annotated microRNA loci in the Drosophila genome and inspected the frequency of any given mutation normalized to overall T-content per miRNA (FIG. 12B). In the absence of $s^4U$ metabolic labeling, we observed a median mutation rate of less than 0.1% for any given mutation, a rate that is consistent with Illumina-reported sequencing error rates. (Note, that iodoacetamide treatment of unlabeled total RNA had no detectable impact on small RNA abundance and mutation rate, as determined by high-throughput sequencing. See FIG. 19). After 24 h of $s^4U$ metabolic labeling, we observed a statistically significant ($p<10^{-4}$, Mann-Whitney test), 74-fold increase in T>C mutation rates, while all other mutations remained below expected sequencing error rates (FIG. 12B). More specifically, we measured a median $s^4U$-incorporation of 2.22% after 24 h labeling, corresponding to one $s^4U$ incorporation in every 45 uridines, and consistent with incorporation rates determined by HPLC measurements of total RNA (FIG. 18). Metabolic labeling under unperturbed conditions therefore caused the vast majority (>95%) of small RNAs to exhibit at most one $s^4U$ incorporation event (FIG. 20), which is insufficient for quantitative recovery even through improved biotinylation strategies (Duffy et al., 2015, supra), but can readily be identified by chemical $s^4U$ derivatization (FIG. 12).

Figure 21:
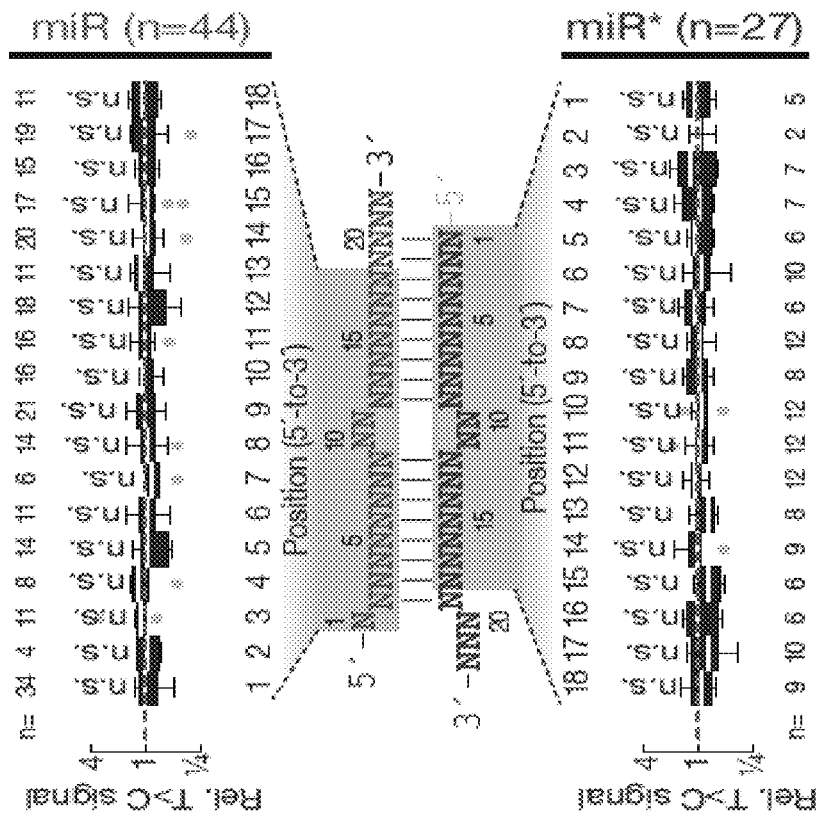
FIG. 21. $s^4U$-metabolic labeling does not impact microRNA biogenesis or loading. Over- or underrepresentation of T>C conversions at individual positions of a given small RNA that is derived from the 5p- or 3p arm of a microRNA precursor (left), or that constitutes a miR or miR* strand, as defined by selective Argonaute-loading (right). Results are derived from 71 abundantly expressed (>100 ppm) microRNAs (corresponding to 35 5p- and 36 3p-miRNAs, or 44 miR and 27 miR*). Statistically significant differences in relative representation were compared to the total population for the indicated position by Mann-Whitney test. n.s., p>0.05; n.d., not determined due to limited data points.
Figure 21:
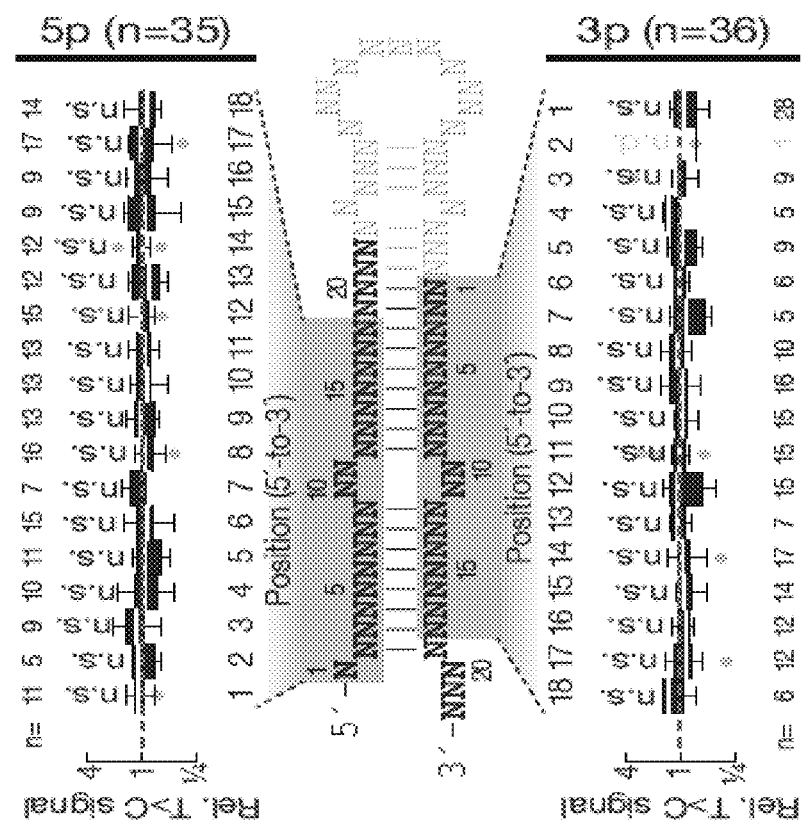

The ability of the inventive method to recover $s^4U$ incorporations at single nucleotide resolution enabled us to systematically dissect the impact of $s^4U$ metabolic labeling on microRNA processing and loading. To this end, we determined the over- or underrepresentation of T>C conversions at individual positions of a given small RNA that is derived from the 5p- or 3p arm of a microRNA precursor, or that constitutes a miR or miR* strand, as defined by selective Argonaute-loading. When consulting the 71 abundantly expressed (>100 ppm) microRNAs (corresponding to 35 5p- and 36 3p-miRNAs, or 44 miR and 27 miR*) we did not observe a significant systematic alteration in relative T>C mutation rates at any given position (FIG. 21). We concluded that $s^4U$-metabolic labeling does not impact microRNA biogenesis or loading.

Taken together, $s^4U$ metabolic RNA labeling in cultured Drosophila S2 cells, followed by SLAM-seq quantitatively recovers $s^4U$ incorporation events in small RNAs at single nucleotide resolution and reveals no significant position-dependent impact of $s^4U$ labeling on microRNA biogenesis and loading.

Example 8: Intracellular Kinetics of microRNA Biogenesis

Figure 13:
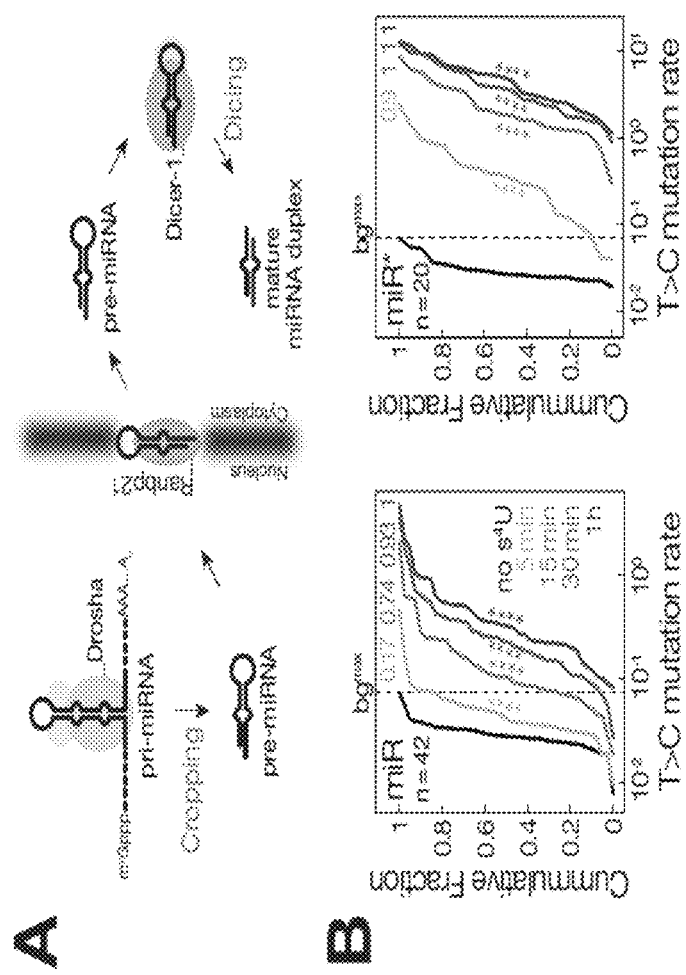
FIG. 13. Intracellular kinetics of microRNA biogenesis. (A) MicroRNAs are derived from hairpin-containing RNA polymerase II transcripts (primary microRNAs, pri-miRNAs) through sequential processing by the RNase III enzymes Drosha in the nucleus and Dicer in the cytoplasm resulting in a ~22 nt microRNA duplex. The hairpin-processing intermediate (precursor-microRNA, pre-miRNA) is exported from the nucleus to the cytoplasm by Ranbp21 in a RanGTP-dependent manner. (B) Cumulative distribution plots show the median T>C mutation rates for 42 abundantly expressed miRNAs (left) or 20 miR*s (right) in small RNA libraries generated from total RNA of Drosophila ago2$^{ko}$ S2 cells treated with $s^4U$ for the indicated time. P-Values were determined by Kolmogorov-Smirnov test (****=$p<10^{-4}$). $Bg^{max}$ indicates the maximum background error rate. (C) Average abundance of the indicated miRNAs (left) or miR*s (right) are shown at steady state or T>C conversion containing reads at the indicated timepoints after metabolic labeling by $s^4U$. Number of reads normalized to total small RNAs are shown in parts per million (ppm). Excess of mutation rates (Mu) above background maximum ($bg^{max}$) is indicated. (D) Mirtron hairpins are generated through splicing of protein coding transcripts. After intron lariat debranching mirtron hairpins are subjected to post-transcriptional uriylation in the cytoplasm, which modulates the 2 nt-3' overhang of pre-mirtrons, preventing miRNA biogenesis by Dicer. (E) T>C mutation rates (top) or small RNA-normalized T>C reads in parts per million (ppm) for canonical miRNAs (grey) or mirtrons (red) at the indicated timepoint of a $s^4U$-labeling experiment. Median and interquartile range are indicated. P-Value (Mann-Whitney test) is indicated (*, $p<0.05$; , $p<0.01$; *, $p<0.001$). N.d., not detected.
Figure 13:
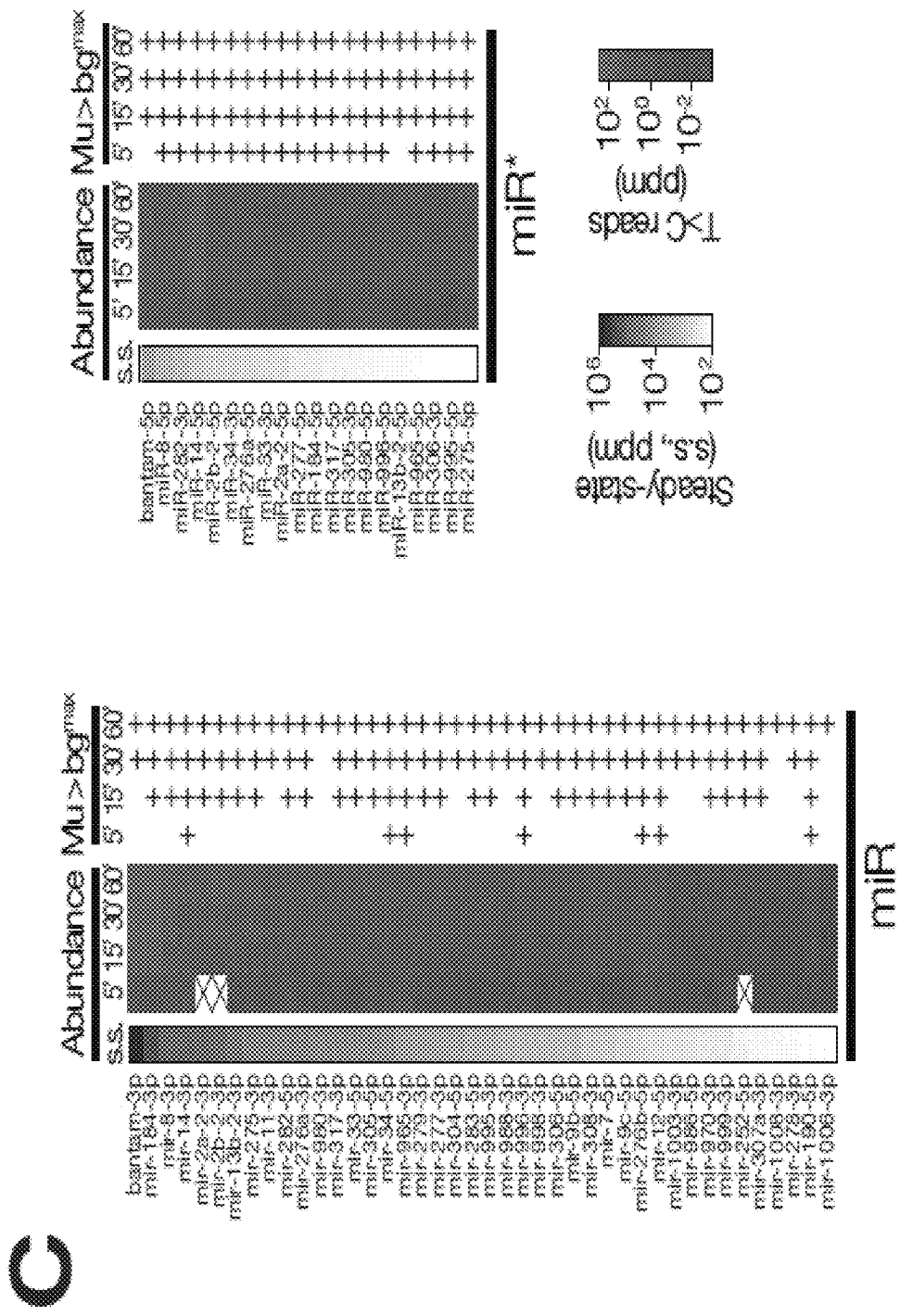
Figure 13:
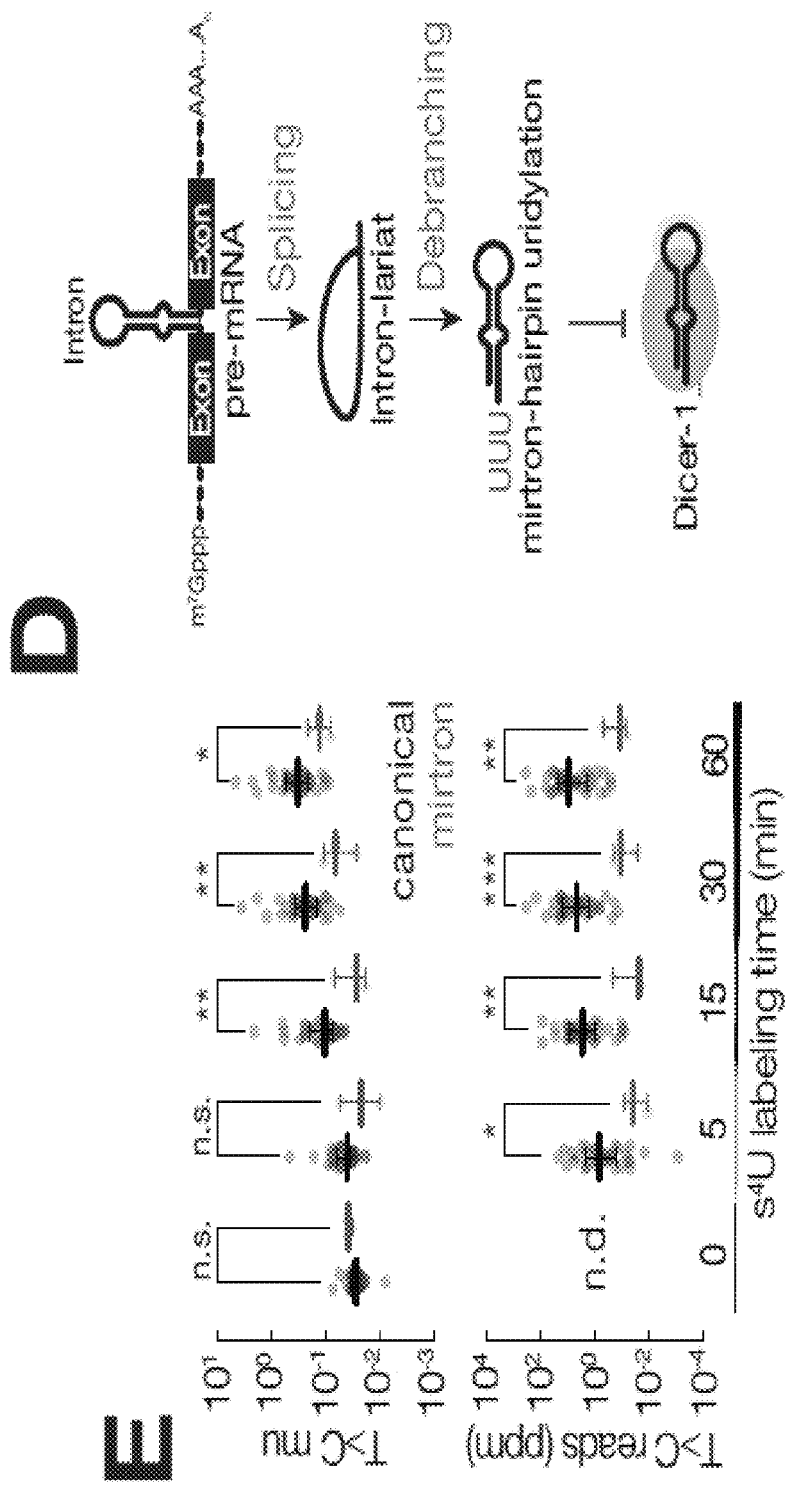

MicroRNAs are derived from hairpin-containing RNA polymerase II transcript that are sequentially processed by Drosha in the nucleus and Dicer in the cytoplasm, giving rise to mature miRNA duplexes (FIG. 13). To investigate the intracellular kinetics of miRNA biogenesis we determined the increase in T>C mutation rates of abundantly expressed miRNAs (>100 ppm at steady-state) in small RNA libraries prepared from size selected total RNA of Drosophila S2 cells 5 min, 15 min, 30 min and 60 min after metabolic labeling with $s^4U$ and compared them to error rates detected in the absence of $s^4U$ labeling (FIG. 13B). Already after a labeling time as short as 5 min, we detected a significant elevation in T>C conversion rates, with 17% of all miRs and 90% of all miR*s exhibiting error rates above the maximum background level. This fraction increases over time with 74%, 93% and 100% miRs after 15 min, 30 min and 1 h, respectively. Based on conservative measures, more than 50% of all miRNAs (22 out of 42) were detectably produced (i.e. exceeding the maximum background T>C conversion rates in either a miR or its respective miR* partner) in a short period of time, i.e. 5 min, revealing a remarkable efficiency in cellular organization of miRNA processing.

We also determined the number of T>C conversion-containing reads as a proxy for the number of miRNA molecules produced over time (FIG. 13C). While in average, miRNAs with high steady state abundance also exhibit a high production rate (such as miR-184, or miR-14), others exhibit low steady-state abundance despite high-biogenesis rates (such as miR-276b or miR-190), or vice versa (i.e. miR-980 or miR-11), indicating that the rate at which miRNAs are produced is not the sole determinant for their intracellular abundance.

While our global analysis revealed an unexpectedly high efficiency in overall miRNA biogenesis, selected small RNAs were produced at significantly lower rates. Examples for such ineffectively produced miRNAs were mirtrons (i.e. miR-1003, miR1006, or miR-1008; FIG. 13C), a class of microRNAs that are produced by splicing instead of Drosha-directed processing. Mirtron biogenesis may be selectively dampened, because splicing-derived precursor hairpins are specifically targeted for uridylation by the terminal nucleotidyltransferase Tailor, which recognizes the 3' terminal splice acceptor site, thereby preventing efficient Dicer-mediated processing and triggering dmDis3l2-directed exonucleolytic decay (FIG. 13D). Our data provide experimental evidence for the selective suppression of mirtron biogenesis, because mirtrons exhibit a significantly reduced T>C mutation rates and T>C conversion containing reads accumulated less rapidly over time, when compared to canonical miRNAs (FIG. 13D). The hypothesis that uridylation of pre-miRNA hairpins underlies the inhibition of mirtron biogenesis, we also detected a significant correlation between pre-miRNA tailing and T>C conversion rates (FIG. 22).

In summary, the new method uncovers a remarkable efficiency in the intracellular rates of miRNA production and recapitulates the selective inhibitory effect of precursor-hairpin uridylation on miRNA biogenesis.

Example 9: Monitoring Small RNA Loading into Ribonucleoprotein Complexes

MicroRNA biogenesis produces miRNA duplexes. But only one of the two strands of a miRNA duplex (the miR strand) is preferentially loaded onto Ago1 and selectively stabilized, whereas the other strand (the miR* strand) is expelled and degraded in the process of miRNA loading (FIG. 14A). To test if the inventive method recapitulates the process of miRNA duplex production and miRNA loading in living cells, we analyzed the relative accumulation of T>C conversion containing reads for 20 miRNAs, for which we detected sufficiently high levels of both miR and its partner miR* (FIG. 14B). We did not observe a significant difference in abundance between miR and miR* pairs at early timepoints after s$^4$U metabolic labeling (i.e. 5 min, 15 min and 30 min; Mann Whitney test p>0.05), confirming that miRNAs initially accumulate as duplexes in a process that is kinetically uncoupled from loading. Only after one hour, we detected a significantly higher accumulation of miR over miR* strands (Mann Whitney test p<0.05, FIG. 14B), indicating that—in average—loading of miRNAs into Ago1 occurs at much slower rates compared to miRNA biogenesis.

More detailed analysis uncovered a biphasic process underlying miRNA accumulation: The first phase was identical between miR and miR* ($k_{miR}$=0.35±0.03 and $k_{miR*}$=0.32±0.03), hence reflected the accumulation of miRNAs as a duplex. Notably, a second, slower phase was offset from the biogenesis phase for both miR and miR*. A severe drop in accumulation rates of miR*s ($k_{miR*}$=0.32±0.03) indicated that the vast majority (i.e. ~81%) of miR* strands undergo rapid degradation as a consequence of miRNA loading. In contrast, miR strands exhibited a much faster second accumulation rate ($k_{miR}$=0.26±0.03) compared to miR* strands ($k_{miR*}$=0.32±0.03), recapitulating the selective stabilization of miR strands, presumably due to miRISC formation. But when compared to the initial biogenesis rate ($k_{miR}$=0.35±0.03), also miRs exhibited a drop in second phase kinetics ($k_{miR}$=0.26±0.03), indicating that only ~74% of miR-strands are effectively loaded, while around a quarter of miRNAs are presumably degraded as a duplex. This is consistent with empty Argonaute-availability represents a key limiting factor for the accumulation of miRNAs, and their overexpression globally increases intracellular miRNA abundance.

Further investigation of individual miR:miR* pairs revealed varying loading efficiencies among miRNA duplexes: While strand separation—hence loading—was detectable within minutes in the case of miR-184, bantam exhibited slightly delayed loading kinetics with strand separation occurring not before ~30 min; and miR-282 ranked among the least efficiently loaded miRNAs (FIG. 14D). Notably, the different loading kinetics followed thermodynamic rules for Ago1 loading, where mismatches in the seed or 3' supporting region of miRNA duplexes promoted the efficient formation of miRISC.

In summary, the new method revealed detailed insights into miRNA biogenesis and loading kinetics.

Example 10: IsomiR Production

Figure 15:
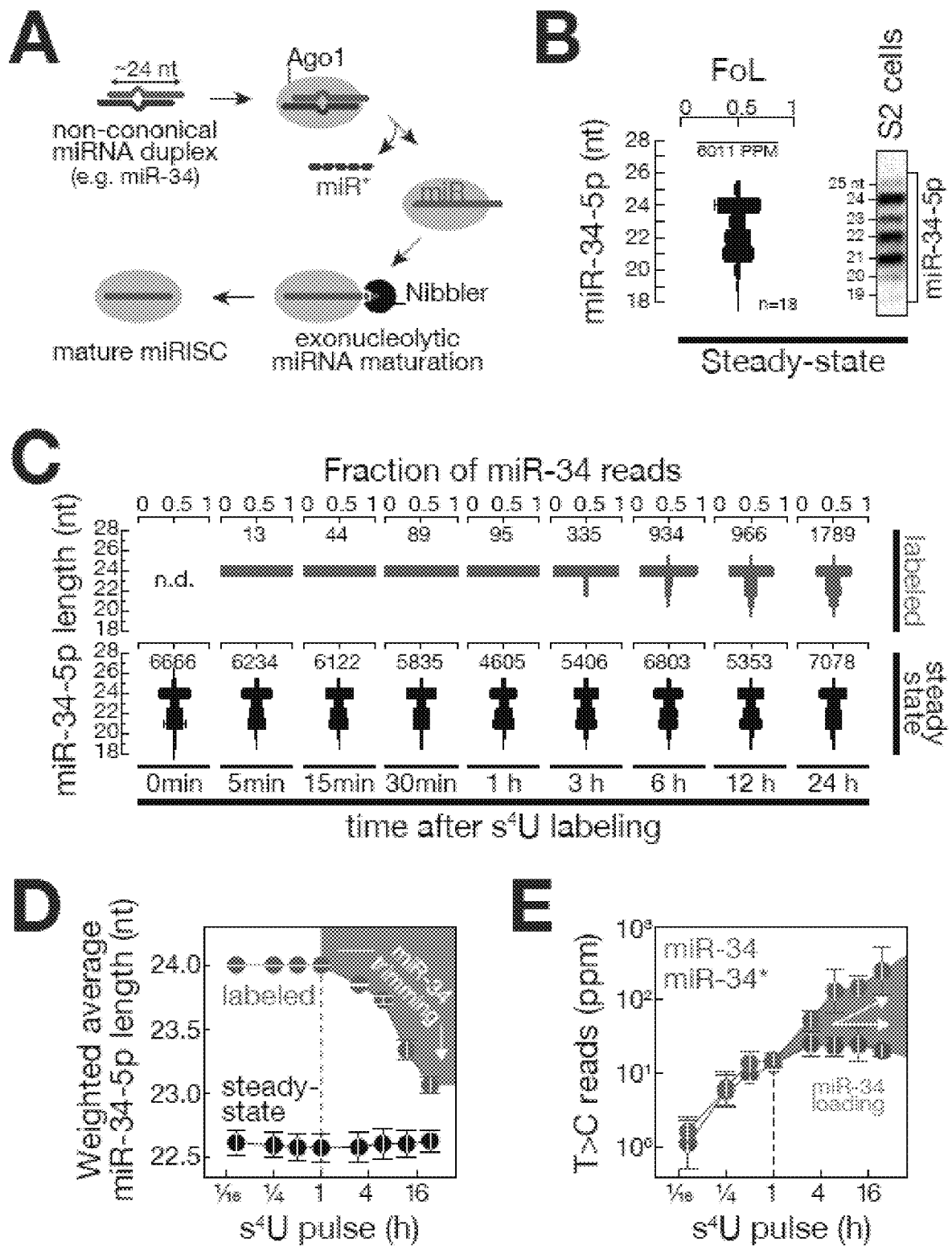
FIG. 15. Intracellular kinetics of exonucleolytic miRNA trimming. (A) Model for exonucleolytic miRNA maturation in Drosophila. A set of microRNAs (e.g. miR-34) are produced by Dicer as longer, ~24 nt miRNA duplexes that, upon loading into Ago1 and removal of the miR* strand, undergo exonucleolytic maturation mediated by the 3"-to-5' exoribonuclease Nibbler to form a mature, gene-regulatory, miRNA induced silencing complex. (B) Steady state length distribution of miR-34-5p in Drosophila ago2$^{ko}$ S2 cells as determined by high-throughput sequencing of small RNAs (left, bars represent mean±standard deviation of 18 measurements; the average cloning count is indicated in parts per million, ppm) or Northern-hybridization experiments (right). (C) Length distribution of miR-34-5p in libraries prepared from Drosophila ago2$^{ko}$ S2 cells subjected to s$^4$U metabolic labeling for the indicated time. Length distribution of T>C conversion containing reads (labeled, red, top) and all reads (steady-state, black, bottom) are shown. The underlying number of reads are indicated. Data show mean±standard deviation of two independent replicates. (D) Weighted average length of miR-34-5p in libraries prepared from Drosophila ago2$^{ko}$ S2 cells subjected to s$^4$U metabolic labeling for the indicated time. Data represents mean±standard deviation of T>C conversion-containing reads (labeled, red) and all reads (steady-state, black). Decrease in weighted average length of T>C conversion-containing reads indicates exonucleolytic trimming (highlighted by grey area). (E) Loading of miR-34-5p as determined by the relative abundance of T>C conversion containing reads in miR-34-5p (miR-strand, red) and miR-34-3p (miR* strand, blue) after s$^4$U metabolic labeling of Drosophila S2 cells. Mean±standard deviation of two independent experiments are shown. Loading is represented by the separation of miR from miR* and highlighted by grey area.

Accumulating evidence suggest that a variety of intracellular processes diversify the sequence and function of microRNAs, but the underlying mechanisms are poorly understood and difficult to dissect from steady-state small RNA sequencing libraries. One well-established example for isomiR production is the exonucleolytic maturation of miRNAs in flies. While the majority of miRNAs in Drosophila are produced as ~22 nt small RNAs, selected miRNAs are generated as longer, ~24 mers, which require further exonucleolytic maturation, mediated by the 3"-to-5' exoribonuclease Nibbler to form gene regulatory miRISC. In standard small RNA sequencing libraries and high-resolution Northern hybridization experiments, miR-34-5p exhibits a diverse length profile ranging from abundantly expressed 24-21 mer isoforms originating from 3' end truncations of the identical 5' isoform (FIG. 15B). To test the ability of the inventive method to disentangle the intracellular order of events that give rise to multiple miR-34-5p isoforms we analyzed small RNA libraries prepared from total RNA of S2 cells after subjecting them to s$^4$U-metabolic labeling timecourse. In contrast to steady state small RNAs, which displayed a highly similar length profile across the entire time course, T>C conversion containing miR-34-5p reads initially accumulated entirely as a 24 mer isoform, consistent with previous in vitro processing experiment employing recombinant Dcr-1 or fly lysate and synthetic pre-miR-34 (FIG. 15C, bottom). Only from 3 h onwards, we detected the emergence of shorter, T>C conversion containing miR-34-5p 3' isoforms (FIG. 15C top). From this timepoint on, the weighted average length of miR-34-5p over time decreased continuously, slowly approaching the average length profile of miR-34-5p observed at steady-state (FIG. 15D). We concluded that the inventive method uncovers the emergence of isomiRs, as exemplified by Nibbler-directed 3"-to-5' exonucleolytic trimming.

Exonucleolytic maturation of miRNAs requires their loading into Ago1 and biochemical evidence suggested that trimming only occurs after miR* strand removal, presumably because Nibbler proposed functions as a single-strand-specific 3"-to-5' exoribonuclease. Because our method enabled us to simultaneously measure miRNA loading and isomiR production, we tested this hypothesis by comparing miR-34-5p trimming signal (FIG. 15D) and miR34 duplex loading kinetics (FIG. 15E). We observed that trimming in deed occurred after miR-34 loading and miR* strand removal, as determined by the offset of miR-34-5p and -3p accumulation in our libraries starting after 1 h of metabolic labeling (FIG. 15E). In conclusion, the inventive method uncovers the intracellular order of miRNA isoform production, hence provides a powerful tool to shed light onto the processes that diversify the sequence and function of miRNAs in living cells.

Example 11: MicroRNA Stability

Figure 14:
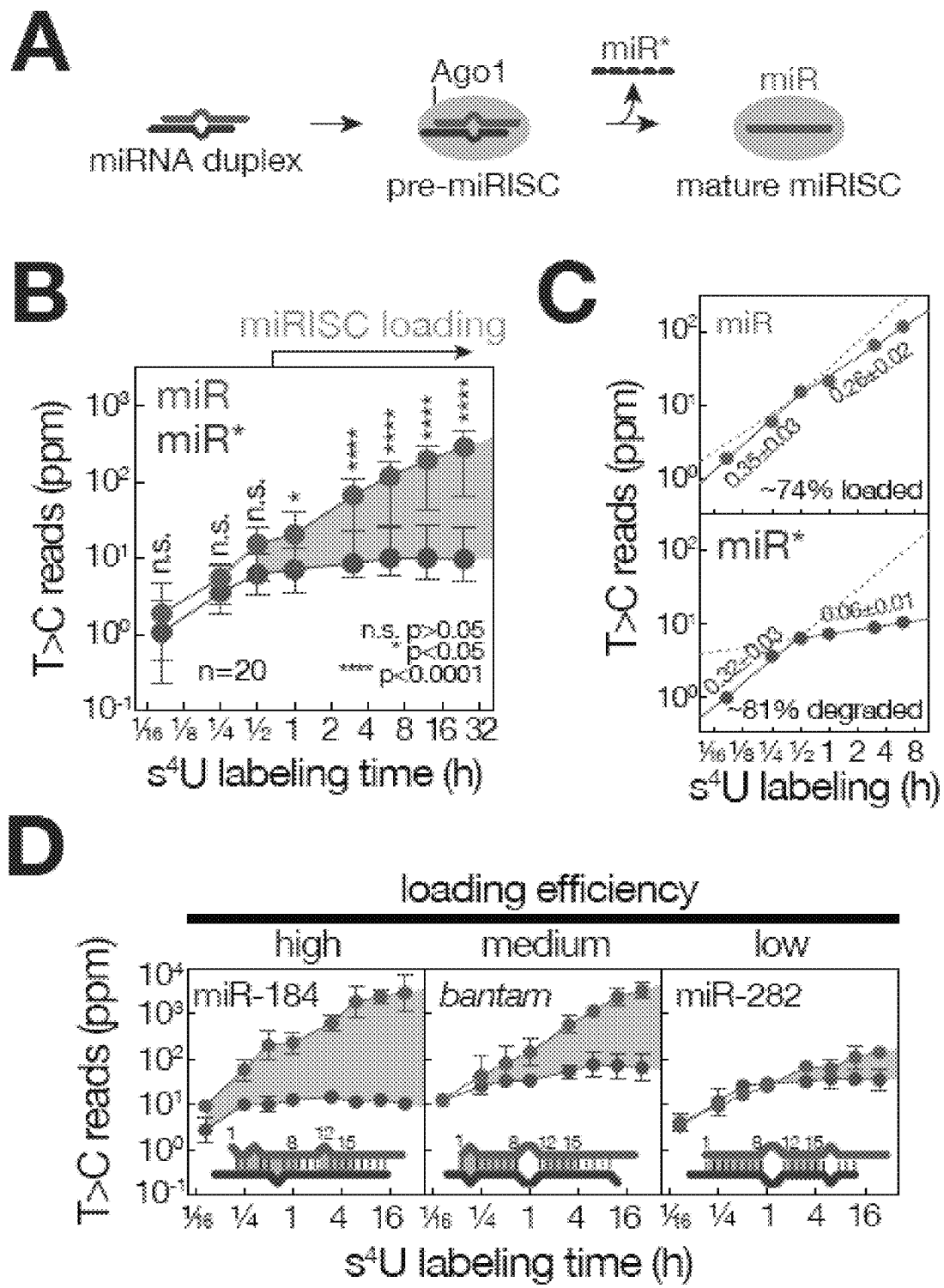
FIG. 14. Intracellular kinetics of microRNA loading. (A) Upon production, the microRNA duplex is loaded onto the Argonaute protein Ago1. In this process one of the two strands—the miR strand—is selectively retained in Ago1, whereas the other one—the miR* strand—is expelled and degraded. A single stranded miRNA bound to Ago1 forms the mature miRNA-induced silencing complex (miRISC). (B) Median accumulation of T>C conversion containing reads (in ppm) of 20 abundantly expressed miR and miR* pairs in the course of a $s^4U$ metabolic labeling experiment in ago2$^{ko}$ S2 cells. Median and interquartile range for miR (red) and miR* (blue) are shown. Values are derived from two independent measurements. P-value indicates significant separation of miR and miR* as determined by Mann Whitney test (*, $p<0.05$; ****, $p<0.0001$). (C) Zoom-in for the time course shown in (B) for miR (red, top) and miR* (blue, bottom).
Figure 16:
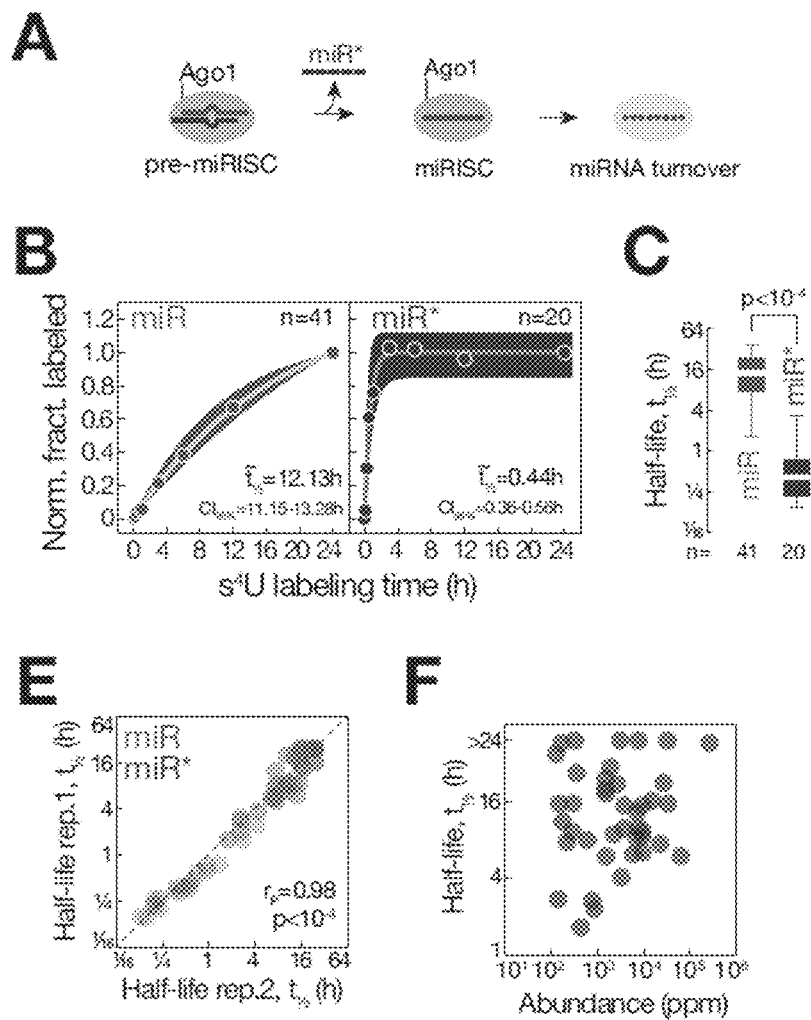
FIG. 16. Differential stability of miRNAs. (A) Upon loading of a microRNA duplex onto Ago1, forming pre-miRISC, the miR* strand (blue) is degraded, resulting in a mature miRNA-induced silencing complex (miRISC). The precise stability of miRNAs in miRISCs has remained obscure. (B) Increase in per-T-position mutation rate for 41 abundantly expressed miRNAs (red, left) and 20 miR*s (blue, right) across an s$^4$U-metabolic labeling time course in Drosophila ago2$^{ko}$ S2 cells. For each small RNA, the median mutation rate across all T-positions was determined and normalized to the 24-h timepoint. The median and interquartile range is shown. Values represent the mean of two independent replicates. The median half-life ($t_{1/2}$) and the 95% confidence interval was determined by single-exponential curve fitting. (C) Tukey box plot representing the half-life of 41 miRs (red) and 20 miR*s (blue). P-value was determined by Mann-Whitney test. (D) Steady-state abundance and average half-life for the indicated miR (red) and miR* (blue). Average half-life represents the mean of two independent replicates. The individual half-life measurements for two independent experiments (r1 and r2) are reported. Half-life data that exceeded the total time of the measurement are indicated as >24 h. (E) Comparison of half-life values determined in two independent biological replicates for 41 miR (red) and 20 miR* (blue) strands. Pearson's correlation coefficient ($r_p$) and associated p-value are shown. (F) MicroRNA stability differentially contributes to steady-state abundance of miRNAs. Half-life values for 40 miR are shown relative to their steady-state abundance. Data represents mean of two independent biological replicates.
Figure 16:
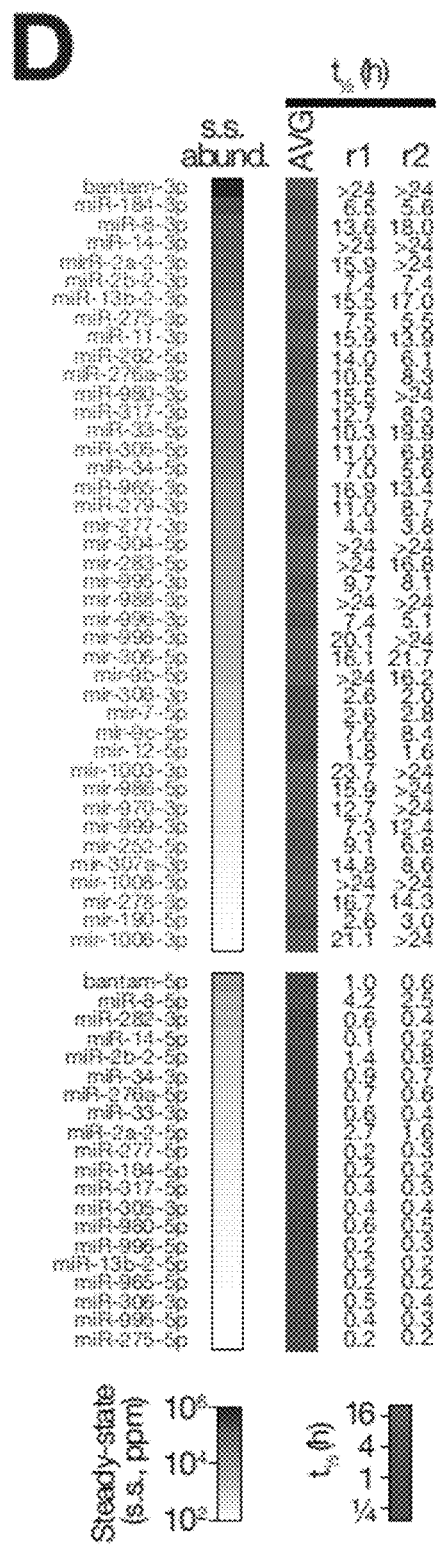

While different miRNAs assemble into otherwise indistinguishable protein complexes, accumulating evidences suggest that their stability can differ dramatically (FIG. 16). But currently available technologies only measure relative, but not absolute half-lifes for individual miRNAs, preventing detailed insights into miRNA stability. Furthermore, metabolic labeling under unperturbed conditions prompts the vast majority (>95%) of labeled small RNAs to exhibit at most one s$^4$U incorporation event (FIG. 20), which is insufficient for quantitative recovery even through improved biotinylation strategies (Duffy et al., 2015, supra), and introduces biases due to vastly different U-contents in miRNA different miRNA sequences. In contrast, the inventive method provides rapid access to absolute, and sequence content-normalized miRNA stabilities in the context of standard small RNA libraries (FIG. 16). By analyzing the T>C conversion rate normalized to miRNA-U-content in SLAM-seq small RNA libraries prepared from total RNA of Drosophila S2 cells subjected to s$^4$U metabolic labeling for up to 24 h, we determined a median half-life of 12.13 h for the 41 abundantly expressed miR strands (FIG. 16B), indicating that the average miRNA half-life is significantly longer compared to mRNAs, which exhibits an average half-life of ~4-6 hours. In contrast to miRs, miR*s exhibited a much shorter half-life of 0.44 h (FIG. 16B), consistent with their enhanced turnover as a consequence of miR-loading (FIG. 14). Overall, miR*s are significantly less stable compared to miRs (FIG. 16C). But even miRs exhibited intrinsically different stabilities that differed by more than one order of magnitude, as exemplified by the unstable miR-12-5p ($t_{1/2}$=1.7 h) and the stable bantam-5p ($t_{1/2}$>24 h). Importantly, the inventive method provides robust insights into individual small RNA half-lifes, providing highly reproducible results across a wide variety of small RNA stabilities (FIG. 16E).

MicroRNA stability is a major contributing factor to the establishment of small RNA profiles in S2 cells, as exemplified by the two miRNAs that accumulated to highest levels at steady-state: While bantam exhibited relatively slow biogenesis (FIG. 13) and medium loading rates (FIG. 14), it accumulated to highest steady-state levels because of an unusually high stability ($t_{1/2}$>24 h). In contrast, the second most abundant miRNA, miR-184-3p, was 3-times less stable compared to bantam-5p ($t_{1/2}$=6 h), but still accumulated to high levels because of its extraordinarily high biogenesis and loading kinetics (FIGS. 13 and 14). The metabolic sequencing of small RNAs by SLAM-seq therefore uncovers the relative contribution of miRNA biogenesis, loading and turnover to the establishment of steady-state small RNA profiles, the major determinant for miRNA-mediated gene regulation.

Example 12: Argonaute Protein Identity Defines Small RNA Stability

Figure 17:
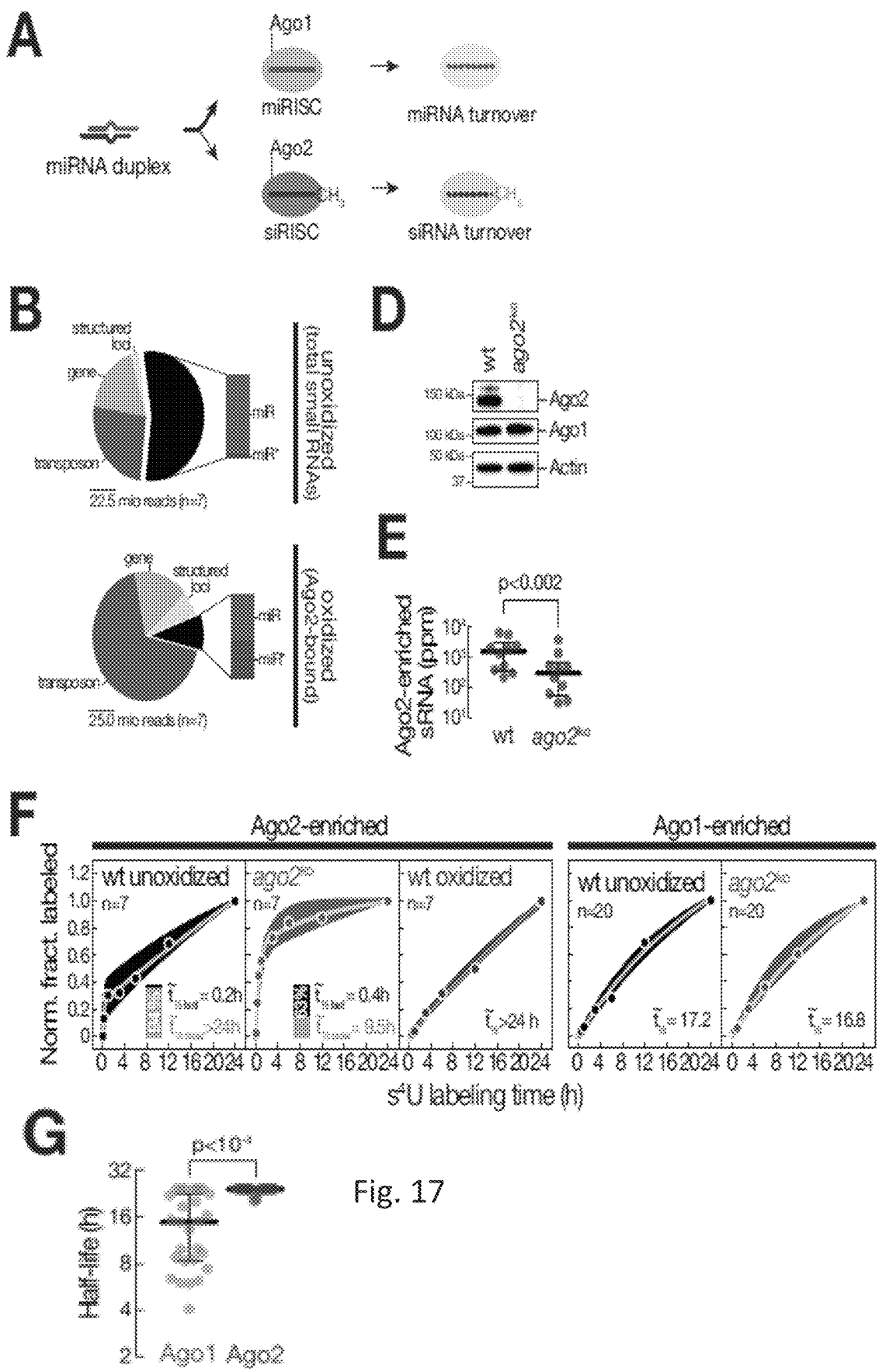
FIG. 17. Argonaute protein identity determines small RNA stability. (A) In Drosophila, miRNAs preferentially load onto Ago1 to form miRISC. In parallel, a subset of miR*s load into Ago2 to form siRISC. siRISC formation is accompanied by the specific methylation of Ago2-bound small RNAs at the 2' position of the 3' terminal ribose. If Argonaute protein identity differentially affects small RNA stability is unknown. (B) Pie charts represent the relative abundance of different endo-siRNA classes and miRNAs in small RNA libraries from wild-type Drosophila S2 cells. Results from a standard cloning protocol (unoxidized, upper diagram) and from a cloning strategy that enriches for small RNAs with modified 3' termini (oxidized, lower diagram) are shown. The fraction of miRs and miR*s is indicated for both libraries. The average distribution of 7 datasets is shown. The average library depth is indicated. (C) Heat maps show the relative abundance of miRs (red), and miR*s (blue) in the indicated libraries (in grayscale). The ratio of relative representations in the libraries indicates preferential association of small RNAs with either AGO1 (green) or AGO2 (red). (D) Western blot analysis of wild-type (wt) S2 cells, or S2 cells depleted of Ago2 by CRISPR/Cas9 genome engineering)(ago2$^{ko}$). Actin represents a loading control. (E) Relative abundance of Ago2-enriched miR and miR* in wild-type (wt) and ago2$^{ko}$ Drosophila S2 cells. Median and interquartile range is indicated. P-value was determined by Wilcoxon matched-pairs signed rank test. (F) Decay kinetics of Ago2- (left) and Ago1-enriched small RNAs (right) in standard libraries prepared from an s$^4$U metabolic labeling timecourse in wild-type (wt, black) or ago2$^{ko}$ S2 cells (red) or from wild-type S2 cells employing a cloning strategy that enriches for small RNAs with modified 3' termini (wt oxidized, blue). Median and interquartile range of two-phase or one-phase exponential fit (as specified in main text) are shown. The half-life (t½) as determined by curve-fitting is indicated. In case of two-phase kinetics, the relative contribution of fast and slow kinetics is shown. (G) Half-life of the 30 most abundant miRNAs in ago2ko S2 cells (red, Ago1) or the most abundant miRs and miR*s in small RNA libraries employing a cloning strategy that enriches for small RNAs with modified 3' termini (blue, Ago2). The median and interquartile range is indicated. P-value was determined by Mann-Whitney test.

The genomes of both mammals and insects, encode several proteins of the Argonaute protein family, some of which selectively load small RNAs to regulate distinct subsets of transcripts by varying mechanisms. While miRNA duplexes are intrinsically asymmetric, i.e. the miR strand preferentially loads into Ago1, each miRNA precursor can potentially produce two mature small RNA strands that are differentially sorted into two distinct ubiquitously expressed Argonaute proteins in flies. In contrast to the majority of miRs, miR*s are often loaded as functional species into Ago2, the effector protein in the RNAi pathway, and undergo selective methylation at the 2' position of the 3' terminal ribose by the methyltransferase Hen1 in the final step of Ago2-RISC assembly (FIG. 17A). Depletion of Ago2 does not compromise cell viability, and enabled us to investigate the role of Ago proteins in the selective stabilization of small RNAs. Furthermore, it provided an experimental framework to understand if small RNA half-lifes are intrinsically determined by the identity of the Ago protein they associate with.

Figure 17C:
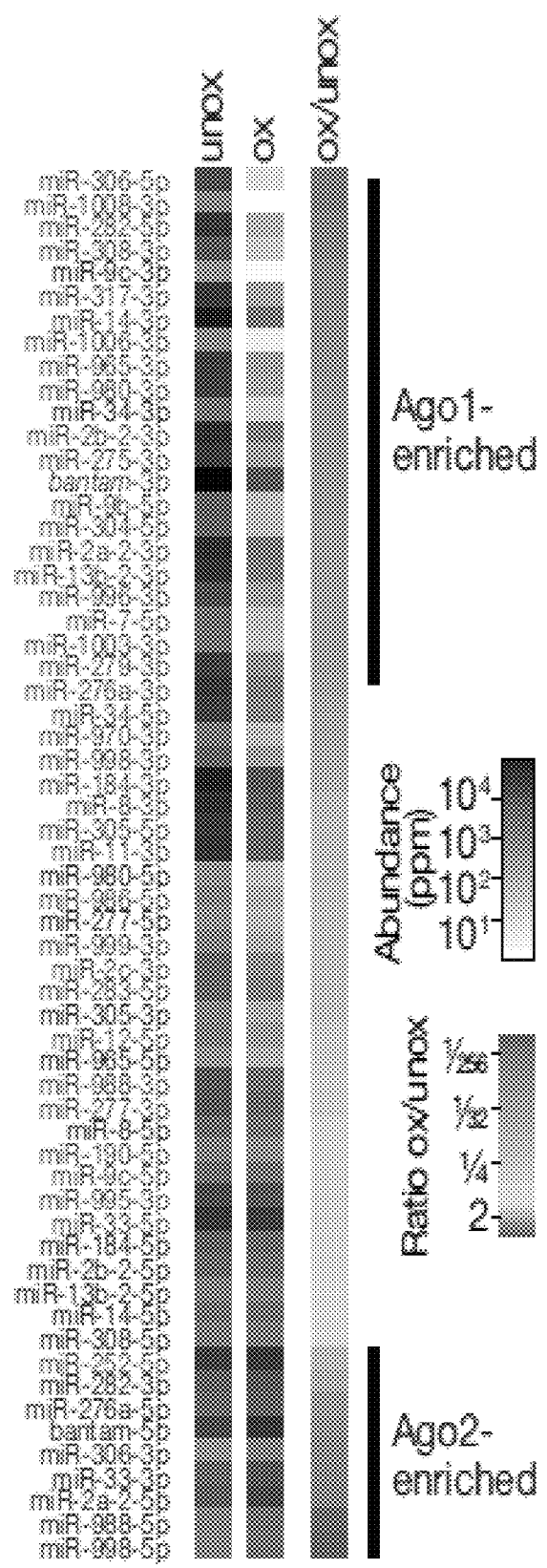

We first established the set of miRNAs that specifically assembled into Ago2 in wild-type *Drosophila* S2 cells by comparing small RNA libraries generated from total RNA by conventional small RNA cloning (predominantly reflecting Ago1-bound small RNAs) to libraries generated from total RNA but enriching for methylated (i.e. Ago2-bound) small RNAs by oxidation. While the majority of small RNAs in the conventional cloning approach consisted of miRNAs (particularly miR strands), oxidation selectively enriched for Ago2-bound endogenous small RNAs derived from transposons, genes (predominantly derived from overlapping mRNA transcripts) and loci giving rise to long fold-back transcripts (structured loci). As described previously, the subset of methylated (i.e. Ago2-bound) miRNAs was selectively enriched for miR*s. Comparison of unoxidized and oxidized small RNA libraries enabled us to classify miR and miR* strands according to their accumulation in Ago1 or Ago2 (FIG. 17C). By comparing the abundance of Ago2-enriched small RNAs in conventional small RNA libraries generated from wild-type S2 and S2 cells depleted of Ago2 by CRISPR/Cas9 genome engineering (FIG. 17D), we confirmed that Ago2-enriched small RNAs are significantly less abundant upon depletion of Ago2 (p<0.002, Wilcoxon matched-pairs signed rank test, FIG. 17E).

We next determined the stability of Ago2-enriched small RNAs by measuring small RNA stabilities in total small RNA libraries prepared from wild-type and Ago2-depleted) (ago2$^{ko}$ cells by s$^4$U metabolic-labeling followed by SLAM-seq. In wild-type cells, Ago2-enriched small RNAs followed a two-phase decay kinetic, where the majority (i.e. 94%) of the population exhibited high stability ($t_{1/2}$>24 h) and only a minority did undergo rapid decay, with a half-life similar to miR*s ($t_{1/2}$=0.2 h). We tested if the population associated with long half-life might represent the Ago2-bound fraction by determining the stability of the same small RNA species in methylated small RNA libraries. Indeed, Ago2-enriched small RNAs followed single-exponential decay kinetics with a half-life of >24 h (FIG. 17F). Conversely, in Ago2-depleted S2 cells, Ago2-enriched small RNAs again followed dual-phase decay kinetics, but now the majority (63%) of the population exhibited miR*-like stability ($t_{1/2}$=0.4 h), indicating that in the absence of Ago2, these small RNAs are predominantly decayed upon loading of their partner-strand into Ago1. In contrast, Ago1-enriched small RNAs had identical stabilities in the presence and absence of Ago2 (FIG. 17F). Our data therefore unravels population-specific stabilities of miRNAs that are determined by their loading into specific Ago-proteins. Finally, to dissect if small RNA half-lifes are intrinsically determined by the identity of the Ago protein they associate with we compared the stabilities of the 30 most abundant small RNAs in Ago1 and Ago2 (FIG. 17G). This analysis revealed that Ago2-bound small RNAs exhibited a significantly higher stability compared to Ago1-bound small RNAs ($p<10^{-4}$; Mann Whitney test), perhaps because methylation of Ago2-bound small RNAs contributes to the stabilization of small RNAs in Ago2 but not Ago1.

In summary, we provide an experimental framework for the dissection of the molecular mechanisms underlying the establishment and maintenance of small RNA profiles that impact gene expression states in health and disease.

Example 13: SLAM-Beg Defines Direct Gene-Regulatory Functions of the BRD4-MYC Axis Defining direct target genes of transcriptional regulators such as BRD4 and MYC is critical, both for understanding their basic cellular function and for therapy development. However, deciphering direct regulatory relationships remains challenging for various reasons. While genomic binding sites can be mapped e.g. by chromatin-immunoprecipitation and sequencing (ChIP-seq), mere binding of a factor does not predict regulatory functions on neighboring genes. An alternative approach involves differential expression profiling following experimental perturbation of a given regulator.

To further test whether SLAM-seq also captures more specific transcriptional responses evoked by perturbation of e.g. signaling pathways, we treated K562 cells with small-molecule inhibitors of their driving oncogene BCR/ABL, as well as MEK and AKT, which act as mediators in distinct signaling cascades downstream of BCR/ABL (FIG. 25D, FIGS. 30, A and B).

Cell Culture

Leukemia cell lines K562, MOLM-13 and MV4-11 were cultured in RPMI 1640 and 10% fetal calf serum (FCS). OCI/AML-3 cells were grown in MEM-alpha containing 10% FCS. HCT116 and Lenti-X lentiviral packaging cells (Clontech) were cultured in DMEM and 10% FCS. All growth media were supplemented with L-Glutamine (4 mM). For growth curves, cells were seeded at an initial density of $2 \cdot 10^6$ cells/ml in presence or absence of 100 µM IAA (Indole-3-acetic acid sodium salt, Sigma-Aldrich) and split every 24 h in a ratio of 1:2.6 to renew medium and IAA and to maintain cells subconfluent. Cell densities were measured every 24 h using a Guava EasyCyte flow cytometer (Merck Millipore).

Viability assays of cells treated with combinations of JQ1 and NVP-2 for 72 h were performed using the CellTiter-Glo Luminescent Cell Viability Assay (Promega). Relative luminescence signals (RLU) were recorded using an EnSpire Multimode Plate Reader (Perkin Elmer). Fractional responses to drug treatment were defined as $\alpha = 1 - (RLU_{treated}/RLU_{untreated})$ and synergism was calculated as excess over Bliss additivity (eob), where $eob = \alpha_{NVP-2, JQ1} - \alpha_{JQ1} - (\alpha_{NVP-2} \cdot 1 - \alpha_{JQ1})$.

Plasmids and Vectors Used in this Example

SpCas9 and sgRNAs were expressed from the plasmid pLCG (hU6-sgRNA-EFS-SpCas9-P2A-GFP). pLCG was cloned based on a publicly available Cas9 expression vector (lentiCRISPR v2, Addgene plasmid #52961) and includes an improved chiRNA context. For sgRNA sequences cloned into pLCG. As donors for homology directed repair of target loci, AID knock-in cassettes were generated by gene synthesis (Integrated DNA Technologies) and PCR-amplification of ca. 500 bp homology arms (HA) from genomic DNA of target cell lines. All constituents were assembled into a lentiviral plasmid backbone (Addgene plasmid #14748) additionally providing constitutive GFP expression for monitoring transfections, yielding the final vectors pLPG-AID-BRD4 (5'HA-Blast$^R$-P2A-V5-AID-spacer-3'HA-hPGK-eGFP) and pLPG-MYC-AID (5'HA-spacer-AID-P2A-Blast$^R$-3'HA-hPGK-eGFP). For acute protein depletion experiments, Oryza sativa Tir1 was introduced using the published lentiviral vector SOP (pRRL-SFFV-Tir1-3xMYC-tag-T2A-Puro). For competitive proliferation assays, Tir1 was introduced using the vector SO-blue (pRRL-SFFV-Tir1-3xMYC-tag-T2A-EBFP2). RNAi was performed using the vector LT3GEN delivering shRNAmir-inserts.

Genome Editing & Lentiviral Transduction

To derive AID knock-in cell lines, plasmids pLCG and pLPG were co-delivered by electroporation using a MaxCyte STX electroporator (K562) or by transfection using FuGENE HD Transfection Reagent (Promega, HCT116). After selection with blasticidin (10 µg/ml, Invitrogen) for successful knock-in, GFP⁻ single-cell clones were isolated using a BD FACSAria III cell sorter (BD Biosciences). Clones were characterized by PCR-genotyping on crude cell lysates. Knock-in was further confirmed by immunoblotting of tagged proteins and for K562, clones were characterized by flow cytometry to best match the immunophenotype of wildtype cells.

For acute protein depletion experiments, validated homozygous AID knock-in clones were transduced with the Tir1 expression vector SOP. Packaging of lentiviral particles was performed in Lenti-X cells by polyethylenimine transfection (PEI, $M_w$ 25000, Polysciences) of the viral plasmid and helper plasmids pCMVR8.74 (Addgene plasmid #22036) and pCMV-VSV-G (Addgene plasmid #8454) according to standard procedures. Target cells were infected at limiting dilutions and selected on puromycin (2 µg/ml, Sigma-Aldrich). All depletion experiments were performed with freshly transduced and selected cells to avoid potential silencing of transgenes.

Immunoblotting and Immunophenotyping

Chemiluminescent detection of primary antibodies was performed using HRP-conjugated secondary antibodies (Cell Signaling Technology, catalog numbers #7074, #7076 and #7077). Alternatively, fluorescence detection of rabbit and mouse primary antibodies was performed on an Odyssey CLx Imaging System (LI-COR Biosciences) using secondary antibodies IRDye 680RD Goat anti-Rabbit IgG and IRDye 800CW Goat anti-Mouse IgG (LI-COR Biosciences).

For immunophenotyping, cells were washed with FACS-buffer (5% FCS in PBS) and pre-incubated with an FCS-receptor blocking peptide (Human TruStain FcX, Biolegend, diluted 1:20 in FACS-buffer) for 10' at room temperature. Fluorophore-conjugated antibodies were added at a final dilution of 1:400 and cells were incubated for 20' at 4° C. Stained cells were washed twice and resuspended in FACS-buffer prior to analysis on a BD LSRFortessa flow cytometer (BD Biosciences).

Chromatin Fractionation

For chromatin fractionation, cells were washed in ice cold PBS and resuspended in chromatin extraction buffer (20 mM Tris-HCl, 100 mM NaCl, 5 mM MgCl$_2$, 10% glycerol, 0.2% IGEPAL CA-630, 20 mM β-glycerophosphate, 2 mM NaF, 2 mM Na$_3$VO$_4$, Protease Inhibitor Cocktail (EDTA-free, Roche), pH 7.5). The insoluble fraction was precipitated by centrifugation (16000 g, 5', 4° C.) and washed three times in chromatin extraction buffer in which it was subsequently resuspended. Total cell fraction and supernatant were sampled before and after the first precipitation respectively. All fractions were supplemented with SDS (sodium dodecyl sulfate, 0.1% (w/v)), digested with benzonase (Merck Millipore, 30', 4° C.) and re-dissolved by sonication in a Bioruptor sonication device (Diagenode).

SLAM-Seq

All SLAM-seq assays were performed at 60-70% confluency for adherent cells or 60% of the maximum cell density counted on a hemocytometer for suspension cells. 5-7 h prior to each assay, growth medium was aspirated and replaced. Unless stated otherwise, cells were pre-treated with indicated small molecule inhibitors or 100 µM IAA for 30 minutes to pre-establish full target inhibition or degradation. Newly synthesized RNA was labeled for indicated time spans (45' or 60') at a final concentration of 100 µM 4-thiouridine (s$^4$U, Carbosynth). Adherent cells were harvested by direct snap-freezing of plates on dry ice. Suspension cells were spun down and immediately snap-frozen. RNA extraction was performed using the RNeasy Plus Mini Kit (Qiagen). Total RNA was subjected to alkylation by iodoacetamide (Sigma, 10 mM) for 15' and RNA was re-purified by ethanol precipitation. 500 ng alkylated RNA were used as input for generating 3' mRNA sequencing libraries using a commercially available kit (QuantSeq 3' mRNA-Seq Library Prep Kit FWD for Illumina and PCR Add-on Kit for Illumina, Lexogen). Deep sequencing was performed using HiSeq1500 and HiSeq2500 platforms (Illumina).

Differential Gene Expression Analysis, PCA and GO-Term Enrichment

For gene-level analysis, raw reads mapped to different UTR annotations of the same gene were summed up by Entrez Gene ID. Pilot studies of K562 cells with kinase inhibitors were performed as single experiments. Analysis of differential gene expression was restricted to genes with 10 reads in at least one condition for 50 bp sequencing runs (flavopiridol and DMSO) or 20 reads in at least one condition for 100 bp sequencing runs (mk2206, trametinib, nilotinib, trametinib+mk2206 and DMSO). For estimating differential expression, a pseudo-count of 1 raw read was added to all genes.

All other SLAM-seq experiments were performed in triplicates and analyzed as follows. Differential gene expression calling was performed on raw read counts with 2 T>C conversions using DESeq2 (version 1.14.1) with default settings, and with size factors estimated on corresponding total mRNA reads for global normalization. Downstream analysis was restricted to genes passing all internal filters for FDR estimation by DESeq2. Principal component analysis was performed after variance stabilizing transformation on the 500 most variable genes across all conditions of a given experiment. GO-term enrichment analysis was performed on genes significantly and strongly downregulated (FDR≤0.1, $\log_2 FC \leq -1$) in SLAM-seq upon IAA-treatment in K562$^{MYC-AID}$+Tir1 by the PANTHER Overrepresentation Test (Fisher's Exact with FDR multiple test correction, pantherdb.org).

Estimation of mRNA Turnover

To obtain a rough estimate of mRNA turnover in unperturbed K562 cells, we assumed a steady-state equilibrium of mRNA biosynthesis and decay with first order kinetics approaching complete labeling after prolonged s$^4$U exposure. For any gene i, the fraction βi of converted reads (≥2 T>C conversions) within the total read counts after 60 minutes of s$^4$U labeling, could therefore be used to calculate the cellular mRNA half-life as:

$$t_{1/2,i} = -60 \cdot \frac{\ln(2)}{\ln(\beta_i)}$$

Chromatin Immunoprecipitation Followed by Deep Sequencing (ChIP-Seq)

For ChIP-Seq, $1 \cdot 10^8$ to $2 \cdot 10^8$ K562$^{AID-BRD4}$+Tir1 cells were treated for 1 h with 100 μM IAA or DMSO, cross-linked with 1% formaldehyde for 10' at room temperature and quenched with 500 mM glycine for 5', followed by 2 washes with ice-cold PBS. After isolation of nuclei, pellets were lysed in lysis buffer (10 mM Tris-HCl, 100 mM NaCl, 1 mM EDTA, 0.5 mM EGTA, 0.1% Na-Deoxycholate and 0.5% N-lauroylsarcosine, pH 8.0) containing protease inhibitors (Complete, Roche). Chromatin shearing was performed using a Bioruptor sonication device (Diagenode). Cell debris was pelleted by centrifugation at 4° C. for 10' at 16000 g. To allow direct comparison between DMSO- and IAA-treated ChIP-seq samples chromatin from a mouse AML cell line (RN2) was added as a spike-in control for internal normalization at a ratio of RN2:K562≈1:10. Triton X-100 was added (1% final concentration) and immunoprecipitation was performed by incubating the chromatin lysate with 5-10 μg of antibody overnight at 4° C. on a rotating wheel. Antibody-chromatin complexes were captured with magnetic sepharose beads (G&E Healthcare; blocked with 1 mg/ml BSA in TE for 2 h at room temperature) for 2 h at 4° C. on a rotating wheel. Beads were washed one time each with RIPA buffer (150 mM NaCl, 50 mM Tris-HCl, 0.1% SDS, 1% IGEPAL CA-630, 0.5% Na-deoxycholate, pH 8.0), Hi-Salt buffer (500 mM NaCl, 50 mM Tris-HCl, 0.1% SDS, 1% IGEPAL CA-630, pH 8.0), LiCl buffer (250 mM LiCl, 50 mM Tris-HCl, 1% IGEPAL CA-630, 0.5% Na-deoxycholate, pH 8.0) and twice with TE. Immune complexes were eluted in 1% SDS, 100 mM NaHCO$_3$. Samples were treated with RNase A (100 μg/ml) for 30' at 37° C., NaCl (200 mM) was added and cross-links were reversed for 6 h at 65° C., followed by 200 μg/ml Proteinase K digestion at 45° C. for 2 h. Genomic DNA was recovered by phenol-chloroform extraction and ethanol precipitation from both, the precipitated material as well as from the sheared chromatin input (1% of the material used for ChIP). Libraries for Illumina sequencing were prepared using the NEBNext Ultra II DNA Library Prep Kit for Illumina (New England Biolabs, #7645).

Analysis of Spike-In Controlled ChIP-Seq Data

For the analysis of spike-in controlled ChIP-seq samples a hybrid reference genome was prepared by merging human and mouse genomic sequences (GRCh38 and mm10). Reads were first aligned against this hybrid genome using bowtie2 v2.2.9 (—sensitive) and subsequently separated into human and mouse bins. Read coverage of each track was calculated using deeptools v2.5.0.1 and re-scaled using spike-in normalization factors. The resulting normalized coverage tracks were further subtracted by their respective input signal before calculating ratios between DMSO- and IAA-treated samples.

Re-Analysis of ChIP-Seq and Click-Seq Data and Super-Enhancer Calling

Previously published Click-seq data, H3K27ac ChIP-seq data and according input samples were re-aligned to GRCh38 with bowtie (version 1.1.2) following removal of adapter sequences using cutadapt. For K562 cells, super-enhancer proximal genes were used. For MV4-11 and MOLM-13, H3K27ac peaks were called using MACS2 (v2.1.0.20140616) with default parameters. Super-enhancer calling was performed using ROSE v0.1 with default parameters. Super-enhancers were assigned to genes based on the closest TSS within 100 kb. Subsequent comparisons were restricted to super-enhancer proximal transcripts with an assigned Entrez GeneID and detectable expression in SLAM-seq.

Predictive Modeling of Transcriptional Responses

TSS positions of all Refseq transcripts in GRCh38.p9 were downloaded from www.ensembl.org/biomart. The density of CAGE-seq reads within 300 bp from each TSS on the respective strand was extracted from published CAGE-seq data of K562 cells. The TSS with the highest mean signal of two replicates was retained for further analysis. 213 publicly available, pre-analyzed ChIP-seq tracks and 1 whole-genome bisulfite sequencing experiment were obtained from the ENCODE project (www.encodeproject.org/) or the Cistrome Data Browser (cistrome.org/db/). ChIP-seq signals within 500 and 2000 bp around each TSS were used as input for classification modeling.

For predictive modeling of JQ1 hypersensitivity, genes were classified as down-regulated based on responses of K562 cells to 200 nM JQ1 measured by SLAM-seq (FDR≤0.1, $\log_2$ FC≤−0.7). Unaffected genes (FDR>0.1, −0.1≤$\log_2$ FC≤0.1) were subsampled to give a matched control set of equal size and base-line mRNA expression by iterative resampling and comparison to the target distribution by a Kolmogorov-Smirnov test. Query and control genes were intersected with the TSS-ChIP-seq signal matrix and divided into training (75%) and test sets (25%). Scaled and centered ChIP signals were used to train five independent classifiers (elastic net GLM, gradient boosting machine, and SVMs with linear, polynomial and radial kernels) with ≥5-fold cross-validation during parameter tuning using the CARET package. The performance of all 4 final models was compared on the held-out test set.

For predictive modeling of MYC-dependent transcription, genes were classified as down-regulated (FDR≤0.1, $\log_2$ FC≤-1) or unaffected (FDR≤0.1, -0.2≤$\log_2$ FC≤0.2) based on responses in SLAM-seq upon IAA-treatment of K562$^{MYC-AID}$+Tir1 cells. Unaffected genes were further subsampled to give and equally sized and expression-matched control set as described for JQ1 response modeling. Given the large sample size, genes were divided into training (60%) and test sets (20%) as well as an additional validation set (20%) and processed as described for the modeling of JQ1 responses.

Analysis of a Direct MYC Target Signature in Cell Lines and Cancer Patient RNA-Seq Data For comparison of MYC expression to an empirical MYC response signature, FPKM-normalized gene expression data of 672 human cancer cell lines was obtained from Klijn et al. (Nat. Biotechnol. 33, 306-12 (2015)). Cell lines expressing MYCN or MYCL at higher levels than MYC were excluded and remaining samples were classified as MYC-high (top 20% MYC expression) or MYC low (bottom 20% MYC expression). Among all genes annotated in the cell line expression dataset by Entrez GeneID and significantly downregulated (FDR≤0.1) in K562$^{MYC-AID}$+Tir1 and HCT116 MYC-AID Tir1, the 100 genes with the strongest mean downregulation in both cell lines were defined as a common MYC response signature. To obtain a balanced estimate of the expression of all signature genes, FPKM values for each gene were scaled across all cell lines and scaled expression values of all signature genes were averaged for each cell line. Upper-quartile normalized gene expression data of 5583 cancer patients from 11 TCGA projects was downloaded from portal.gdc.cancer.gov and processed independently for each cancer type as described for the cell line dataset. Gene set enrichment analysis was performed using GSEA Desktop v3.0 beta.

Sample Preparation for Proteomics

K562$^{AID-BRD4}$+Tir1 cells were treated in three independent experiments with 100 μM IAA or DMSO for 60', washed three times with ice cold PBS, pellet by centrifugation and snap-frozen. Pellets were resuspended in lysis buffer (10M Urea, 50 mM HCl) and incubated for 10' at RT followed by adjustment of the pH with 1M Tris-buffer (Tris-HCl, $c_{final}$=100 mM, pH 8). Nucleic acids were digested with benzonase (Merck Millipore, 250U per pellet, 1 h, 37° C.), and iodoacetamide was added to for alkylation (15 mM, 30', room temperature) before quenching with DTT (4 mM, 30', 37° C.). For proteolysis, 200 μg protein per sample were diluted with 100 mM Tris-buffer to a urea concentration of 6M and digested with Lys-C (Wako) at an enzyme-to-protein ration of 1:50 (3 h, 37° C.). Samples were further diluted with 100 mM Tris-buffer to a final Urea concentration of 2M digested with Trypsin (Trypsin Gold, Promega) at an enzyme-to-protein ratio of 1:50 (37° C., overnight). pH was adjusted to <2 using 10% trifluoroacetic acid (TFA, Pierce) and desalted using C18 cartridges (Sep-Pak Vac (50 mg), Waters). Peptides were eluted with 70% acetonitrile (ACN, Chromasolv, gradient grade, Sigma-Aldrich) and 0.1% TFA, followed by freeze-drying. Isobaric labeling was performed using the TMTsixplex Isobaric Label Reagent Set (Thermo Fisher Scientific), samples were mixed in equimolar amounts and freeze-dried. After re-purification using a C18 cartridge, peptides were eluted with 70% ACN and 0.1% formic acid (FA, Suprapur, Merck) followed by freeze-drying.

Proteomics Sample Fractionation by Strong Cation Exchange Chromatography (SCX)

The dried sample was dissolved in SCX Buffer A (5 mM $NaH_2PO_4$, 15% ACN, pH 2.7). SCX was performed on 200 μg of peptide using an UltiMate 3000 Rapid Separation system (Thermo Fisher Scientific) at a flow rate of 35p1/min and a custom-made TOSOH TSKgel SP-2PW SCX column (5 μm particles, 12.5 nm pore size, 1 mm i.d.×250 mm). For the separation, a ternary gradient was used starting with 100% buffer A for 10', followed by a linear increase to 10% buffer B (5 mM $NaH_2PO_4$, 1M NaCl, 15% ACN, pH 2.7) and 50% buffer C (5 mM $Na_2HPO_4$, 15% ACN, pH 6) in 80', to 25% buffer B and 50% buffer C in 10', 50% buffer B and 50% buffer C in 10' and an isocratic elution for further 15'. The flow-through was collected as single fraction and along the gradient fractions were collected every minute over 140', pooled into 110 fractions and stored at −80° C.

LC-MS/MS for Peptide Quantification

LC-MS/MS was performed using a Thermo Fisher RSLC nano system (Thermo Fisher Scientific) coupled to a Q Exactive HF mass spectrometer (Thermo Fisher Scientific) equipped with a Proxeon nanospray source (Thermo Fisher Scientific). Peptides were loaded onto a trap column (Thermo Fisher Scientific, PepMap C18, 5 mm×300 μm ID, 5 μm particles, 100 Å pore size) at 25 μL/min using 0.1% TFA as mobile phase. After 10', the trap column was switched in line with the analytical column (Thermo Fisher Scientific, PepMap C18, 500 mm×75 μm ID, 2 μm, 100 Å). The gradient started with the mobile phases: 98% A ($H_2O$/FA, 99.9/0.1, v/v) and 2% B ($H_2O$/ACN/FA, 19.92/80/0.08, v/v/v), increased to 35% B over 60', followed by an increase to 90% B over 5', held constant for 5' and decreased back 98% A and 2% B over 5' for equilibration at 30° C.

The Q Exactive HF mass spectrometer was operated in its data-dependent mode, using a full scan (m/z range 350-1650, nominal resolution of 120000, target value 3E6) followed by MS/MS scans of the 10 most abundant ions. MS/MS spectra were acquired using a normalized collision energy of 35%, isolation width of 1.2 m/z, resolution of 60.000, target value of 1E5 and first fixed mass set to 115 m/z. Precursor ions selected for fragmentation (exclude charge state unassigned, 1, >8) were put on a dynamic exclusion list for 30". Additionally, the minimum AGC target was set to 1E4 and the intensity threshold was 4E4. The peptide match feature was set to preferred and the exclude isotopes feature was enabled.

Proteomics Data Analysis

Raw data was processed with Proteome Discoverer (version 1.4.1.14, Thermo Fisher Scientific). Database searches were performed using MS Amanda (version 1.4.14.8240) against a database comprised of the human SwissProt database and appended contaminants (20508 protein sequences in total). Oxidation of methionine was set as dynamic modification and carbamidomethylation of cysteine and TMT at the N-terminus and lysine were specified as fixed modifications. Trypsin was defined as the proteolytic enzyme, cleaving after lysine or arginine, except when followed by proline, and up to two missed cleavages were allowed. Precursor and fragment ion tolerance were set to 5 ppm and 0.03 Da respectively. Identified spectra were rescored using Percolator and filtered to 0.5% FDR at the peptide spectrum match level. Protein grouping was performed in Proteome Discoverer applying a strict parsimony principle. Reporter ion intensities were extracted from the most confident centroid mass with an integration tolerance of 10 ppm. For all proteins detected with at least 2 unique peptides protein level quantification was computed based on all unique peptides within a given protein group. Statistical confidence of differentially abundant proteins was calculated using limma.

Preparation of Cellular Metabolites for Mass Spectrometry Cells were seeded at $2 \cdot 10^5$ cells/ml in pre-warmed growth medium in presence of 100 µM IAA or DMSO (1:5000 (v/v)). Medium was exchanged after 24 h and cells were counted and collected after 48 h, washed twice with PBS and snap-frozen. Pellets of $4 \cdot 10^6$ cells per sample were lysed in a mix of MeOH, ACN and $H_2O$ (in a ratio of 2:2:1 (v/v)), vortexed and snap-frozen. For complete lysis, cells underwent three cycles of snap-freezing, thawing and sonication (10', 4° C., maximum intensity in a Bioruptor sonication device (Diagenode)). Proteins were precipitated for 1 h at −20° C. followed by centrifugation (15', 18000 g, 4° C.). Supernatants were recovered and evaporated in a SpeedVac concentrator, pellets were re-dissolved in a 1:1-mixture of ACN and $H_2O$ (v/v) by sonication (10', 4° C.) and remaining debris was removed by centrifugation (4° C., 15', 18000 g).

Targeted LC-MS/MS of Cellular Metabolites

Prior to analysis, 50µl ACN was added to 60 µl of each sample and 3p1 were injected onto an UltiMate 3000 XRS HPLC system (Dionex, Thermo Scientific). Metabolites were separated using a 14' gradient starting at 5% mobile phase A (10 mM ammonium acetate in water, pH 7.5) and ramping up to 50% A in phase B (ACN) using a ZIC-HILIC column (100×2.1 mm, 3.5 µm, 200 Å, Merck) and employing a flow rate of 100µl/min. MS/MS was performed using a TSQ Quantiva triple quadrupole mass spectrometer (Thermo Scientific), using selected reaction monitoring (SRM) in the negative ion mode. Samples from three independent experiments were each analyzed in technical triplicates and MS data were analyzed using TraceFinder (Thermo Scientific).

Results

Figure 25:
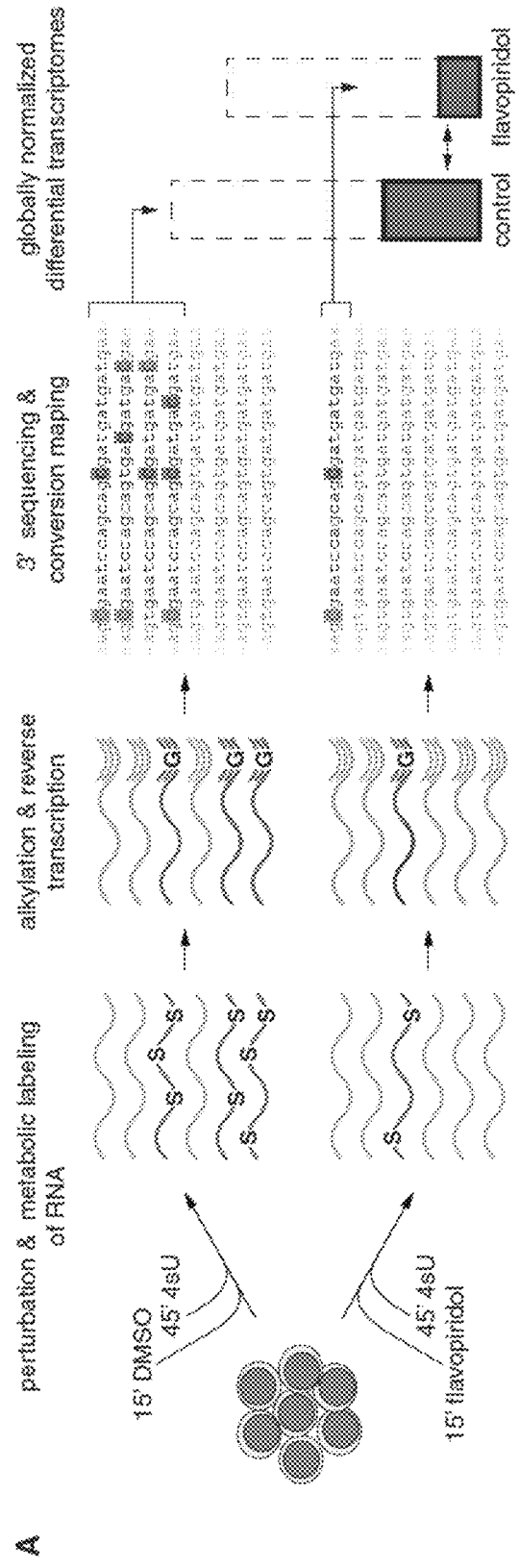
FIG. 25. Time-resolved mapping of transcriptional responses using SLAM-seq. (A) Sample workflow of a SLAM-seq experiment mapping responses after 15 to 60' of flavopiridol treatment (300 nM) in K562 cells. (B) Mapping of total and converted (2 T>C) reads for a low-turnover gene, GAPDH without or with flavopiridol treatment. (C) Box plots of flavopiridol-induced expression changes considering all reads or reads with ≥1 and ≥2 T>C conversions. Whiskers indicate 5-95% range. (D) Simplified schematic of BCR/ABL effector pathways and kinase inhibitors investigated using SLAM-seq in K562 cells (30' pre-treatment, 60'$s^4U$ labelling). (E). Heatmap and hierarchical clustering of the 50 most variable up- and down-regulated genes in SLAM-seq and their behavior at the total mRNA level in K562 cells treated with the indicated inhibitors. (F) Estimated half-lives of genes detected as ≥2-fold deregulated in total mRNA or SLAM-seq by at least one inhibitor in (D). (G) Principal component analysis of SLAM-seq reads from K562 treated with indicated inhibitors as described in (D).
Figure 25:
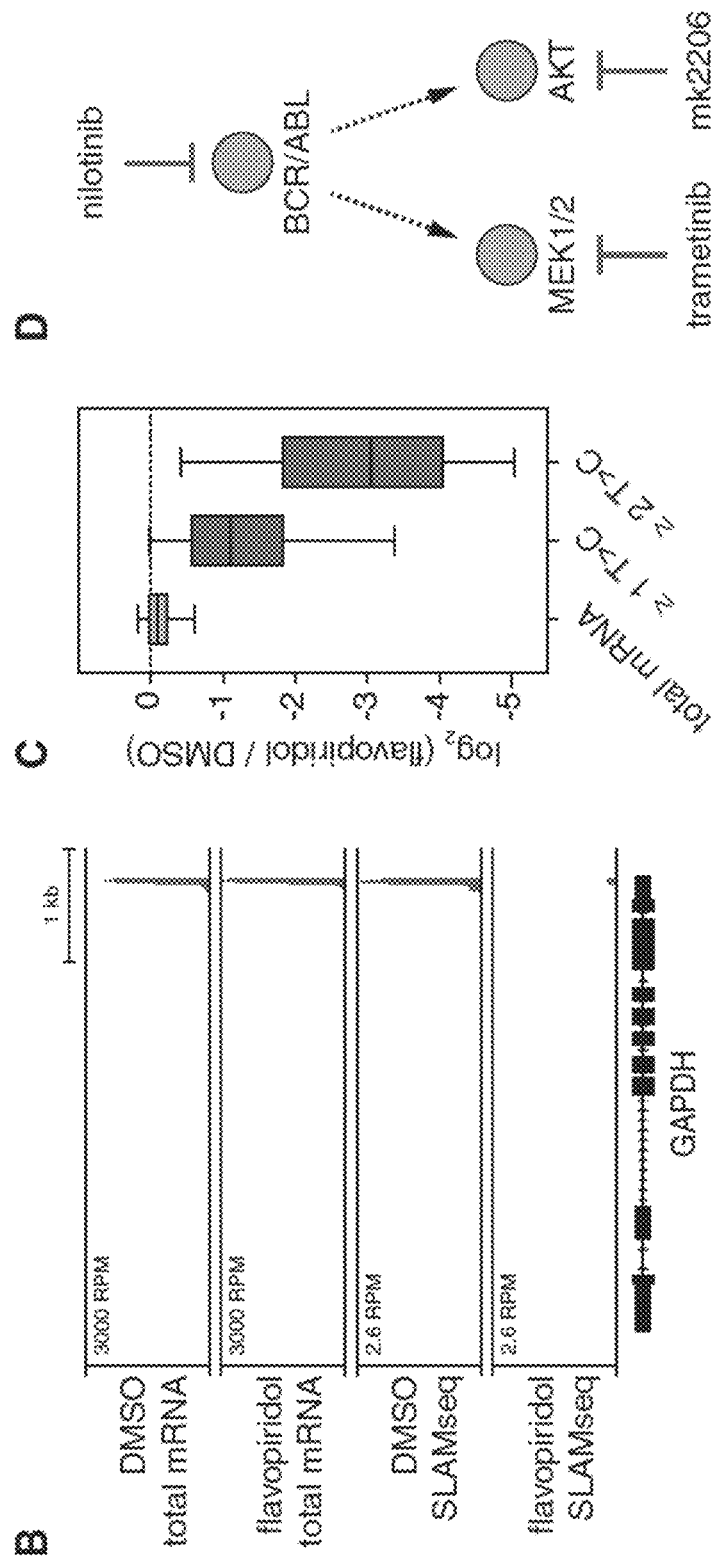
Figure 25:
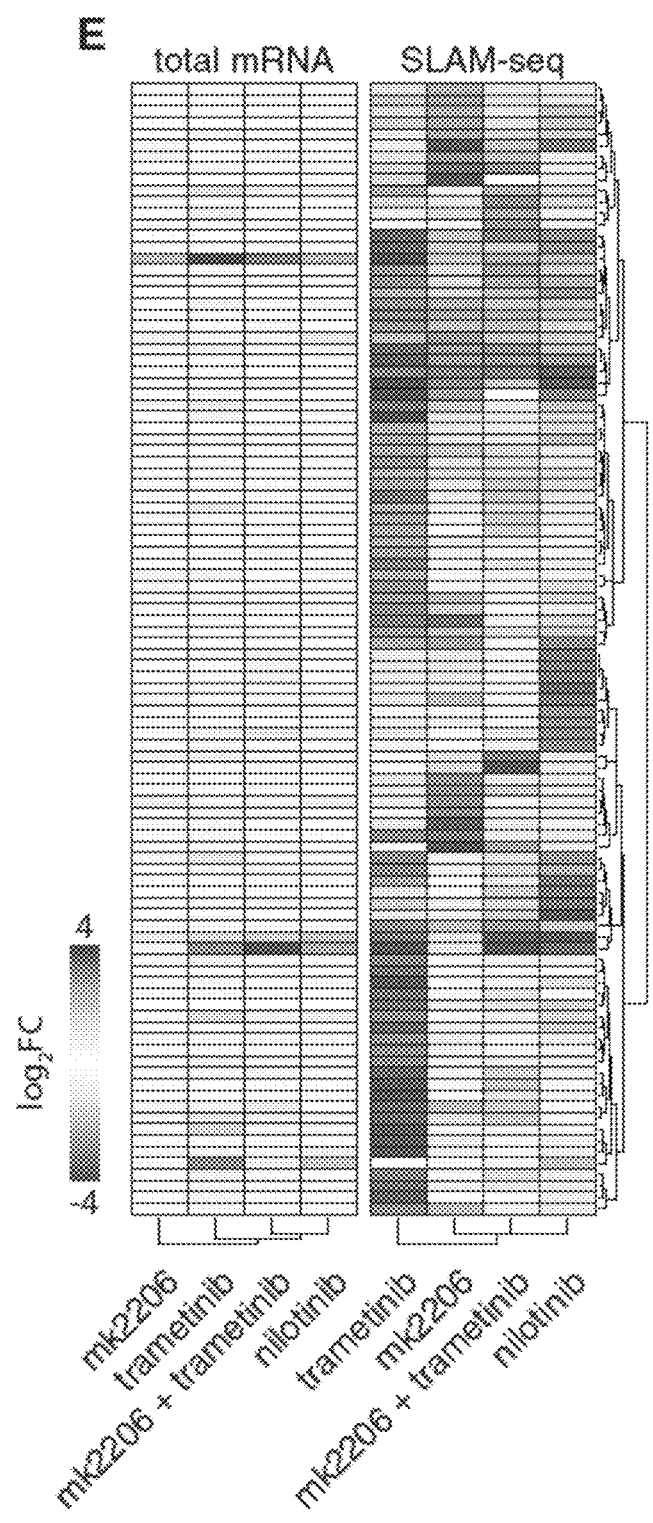
Figure 25:
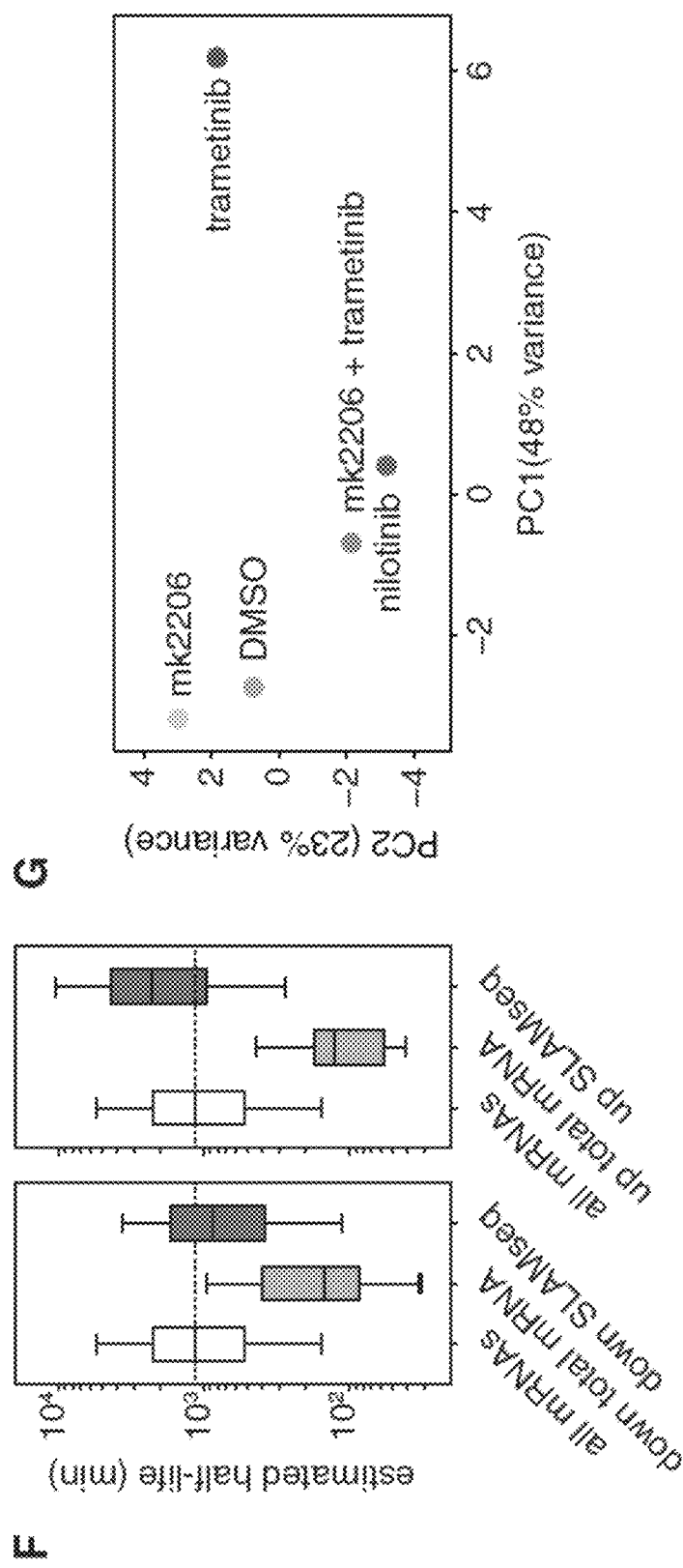

SLAM-seq after 30' of pre-treatment and 60' of s4U labeling revealed prominent immediate responses to small-molecule inhibitors (FIG. 25E, FIG. 30C) that were not biased by mRNA half-lives, while changes at the total mRNA level were confined to a few short-lived mRNAs (FIG. 25F). Single-agent treatment with all three inhibitors triggered specific and distinct transcriptional responses (FIG. 30C), while combined treatment with inhibitors of MEK and AKT approximated to effects observed after BCR/ABL inhibition (FIGS. 25, E and G), consistent with their function in major effector pathways of BCR/ABL. Together, these pilot studies establish SLAM-seq as rapid, accessible and scalable approach to probe specific and global transcriptional responses at the level of mature mRNAs, irrespective of mRNA half-lives and at time-scales that exclude indirect effects. Combined with rapid perturbation of specific regulators, SLAM-seq therefore enables the unambiguous identification of direct transcriptional target genes.

To generalize this approach for investigating the vast number of regulators for which, as in the case of BRD4, no selective inhibitors are available, we sought to combine SLAM-seq with chemical-genetic protein degradation. To achieve sufficiently rapid kinetics for unambiguous target assignment we employed the auxin-inducible degron (AID) system, which degrades AID-tagged proteins within less than 1 h. Specifically, we modified the BRD4 locus of K562 cells to harbor a minimal AID-tag (FIG. 26A), and transduced homozygously tagged clones with a lentiviral vector expressing high levels of the rice F-box protein Tir1, which mediates ubiquitination of AID-tagged proteins upon treatment with auxin (indole-3-acetic acid, IAA). Indeed, auxin treatment of AID-tagged cells triggered a highly specific (FIGS. 31, A and C) and near complete degradation of BRD4 within 30' (FIG. 26B and FIG. 31B). While introduction of the tag or Tir1 expression and auxin treatment were well tolerated, prolonged degradation of BRD4 strongly suppressed proliferation (FIGS. 31, D and E), in line with its reported essential function.

Figure 26:
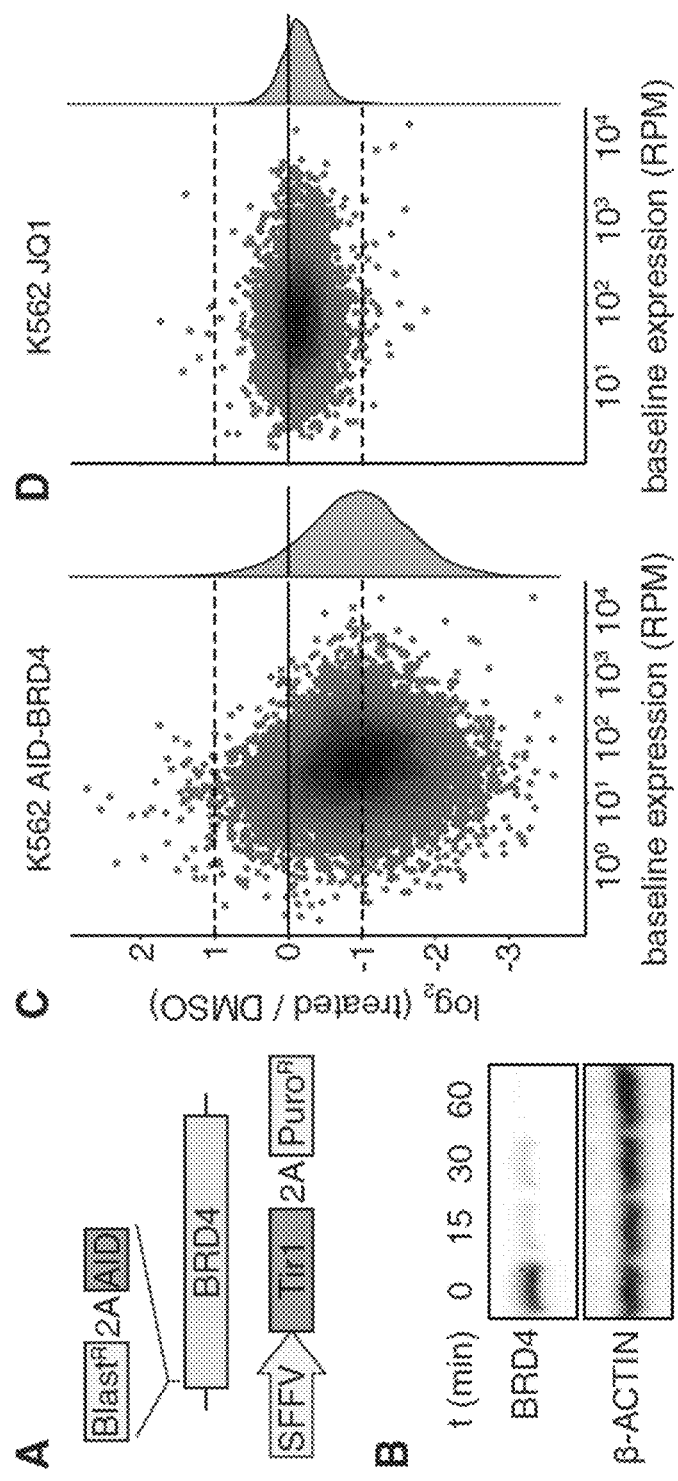
FIG. 26. BETi hypersensitivity is distinct from global transcription control by BRD4. (A) Schematic of the AID-BRD4 knock-in allele and Tir1 delivery vector SOP. (B) Immunoblotting of BRD4 in K562AID-BRD4 cells transduced with SOP and treated with auxin (100 µM IAA). (C) SLAM-seq response of K562AID-BRD4 cells treated with auxin for 30' before $s^4U$ labeling for 60'. (D) SLAM-seq response of K562 cells treated with JQ1 (200 nM) for 30' before s4Us$^4U$ labeling for 60'. (E) Comparison of SLAM-seq responses to JQ1 in K562 cells shown in (C) and identically treated MV4-11 cells. R, Pearson correlation coefficient. (F) Comparison of mean SLAM-seq responses and mean CRISPR scores indicating gene essentiality (14, 15) in K562, MOLM-13 and MV4-11 cells. Shown are all genes significantly down-regulated in all three cell lines (FDR≤0.1). (G) Principal component analysis of $s^4U$ labeled SLAM-seq reads from MOLM-13 cells treated with JQ1 or CDK9 inhibitor NVP-2 as performed in (C). (H) Heatmap and hierarchical clustering of Spearman's rank correlations between SLAM-seq responses to JQ1 and CDK9 inhibition in indicated cell lines.
Figure 26:
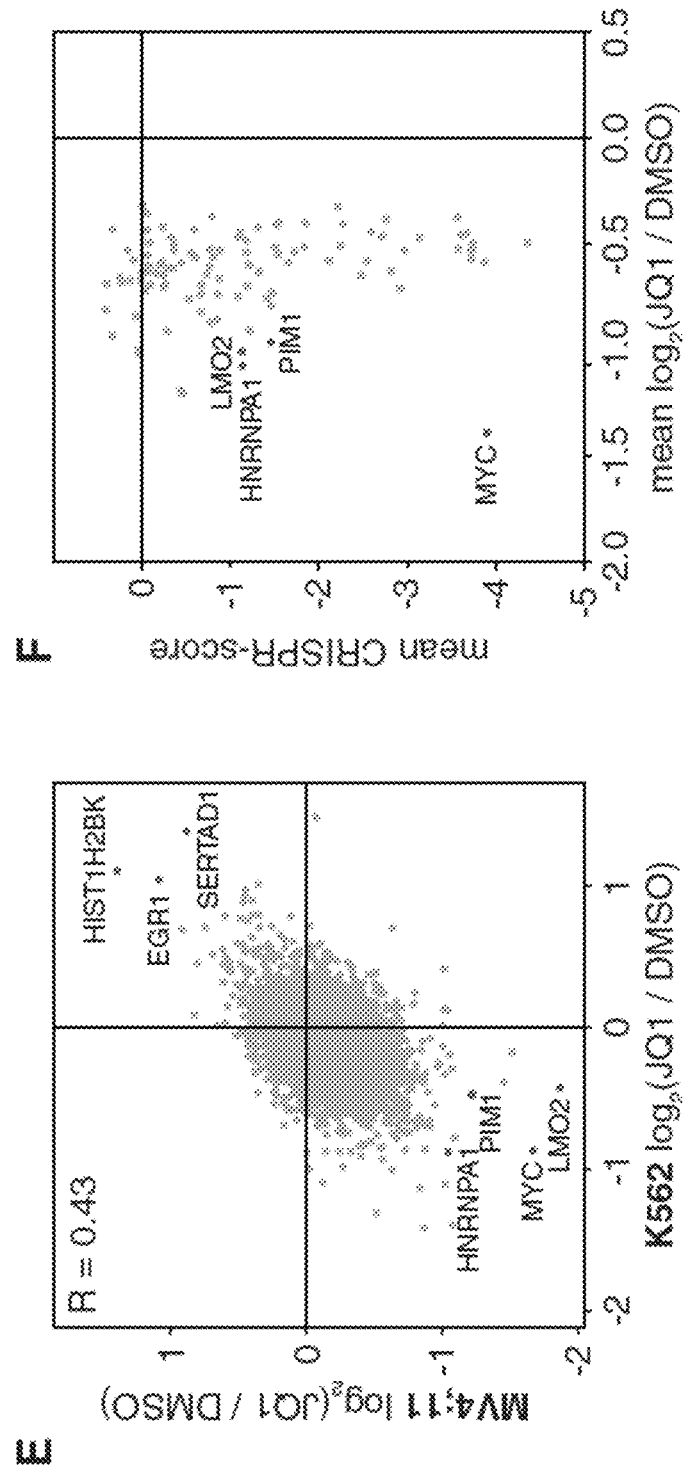
Figure 26:
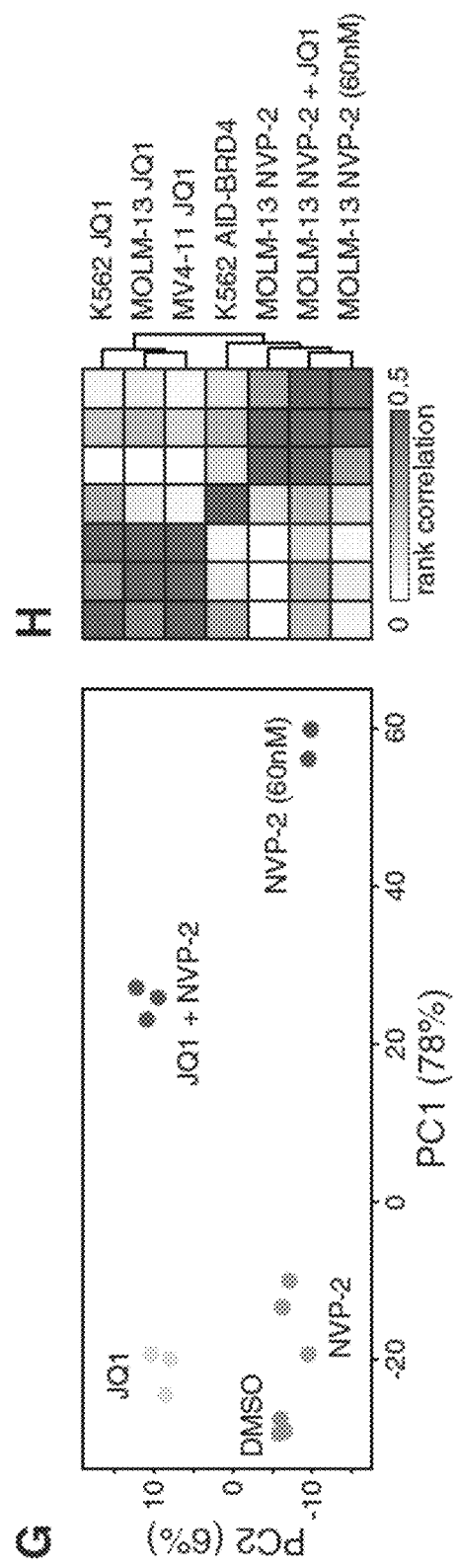

To next map direct transcriptional consequences of BRD4 degradation, we treated cells with auxin for 30' and labeled newly synthesized RNA for the following 60' with s4U. Subsequent quantification of labeled mRNAs by SLAM-seq revealed a global downregulation of transcription (FIG. 26C and FIG. 31F), similar to effects of CDK9 inhibition. To investigate regulatory events underlying this phenomenon, we measured levels of chromatin-bound core transcription machinery upon BRD4 degradation. While neither components of the pre-initiation complex, nor DSIF, NELF or P-TEFb showed impaired global recruitment, we noted a marked decrease in phosphorylation of Pol2 at S2 but not S5 of its C-terminal heptad repeats (FIG. 26D), indicative of a defect in promoter proximal pause release. Indeed, spike-in controlled ChIP-sequencing of Pol2 upon BRD4 degradation (after 60' of auxin treatment) showed a marked increase in Pol2 occupancy at active transcription start sites (TSS), while Pol2 density was diminished throughout gene bodies (FIGS. 26, E and F and FIG. 32A). Similarly, levels of S5-phosphorylated Pol2 increased at promoters, while S2-phosphorylated Pol2 (associated with late elongation steps) was greatly reduced throughout gene bodies (FIGS. 26, E and F and FIGS. 32, B and C). These findings are in line with a widespread reduction of transcription upon pan-BET protein degradation independent of CDK9 recruitment to chromatin, and demonstrate that loss of BRD4 alone is sufficient to mediate these effects. Altogether these results establish a central role of BRD4 in licensing release of stalled polymerases at most active promoters.

While these findings are in line with the promiscuous binding of BRD4 to active TSS and its physical interaction with core transcriptional machinery, they contrast selective effects observed after BETi treatment in conventional expression analysis. To define immediate transcriptional effects of BETi and compare them to BRD4 degradation, we performed SLAM-seq following treatment with different doses of the BETi JQ1 in K562 cells and the acute myeloid leukemia (AML) cell line MV4-11. In both cell types, high-dose JQ1 treatment (1 or 5 µM) broadly suppressed transcription (FIG. 26G, FIG. 33A) and globally reduced Pol2-S2 phosphorylation (FIG. 33B), similar to effects observed after BRD4 degradation, indicating that global transcriptional functions of BRD4 are BET bromodomain-dependent. Importantly, effects of high-dose BETi treatment on Pol2 S2 phosphorylation were also recapitulated by knockdown of BRD4 at time points preceding anti-proliferative effects (FIGS. 33, C and D), while suppression of BRD2 or BRD3, the two other ubiquitously expressed BETi targets, did not trigger such phenomena. These results demonstrate that global transcriptional effects of BETi are primarily mediated by BRD4 inhibition and cannot be compensated by other BET-bromodomain containing proteins.

As JQ1 doses above 1 µM vastly exceed growth-inhibitory concentrations in AML and other JQ1-sensitive cancer cell lines, we sought to explore direct transcriptional responses to a more selective dose of 200 nM, which triggers strong anti-leukemic effects in a wide range of AML models. In K562 cells, one of few BETi insensitive leukemia cell lines, 200 nM JQ1 induced a selective deregulation of a small number of transcripts (FIG. 26H). Surprisingly, treatment of two highly sensitive AML cell lines with the same dose triggered transcriptional responses that were comparable in scale (FIG. 26H and FIGS. 34, A and B) and affected a similar set of BETi-hypersensitive transcripts, which included MYC and other pan-myeloid dependencies (FIG. 26I and FIGS. 34, C and D). These findings show that BETi resistance in leukemia is determined by secondary adaptation rather than a lack of primary transcriptional responses. We also noted a small set of genes that were commonly upregulated following BET inhibition or BRD4 degradation (FIG. 34E). Interestingly, these include EGR1, a tumor suppressor in AML, which may contribute to potent effects of BETi in this context. Altogether, our results reveal a profound dose-dependency of primary transcriptional responses to BETi and show that therapeutically active doses trigger anti-leukemic effects through deregulating a small set of hypersensitive genes. Moreover, this illustrates that partial inhibition of basic transcriptional machinery can elicit highly specific responses which can be exploited to selectively target cancer dependencies.

Figure 27:
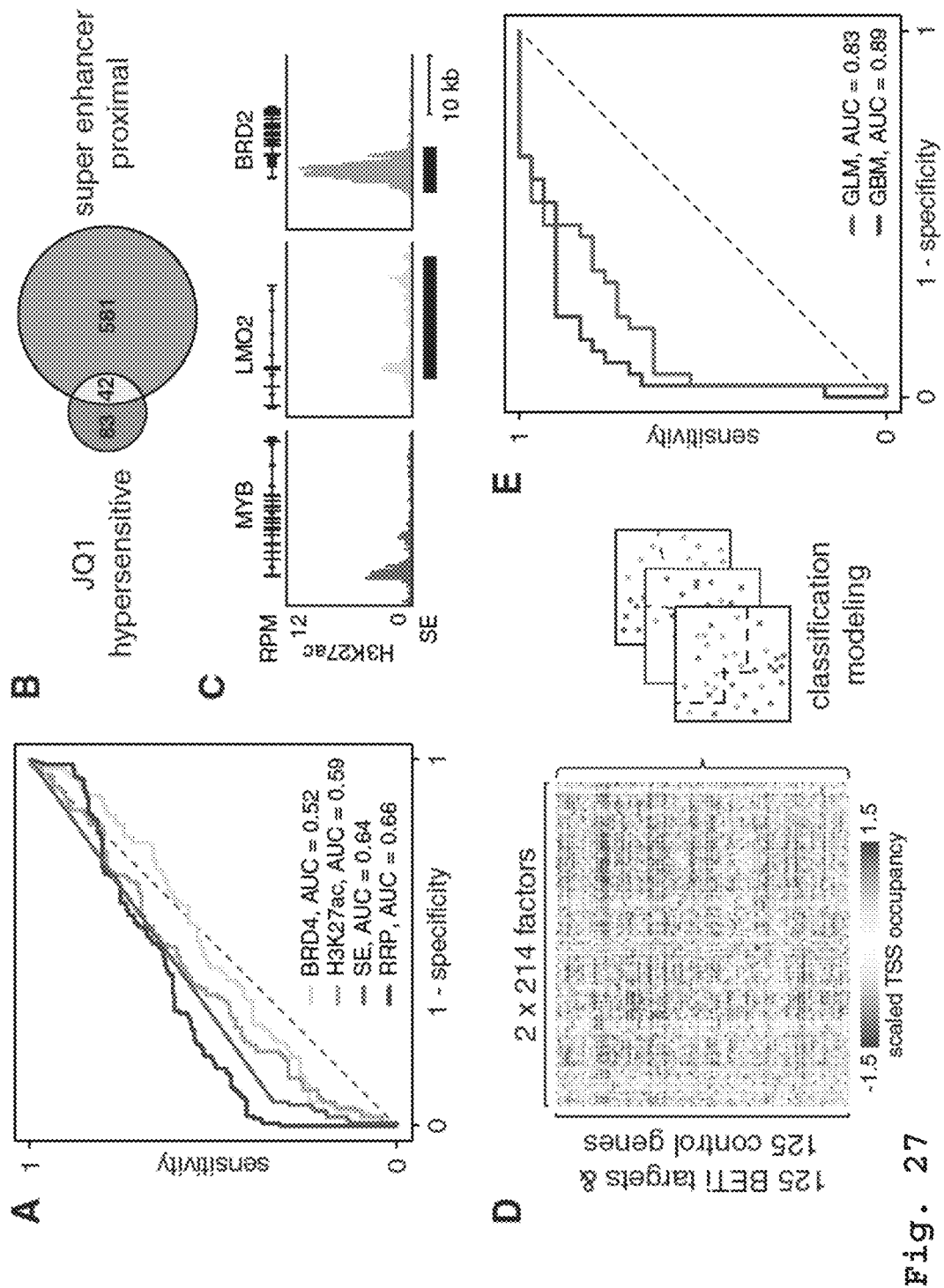
FIG. 27. Chromatin context determines BETi hypersensitivity. (A) ROC curve for distinction of BETi hypersensitive genes from an expression matched control set by indicated predictors in K562 cells. (B) Venn-diagram showing overlap of BETi hypersensitive genes and published super enhancer targets in K562 cells. (C) Sample tracks of H3K27ac ChIP-seq and super enhancer annotation for selected genes exemplifying categories in (B). (D) Simplified model generation workflow for classifying BETi hypersensitive genes based on 214 chromatin signatures within 500 bp or 2000 bp from TSS. (E) ROC curve as in (A) for two independent chromatin signature-based models of BETi hypersensitivity assessed on a held-out test set. (F) Relative contribution of the five strongest positive and negative predictors to the GLM shown in (E) based on their normalized model coefficients. (G) Heatmap and hierarchical clustering of relative ChIP-seq densities of predictive factors in (F) at TSS of 125 BETi hypersensitive genes.
Figure 27:
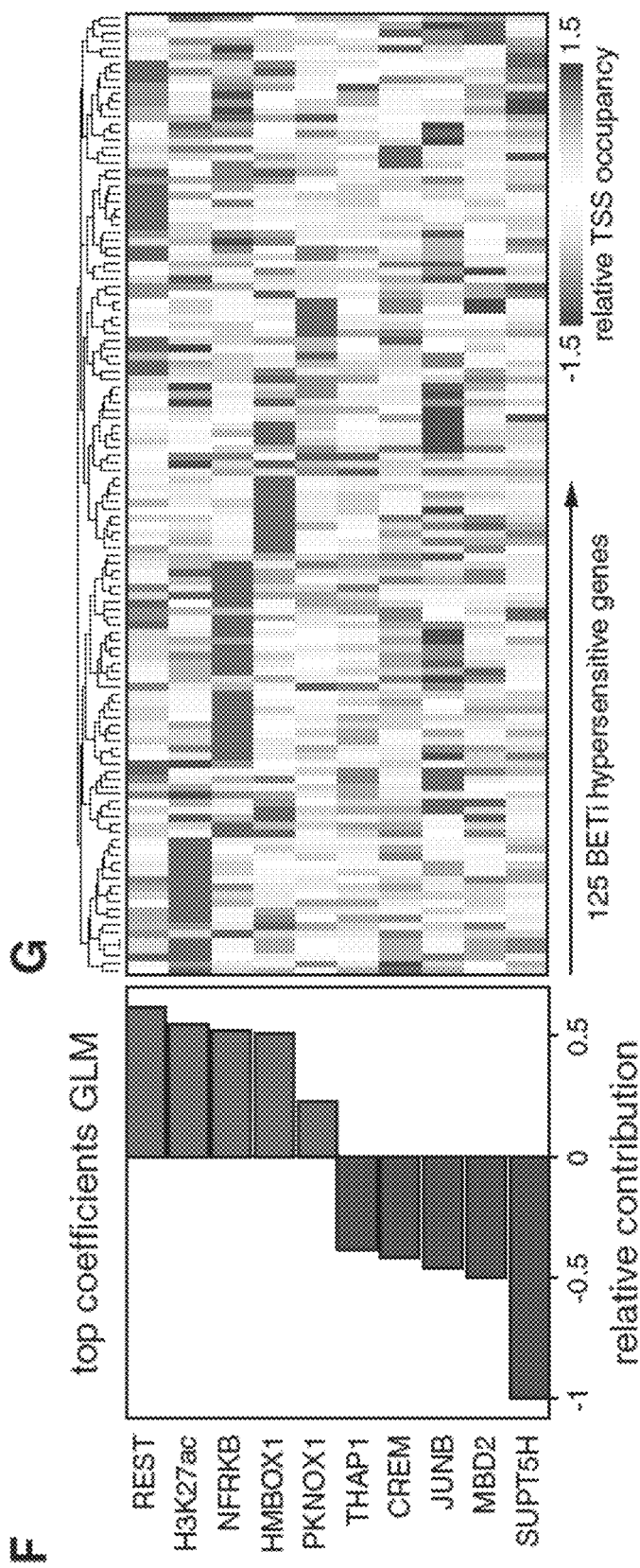

To explore factors that render certain transcripts hypersensitive to BETi, we wondered whether this phenomenon simply reflects a pronounced sensitivity to interference with general Pol2 pause release machinery. To test this, we used SLAM-seq to compare transcriptional responses to BET inhibition (200 nM JQ1) to effects triggered by different doses of the selective CDK9 inhibitor NVP-2. While high-dose CDK9 inhibition (60 nM NVP-2) globally suppressed transcription, an intermediate dose (6 nM NVP-2) triggered selective transcriptional responses (FIG. 35A) that were distinct from the conserved response to BETi (FIGS. 27, A and B, and FIG. 35B). As CDK9 and BET inhibitors have displayed strongly synergistic effects in previous reports and in our studies in AML (FIGS. 35, C and D), we sought to investigate transcriptional responses underlying this phenomenon. In contrast to selective single-agent effects, combining intermediate doses of JQ1 and NVP-2 triggered a global loss of transcription similar to high-dose CDK9 inhibition (FIGS. 27, A and B and FIG. 35A). These observations hold true in a genetically distinct AML cell line (FIGS. 35, E and F), suggesting that the therapeutic synergy between BETi and CDK9i is largely based on synergistic suppression of global transcription, raising concerns about the tolerability of this combination. Overall, our results reveal that therapeutically active doses of CDK9 and BET inhibitors, despite the general role of their targets in Pol2 pause release, exploit different bottlenecks in this process to trigger selective transcriptional responses.

To investigate whether the phenomenon of BETi hypersensitivity is determined by specific chromatin features, we first tested whether BRD4 occupancy levels at TSS or their accessibility to BETi could distinguish direct BETi targets (FDR≤0.1, $\log_2$ FC≤−0.7) from an equally sized cohort of unresponsive genes with identical baseline expression (FDR≤0.1, −0.1≤$\log_2$ FC≤0.1; FIG. 36A). While BRD4 occupancy could barely outperform random selection of genes (AUC 0.52, FIG. 31C), recently reported chromatin binding levels of BETi measured by Click-seq could partly account for BETi responses (AUC 0.63; FIG. 36B), suggesting that differences in drug accessibility contribute to selective BETi effects. Another broadly adopted model attributes transcriptional and therapeutic effects of BETi to their ability to selectively suppress super-enhancers, which has been challenged by a recent study identifying H3K27ac-based regulatory potential as superior predictor of BETi targets. As these studies relied on conventional RNA-seq after prolonged drug treatment, we reevaluated both models using SLAM-seq profiles. Both the H3K27ac-based regulatory potential of genes, as well as their association with super-enhancers, predicted hypersensitivity to BETi with modest accuracy (AUC 0.66 and 0.64, respectively, FIG. 27C). However, two-thirds of BETi-sensitive genes could not be assigned to super-enhancers, and the vast majority of expressed super-enhancer associated genes did not respond to BETi treatment (FIGS. 27, D and E). These observations hold true in other leukemia cell lines (FIG. 36C) and show that the sensitivity to BET inhibition is associated with, but not determined by the presence of super-enhancers, suggesting that more complex factors underlie this phenomenon.

To explore these, we took advantage of extensive profiling data available for K562 cells and devised an unbiased approach for modeling combinatorial modes of gene regulation. Specifically, we extracted signals of 214 ChIP- and methylome sequencing experiments within 500 and 2000 bp around the TSS of BETi-sensitive and unresponsive genes, and used this data to train various classification models that were later evaluated based on held-out test genes (FIG. 27F and FIG. 36D). This approach yielded multiple classifiers predicting BETi sensitivity with high fidelity (AUC>0.8, FIG. 27G and FIG. 36E), among them a generalized linear model (GLM) derived by elastic net regression. Re-analyzing coefficients of this model revealed that several factors including high levels of TSS-proximal REST and H3K27ac are associated with BETi hypersensitivity, while high occupancy of SUPT5H, itself a regulator of elongation, was the strongest negative predictor (FIG. 27H and FIG. 37A). Unsupervised clustering revealed that the most predictive TFs and co-factors are enriched only at distinct sub-clusters of BETi sensitive or unresponsive genes (FIG. 27I and FIG. 37B). For example, high loads of the positive predictors NFRKB and HMBOX1 were found in distinct groups of BETi-sensitive genes, while high binding of CREM and SUPT5H was observed in distinct subclusters of BETi-insensitive genes. Together, these findings suggest that the transcriptional response to BETi is determined by locus-specific regulators and cannot be predicted based on a single unifying chromatin factor.

Similar to complex determinants of BETi sensitivity, therapeutic effects of BETi are likely mediated through deregulation of multiple hypersensitive target genes. After validating MYC as a prominent BETi-hypersensitive gene in leukemia, the transcriptional and cellular response to MYC suppression must be viewed as key effector mechanism of BETi in this context. However, direct gene regulatory functions of MYC remain under debate between studies describing activating, repressive and dose-dependent effects on specific targets, as well as a role of MYC as a general transcriptional amplifier. To test these models, we sought to measure direct changes in mRNA output following acute loss of endogenous MYC. To this end, we engineered the MYC locus of K562 cells to harbor an AID-tag (FIG. 28A), which in homozygous Tir1-expressing clones triggered rapid MYC degradation within less than 30' (FIG. 28B). We then used SLAM-seq to quantify the output of newly synthesized mRNAs over 60' following MYC degradation. Compared to degradation of BRD4 and pharmacological CDK9 and BET inhibition, acute loss of MYC resulted in highly specific rather than global changes in mRNA production (FIG. 28C). These were dominated by repressive effects on 712 genes, while only 15 mRNAs were strongly up-regulated. Hence, in K562 cells, MYC does not act as a direct repressor or general amplifier of transcription, but predominantly functions as a transcriptional activator of specific target genes.

Since MYC is known to occupy virtually all active promoters, we next investigated how MYC exerts selective transcriptional activation despite ubiquitous binding. To this end, we trained classification models to predict MYC-dependent transcripts (FDR≤0.1, $\log_2$ FC≤-1) based on different ChIP-seq signals at their promoter. Elastic net regression yielded a simple GLM that was highly predictive of MYC-dependent gene regulation (AUC 0.91). The strongest contributor in this model was the abundance of MYC itself. Indeed, while the presence of MYC at promoters determined by conventional peak calling fails to identify MYC-sensitive transcripts, binding levels of MYC or its co-factor MAX predict MYC-dependent gene regulation with intermediate accuracy (AUC 0.76 and 0.74, respectively. Together, these results suggest that directly MYC-dependent transcripts are defined by strong MYC binding and further modulation or compensation by additional factors such as MNT, NKRF, TBL1XR1, EP300 and YY1.

Figure 28:
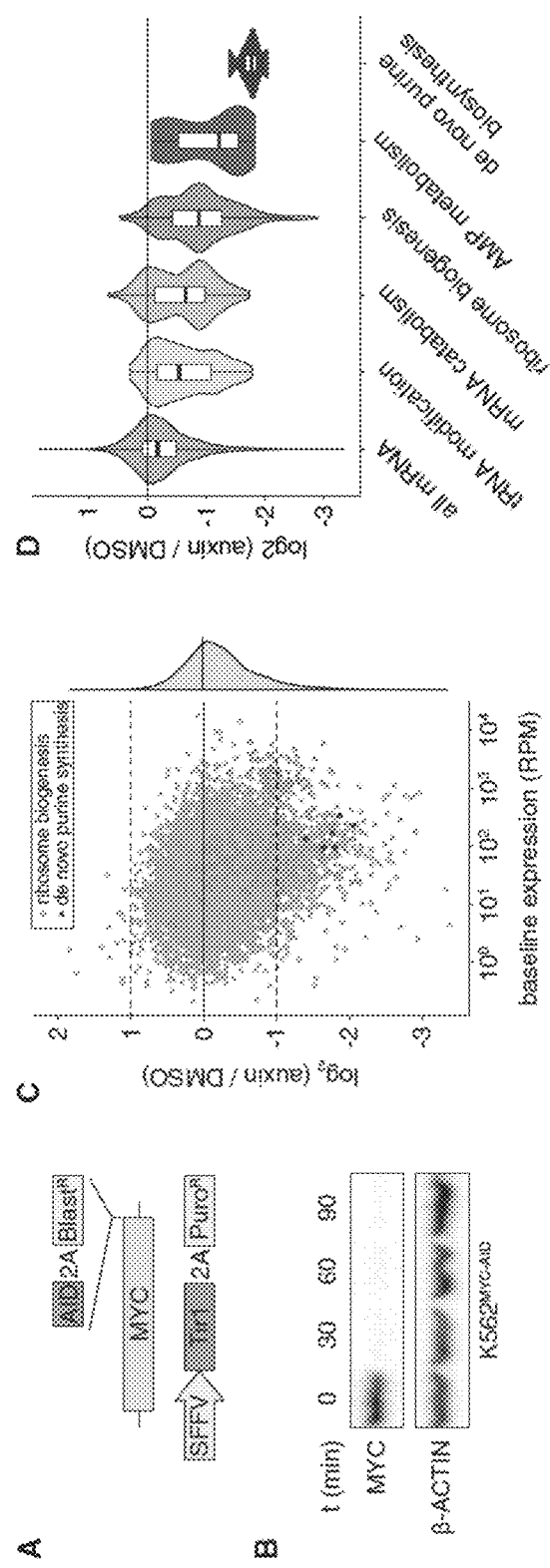
FIG. 28. MYC is a selective direct activator of cellular metabolism across cancer types. (A) Schematic of MYC-AID allele and Tir1 vector. (B) MYC immunoblotting in K562MYC-AID cells after auxin treatment for indicated times. (C) SLAM-seq profile following MYC degradation in K562MYC-AID cells (30' auxin pre-treatment, 60'$s^4U$ labeling). (D) SLAM-seq responses of all mRNAs and significantly enriched gene sets. (E) MYC immunoblotting in HCT116MYC-AID cells as in (B). (F) Comparison of SLAM-seq responses in K562MYC-AID and HCT116MYC-AID cells. (G) ROC curves of different predictors distinguishing MYC-dependent genes in (C) (FDR≤0.1, log 2FC≤−1) from an expression-matched control set. MYC/MAX ChIP, genes ranked by ChIP-seq signal within 2 kbp from TSS; GLM, elastic-net GLM based on 214 chromatin profiles. (H) Relative contribution of strongest positive and negative predictors to the GLM in (G). (I) Expression of MYC and SLAM-seq-based MYC-target signature in 672 cancer cell lines. Samples with MYCN or MYCL levels exceeding MYC levels are highlighted. (J, K)
Figure 28:
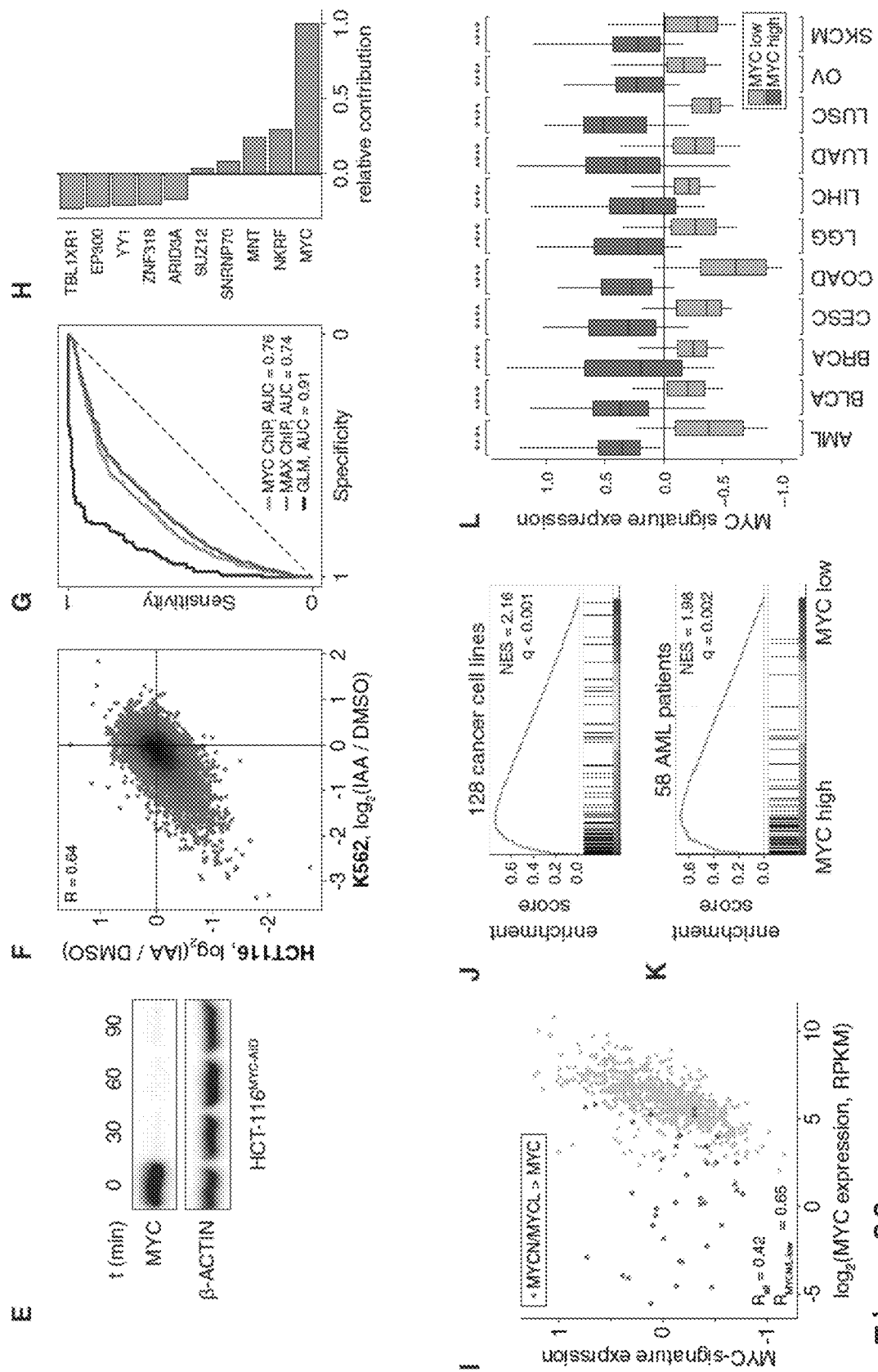

To investigate the cellular function of MYC-dependent gene regulation, we analyzed the enrichment of biological processes among direct MYC target genes. Strikingly, acute MYC-loss predominantly down-regulated genes associated with protein and nucleotide biosynthesis (FIG. 28D), including 36% of all ribosome biogenesis factors, key regulators in AMP metabolism, and all six enzymes of the de-novo purine synthesis pathway (FIGS. 28, C and D). Indeed, MYC degradation progressively impaired protein synthesis (FIG. 28E) and led to a strong reduction in cellular AMP and GMP levels as well as their upstream intermediate AICAR prior to the onset of proliferation defects (FIG. 28F). MYC's role in directly controlling key enzymes in protein and nucleotide biosynthesis, as well as several subunits of Polymerases I, II and III, provide an explanation for the reported increase in total cellular RNA upon MYC overexpression, in support of the notion that these effects are of secondary nature and not due to global transcriptional effects.

To test whether direct transcriptional functions of MYC are conserved in other contexts, we engineered homozygous AID-tags into the MYC locus of HCT116 colon carcinoma cells, which express particularly high levels of MYC. As for K562, auxin treatment of TIR1-expressing HCT116$^{MYC\text{-}AID}$ cells triggered complete degradation of MYC within less than 30' (FIG. 28G). SLAM-seq profiling revealed highly selective transcriptional effects (FIG. 28H) that affected the same cellular processes and correlated with the response in K562 cells (R=0.64, FIG. 28H). To test whether the conservation of MYC targets between two unrelated cell lines extends to other cancer types, we derived a signature of the 100 most strongly downregulated genes in SLAM-seq and compared its expression to MYC levels in a panel of 672 cancer cell lines. Indeed, expression levels of MYC and our signature correlated well (FIG. 28I), except for a small fraction of out-tiers expressing low levels of MYC without losing the signature. Notably, all of these outliers express high levels of MYCN or MYCL, indicating that MYC paralogs have redundant functions in the regulation of core MYC targets. Our signature of direct MYC targets was also strongly correlated with MYC levels in TCGA RNA-seq profiles from 5583 primary patient samples across 11 major human cancers (FIG. 28J). Together, these findings demonstrate that across diverse human cancers MYC drives expression of a conserved set of transcriptional targets, which should be considered as entry points for blocking its oncogenic functions.

In summary, combining rapid chemical-genetic perturbation and SLAM-seq establishes a simple yet powerful strategy for probing specific and global direct functions of transcription factors and co-factors. Using this approach, we functionally characterize BRD4, a factor widely studied as a regulator of lineage- and disease-associated expression programs, as global co-factor in transcriptional pause-release. On the other hand, we find that MYC, which has previously been implicated as a global transcriptional amplifier, activates a confined and conserved set of target genes to fuel basic anabolic processes, particularly protein and nucleotide biosynthesis. More generally, by enabling the direct quantification of changes in mRNA output, SLAM-seq provides a simple, robust and scalable method for defining direct transcriptional responses to any perturbation, and thereby explore the regulatory wiring of a cell.

The invention claimed is:

1. A method of identifying a polynucleic acid (PNA) comprising the steps of: providing a PNA; modifying one or more nucleobases of the PNA by incorporation of a thiol modified nucleobase into the PNA through biosynthesis in a cell; and further comprising alkylating said thiol modified nucleobase with an alkylating agent that comprises a hydrogen bonding partner, thereby altering the base pairing capacity of the one or more nucleobases; base pairing a complementary nucleic acid to the PNA, comprising base pairing to at least one modified nucleobase; identifying the sequence of the complementary nucleic acid at least at the position that is complementary to at least one modified nucleobase.

2. The method according to claim 1, wherein the modification leads to an altered base pairing behaviour, thereby altering the preferential base pairing between A and T/U and between C and G as compared to the natural nucleobases selected from the group consisting of A, T/U, C and G.

3. The method according to claim 1, wherein the modification comprises alkylating on position 4 of a uridine with an alkylating agent that comprises the hydrogen bonding partner.

4. The method according to claim 1, wherein the PNA comprises one or more 4-thiouridine or 6-thioguanosine.

5. The method according to claim 1, wherein the PNA is synthesized in a cell with a modification that alters said base pairing capacity.

6. The method according to claim 1, wherein base pairing to at least one modified nucleobase leads to base pairing with a nucleobase that has not been modified, with said nucleobases being otherwise the same.

7. The method according to claim 1, wherein the PNA comprises or consists of RNA or DNA.

8. The method according to claim 1, wherein for each nucleotide type selected from A, G, C, U or T the modified PNA comprises more natural nucleotides than modified nucleotides.

9. The method according to claim 1, wherein the PNA comprises 1, 2, 3, 4, 5, 6, 7, 8, 9, 10 or more and up to 30 modified nucleotides.

10. The method of claim 1, wherein providing a PNA comprises expressing the PNA in cell; said method further comprises isolating the PNA from the cell; modifying one or more nucleobases of the PNA in the cell wherein the modification(s) in the cell adds or removes a hydrogen bonding partner of one or more nucleobase, thereby altering the base pairing capacity of the one or more nucleobases.

11. The method according to claim 1, wherein one or more cells are cultured or grown in at least two culturing or growth phases, wherein one culturing or growth phase comprises incorporation of a modified nucleotide into biosynthesized PNA, which is modified by addition or removal of a hydrogen bonding partner, and another culturing or growth phase that lacks such incorporation of the modified nucleotide into biosynthesized PNA or wherein modified nucleotides are incorporated into biosynthesized PNA at a different concentration in the culturing phase or the growth phase; or wherein the method comprises incorporation of a modified nucleotide into biosynthesized PNA of at least two different cells or into at least two different groups of cells.

12. The method according to claim 11, wherein the biosynthesized PNA of the two culturing or growth phases or of the at least two different cells or at least two different groups of cells are collected from said cells, mixed, and labelling the PNA according to the cell origin of the PNA, and wherein base pairing a complementary nucleic acid to the PNA comprises generation of complementary polynucleic acid strands by transcription.

13. The method of claim 12, further comprising determining the sequence of the complementary polynucleic acid strands and comparing the strand sequences.

* * * * *